(12) United States Patent
Fang et al.

(10) Patent No.: US 7,985,746 B2
(45) Date of Patent: *Jul. 26, 2011

(54) IMIDAZOAZEPINONE COMPOUNDS

(75) Inventors: Francis Fang, Andover, MA (US);
Shawn Schiller, Haverhill, MA (US);
Boris Seletsky, Andover, MA (US);
Mark Spyvee, Hampstead, NH (US)

(73) Assignee: Eisai R&D Management Co., Ltd., Tokyo (JP)

( * ) Notice: Subject to any disclaimer, the term of this patent is extended or adjusted under 35 U.S.C. 154(b) by 53 days.

This patent is subject to a terminal disclaimer.

(21) Appl. No.: 12/299,864

(22) PCT Filed: May 24, 2007

(86) PCT No.: PCT/US2007/012298
§ 371 (c)(1),
(2), (4) Date: Dec. 2, 2008

(87) PCT Pub. No.: WO2007/139833
PCT Pub. Date: Dec. 6, 2007

(65) Prior Publication Data
US 2009/0131405 A1  May 21, 2009

Related U.S. Application Data

(60) Provisional application No. 60/808,770, filed on May 26, 2006.

(51) Int. Cl.
*A61K 31/00* (2006.01)
*A61K 31/55* (2006.01)
*A61K 31/41* (2006.01)
*A01N 43/00* (2006.01)
*A01N 43/42* (2006.01)

(52) U.S. Cl. ......... 514/211.02; 514/211.09; 514/211.15; 514/212.03; 514/213.01; 514/284; 514/359

(58) Field of Classification Search ............ 514/211.02, 514/211.09, 211.15, 212.03, 213.01, 284, 514/359
See application file for complete search history.

(56) References Cited

U.S. PATENT DOCUMENTS
2006/0223116 A1  10/2006  Glimcher et al.

FOREIGN PATENT DOCUMENTS
| EP | 0 385 489 A1 | 9/1990 |
| EP | 1 619 193 A1 | 1/2006 |
| JP | 4-266886 A | 9/1992 |
| JP | 04266886 A | 9/1992 |
| WO | WO 2006-128143 A2 | 11/2006 |

OTHER PUBLICATIONS

Dixit VM et al. Agents acting on the central nervous system: Part XXXIV—studies on benzazepino[3,2-a] & [2,3-a]diazepines & benzazepino[3,2-c] & [2,3-c]imidazoles. Indian J. Chem. Jan. 1979. 17B: 72-73.
International Search Report, PCT/US2007/012261, mailed Nov. 7, 2007.
International Preliminary Report on Patentability, PCT/US2007/012261, mailed Dec. 11, 2008.
International Preliminary Report on Patentability, PCT/US2007/012298, mailed Dec. 11, 2008.
Examination Report, EP 07 795 237.2, dated Mar. 25, 2009.
International Search Report and Written Opinion, PCT/US2007/012298, mailed Nov. 28, 2007.

*Primary Examiner* — Sreeni Padmanabhan
*Assistant Examiner* — Renee Claytor
(74) *Attorney, Agent, or Firm* — Myers Bigel Sibley & Sajovec, P.A.

(57) ABSTRACT

The invention relates to compounds of formula I:

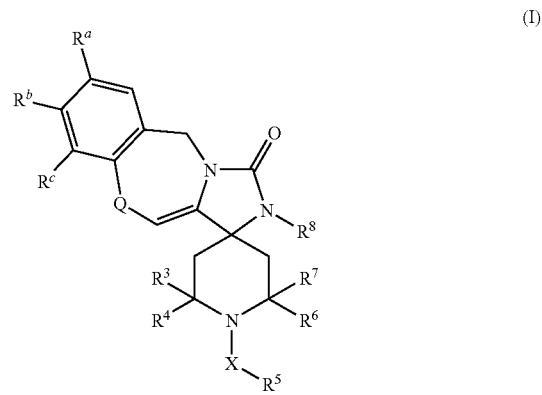

(I)

along with pharmaceutical compositions containing the same and methods of use thereof for the treatment of autoimmune disease.

10 Claims, No Drawings

IMIDAZOAZEPINONE COMPOUNDS

RELATED APPLICATIONS

This application is a 35 U.S.C. §371 national phase application of PCT Application PCT/US2007/012298, filed May 24, 2007, and published in English on Dec. 6, 2007, as International Publication No. WO 2007/139833, and which claims the benefit under 35 U.S.C. §119(e) of U.S. Provisional Patent Application Ser. No. 60/808,770, filed May 26, 2006, the disclosure of each of which is incorporated herein by reference in its entirety.

BACKGROUND OF THE INVENTION

Upon encountering antigen, naive CD4+ T helper precursor (Thp) cells are differentiated into two distinct subsets, Type 1 T helper (Th1) and Type 2 T helper (Th2). These differentiated Th cells are defined both by their distinct functional abilities and by unique cytokine profiles. Specifically, Th1 cells produce interferon-gamma, interleukin (IL)-2, and tumor necrosis factor (TNF)-beta, which activate macrophages and are responsible for cell-mediated immunity and phagocyte-dependent protective responses. In contrast, Th2 cells are known to produce IL-4, IL-5, IL-6, IL-9, IL-10 and IL-13, which are responsible for strong antibody production, eosinophil activation, and inhibition of several macrophage functions, thus providing phagocyte-independent protective responses. Accordingly, Th1 and Th2 cells are associated with different immunopathological responses.

In addition, the development of each type of Th cell is mediated by a different cytokine pathway. Specifically, it has been shown that IL-4 promotes Th2 differentiation and simultaneously blocks Th1 development. In contrast, IL-12, IL-18 and IFN-gamma are the cytokines critical for the development of Th1 cells. Accordingly, the cytokines themselves form a positive and negative feedback system that drives Th polarization and keeps a balance between Th1 and Th2.

Th1 cells are involved in the pathogenesis of a variety of organ-specific autoimmune disorders, Crohn's disease, *Helicobacter pylori*-induced peptic ulcer, acute kidney allograft rejection, and unexplained recurrent abortions. In contrast, allergen-specific Th2 responses are responsible for atopic disorders in genetically susceptible individuals. Moreover, Th2 responses against still unknown antigens predominate in Omenn's syndrome, idiopathic pulmonary fibrosis, and progressive systemic sclerosis.

There remains a high unmet medical need to develop new therapeutic treatments that are useful in treating the various conditions associated with imbalanced Th1/Th2 cellular differentiation. For many of these conditions the currently available treatment options are inadequate. Accordingly, the Th1/Th2 paradigm provides the rationale for the development of strategies for the therapy of allergic and autoimmune disorders.

SUMMARY OF THE INVENTION

As described herein, the present invention provides compounds of formula I:

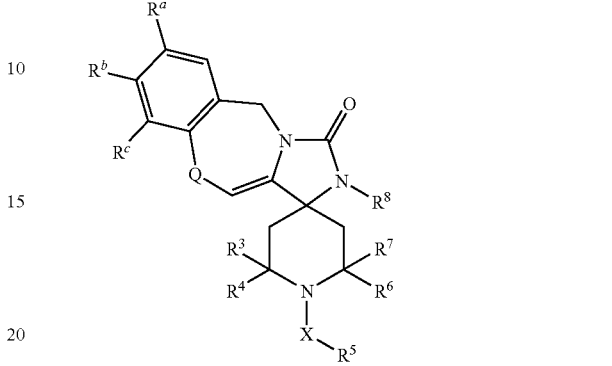

wherein:
Q is —C($R^1$)($R^2$)— or —CH═CH— (cis or trans);
$R^1$ and $R^2$ are independently selected from H, $C_{1-3}$ alkyl, $C_{2-4}$ alkenyl, or taken together are $C_{1-6}$ alkylidene or $C_{2-6}$ alkenylenidene;
each of $R^3$, $R^4$, $R^6$, and $R^7$ is independently selected from hydrogen and methyl;
X is methylene, ethylene, or propenylene;
$R^5$ is phenyl, quinolinyl, isoquinolinyl, indolyl, furyl, thienyl, pyrazolyl, quinoxalinyl, naphthyl, or pyrrolyl, and substituted with between 0 and 5 substituents independently selected from $C_{1-3}$ alkyl, $C_{1-3}$ alkoxy, hydroxyl, $C_{1-3}$ alkylthio, cyclopropyl, cyclopropylmethyl, and halo;
$R^8$ is H, methyl, ethyl, propenyl, ($C_{1-3}$ alkoxy)$C_{1-3}$ alkyl, ($C_{1-3}$ alkylthio)$C_{1-3}$ alkyl, $C_{1-3}$ hydroxyalkyl, phenyl, benzyl, furyl, pyrrolyl, imidazolyl, pyrazolyl, isothiazolyl, isooxazolyl, pyridyl, or thienyl;
   wherein $R^8$ is substituted with between 0 and 3 substituents independently selected from methyl, ethyl, halo, $C_{1-3}$ alkoxy, $C_{1-3}$ alkylthio, ($C_{1-3}$ alkoxy)$C_{1-3}$ alkyl, ($C_{1-3}$ alkylthio)$C_{1-3}$ alkyl, $C_{1-3}$ hydroxyalkyl, ($C_{1-3}$ mercaptoalkyl)phenyl, benzyl, furyl, imidazolyl, pyrazolyl, pyrrolyl, isothiazolyl, isooxazolyl, pyridyl, thienyl, pyranyl, dihydropyranyl, tetrahydropyranyl, and cyclopropyl; and
each of $R^a$, $R^b$, and $R^c$ is independently selected from hydrogen, hydroxyl, methoxy, benzyloxy, fluoro, chloro, amino, methylamino, dimethylamino, and phenoxy;
   or one pair selected from $R^a$ and $R^b$, and $R^b$ and $R^c$, taken together, is —O—(CH$_2$)—O— or —O—CH$_2$—CH$_2$—O—;
or a pharmaceutically acceptable salt, a $C_{1-6}$ alkyl ester or amide, or a $C_{2-6}$ alkenyl ester or amide thereof.

In other embodiments, the present invention provides a pharmaceutical composition comprising a compound of formula I or a subset or example thereof. In certain embodiments, the pharmaceutical composition is useful for an autoimmune disease (e.g., systemic lupus erythematosus, type 1 diabetes mellitus, psoriasis, atherosclerosis, etc.)

Other embodiments provide use of a compound of formula I, or a subset or example thereof, in the manufacture of a medicament. In certain embodiments, the present invention provides the use of a compound of formula I, or a subset or example thereof, in the manufacture of a medicament for the treatment of an autoimmune disease (e.g., systemic lupus erythematosus, type 1 diabetes mellitus, psoriasis, atherosclerosis, etc.)

Other aspects of the present invention are disclosed herein.

DETAILED DESCRIPTION OF CERTAIN EMBODIMENTS OF THE INVENTION

A. Definitions

Compounds of this invention include those described generally above, and are further illustrated by the embodiments, sub-embodiments, and species disclosed herein. As used herein, the following definitions shall apply unless otherwise indicated.

As described herein, compounds of the invention may optionally be substituted with one or more substituents, such as are illustrated generally above, or as exemplified by particular classes, subclasses, and species of the invention. In general, the term "substituted" refers to the replacement of hydrogen radicals in a given structure with the radical of a specified substituent. Unless otherwise indicated, a substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "alkyl" or "alkyl group," as used herein, means a straight-chain (i.e., unbranched), branched, or cyclic hydrocarbon chain that is completely saturated. In certain embodiments, alkyl groups contain 1 to 6 carbon atoms. In other embodiments, alkyl groups contain 1 to 3 carbon atoms. In still other embodiments, alkyl groups contain 2-3 carbon atoms, and in yet other embodiments alkyl groups contain 1-2 carbon atoms. In certain embodiments, the term "alkyl" or "alkyl group" refers to a cycloalkyl group, also known as carbocycle. Exemplary $C_{1-3}$ alkyl groups include methyl, ethyl, propyl, isopropyl, and cyclopropyl.

The term "alkenyl" or "alkenyl group," as used herein, refers to a straight-chain (i.e., unbranched), branched, or cyclic hydrocarbon chain that has one or more double bonds. In certain embodiments, alkenyl groups contain 2-4 carbon atoms. In still other embodiments, alkenyl groups contain 3-4 carbon atoms, and in yet other embodiments alkenyl groups contain 2-3 carbon atoms. According to another aspect, the term "alkenyl" refers to a straight chain hydrocarbon having two double bonds, also referred to as "diene." In other embodiments, the term "alkenyl" or "alkenyl group" refers to a cycloalkenyl group. Exemplary $C_{2-4}$ alkenyl groups include —CH=CH$_2$, —CH$_2$CH=CH$_2$ (also referred to as allyl), —CH=CHCH$_3$, —CH$_2$CH$_2$CH=CH$_2$, —CH$_2$CH=CHCH$_3$, —CH=CH$_2$CH$_2$CH$_3$, —CH=CH$_2$CH=CH$_2$, and cyclobutenyl.

The term "alkoxy," or "alkylthio," as used herein, refers to an alkyl group, as previously defined, attached to the principal carbon chain through an oxygen ("alkoxy") or sulfur ("alkylthio") atom.

As used herein, the terms "methylene," "ethylene," and "propylene" refer to the bivalent moieties —CH$_2$—, —CH$_2$CH$_2$—, and —CH$_2$CH$_2$CH$_2$—, respectively.

As used herein, the terms "ethenylene," "propenylene," and "butenylene" refer to the bivalent moieties —CH=CH—, —CH=CHCH$_2$—, —CH$_2$CH=CH—, —CH=CHCH$_2$CH$_2$—, —CH$_2$CH=CH$_2$CH$_2$—, and —CH$_2$CH$_2$CH=CH—, where each ethenylene, propenylene, and butenylene group can be in the cis or trans configuration. In certain embodiments, an ethenylene, propenylene, or butenylene group can be in the trans configuration.

As used herein, the term "alkylidene" refers to a bivalent hydrocarbon group formed by mono or dialkyl substitution of methylene. In certain embodiments, an alkylidene group has 1-6 carbon atoms. In other embodiments, an alkylidene group has 2-6, 1-5, 2-4, or 1-3 carbon atoms. Such groups include propylidene (CH$_3$CH$_2$CH=), ethylidene (CH$_3$CH=), and isopropylidene (CH$_3$(CH$_3$)CH=), and the like.

As used herein, the term "alkenylidene" refers to a bivalent hydrocarbon group having one or more double bonds formed by mono or dialkenyl substitution of methylene. In certain embodiments, an alkenylidene group has 2-6 carbon atoms. In other embodiments, an alkenylidene group has 2-6, 2-5, 2-4, or 2-3 carbon atoms. According to one aspect, an alkenylidene has two double bonds. Exemplary alkenylidene groups include CH$_3$CH=C=, CH$_2$=CHCH=, CH$_2$=CHCH$_2$CH=, and CH$_2$=CHCH$_2$CH=CHCH=.

As used herein, the term "$C_{1-6}$ alkyl ester or amide" refers to a $C_{1-6}$ alkyl ester or a $C_{1-6}$ alkyl amide where each $C_{1-6}$ alkyl group is as defined above. Such $C_{1-6}$ alkyl ester groups are of the formula ($C_{1-6}$ alkyl)OC(=O)— or ($C_{1-6}$ alkyl)C(=O)O—. Such C $C_{1-6}$ alkyl amide groups are of the formula ($C_{1-6}$ alkyl)NHC(=O)— or ($C_{1-6}$ alkyl)C(=O)NH—.

As used herein, the term "$C_{2-6}$ alkenyl ester or amide" refers to a $C_{2-6}$ alkenyl ester or a $C_{2-6}$ alkenyl amide where each $C_{2-6}$ alkenyl group is as defined above. Such $C_{2-6}$ alkenyl ester groups are of the formula ($C_{2-6}$ alkenyl)OC(=O)— or ($C_{2-6}$ alkenyl)C(=O)O—. Such $C_{2-6}$ alkenyl amide groups are of the formula ($C_{2-6}$ alkenyl)NHC(=O)— or ($C_{2-6}$ alkenyl)C(=O)NH—.

Unless indicated otherwise, nomenclature used to describe chemical groups or moieties as used herein follow the convention where, reading the name from left to right, the point of attachment to the rest of the molecule is at the right-hand side of the name. For example, the group "($C_{1-3}$ alkoxy)$C_{1-3}$ alkyl," is attached to the rest of the molecule at the alkyl end. Further examples include methoxyethyl, where the point of attachment is at the ethyl end, and methylamino, where the point of attachment is at the amine end.

Unless indicated otherwise, where a bivalent group is described by its chemical formula, including two terminal bond moieties indicated by "—," it will be understood that the attachment is read from left to right. By way of example, when X is —CH$_2$CH=CH—, X is attached to the nitrogen of the hydantoin core at the left-hand side methylene and X is attached to $R^5$ at the right-hand side methyne.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. In certain embodiments, when the Q group of formula I comprises a double bond, that double bond can be in the cis (E) or trans (Z) conformation. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

As used herein, the terms "treatment," "treat," and "treating" refer to reversing, alleviating, delaying the onset of, inhibiting the progress of, or preventing a disease or disorder as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

B. Compounds

In one embodiment, the present invention provides a compound of formula I:

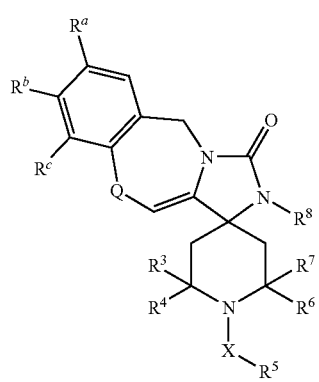

I wherein:
Q is —C($R^1$)($R^2$)— or —CH═CH— (cis or trans);
$R^1$ and $R^2$ are independently selected from H, $C_{1-3}$ alkyl, $C_{2-4}$ alkenyl, or taken together are $C_{1-6}$ alkylidene or $C_{2-6}$ alkenylenidene;
each of $R^3$, $R^4$, $R^6$, and $R^7$ is independently selected from hydrogen and methyl;
X is methylene, ethylene, or propenylene;
$R^5$ is phenyl, quinolinyl, isoquinolinyl, indolyl, furyl, thienyl, pyrazolyl, quinoxalinyl, naphthyl, or pyrrolyl, and substituted with between 0 and 5 substituents independently selected from $C_{1-3}$ alkyl, $C_{1-3}$ alkoxy, hydroxyl, $C_{1-3}$ alkylthio, cyclopropyl, cyclopropylmethyl, and halo;
$R^8$ is H, methyl, ethyl, propenyl, ($C_{1-3}$ alkoxy)$C_{1-3}$ alkyl, ($C_{1-3}$ alkylthio)$C_{1-3}$ alkyl, $C_{1-3}$ hydroxyalkyl, phenyl, benzyl, furyl, pyrrolyl, imidazolyl, pyrazolyl, isothiazolyl, isooxazolyl, pyridyl, and thienyl;

wherein $R^8$ is substituted with between 0 and 3 substituents independently selected from methyl, ethyl, halo, $C_{1-3}$ alkoxy, $C_{1-3}$ alkylthio, ($C_{1-3}$ alkoxy)$C_{1-3}$ alkyl, ($C_{1-3}$ alkylthio)$C_{1-3}$ alkyl, $C_{1-3}$ hydroxyalkyl, ($C_{1-3}$ mercaptoalkyl)phenyl, benzyl, furyl, imidazolyl, pyrazolyl, pyrrolyl, isothiazolyl, isooxazolyl, pyridyl, thienyl, pyranyl, dihydropyranyl, tetrahydropyranyl, and cyclopropyl; and
each of $R^a$, $R^b$, and $R^c$ is independently selected from hydrogen, hydroxyl, methoxy, benzyloxy, fluoro, chloro, amino, methylamino, dimethylamino, and phenoxy;
or one pair selected from $R^a$ and $R^b$, and $R^b$ and $R^c$, taken together, is —O—($CH_2$)—O— or —O—$CH_2$—$CH_2$—O—;
or a pharmaceutically acceptable salt, a $C_{1-6}$ alkyl ester or amide, or a $C_{2-6}$ alkenyl ester or amide thereof.

In certain embodiments, Q is —C($R^1$)($R^2$)—, wherein $R^1$ and $R^2$ are independently selected from H, methyl, ethyl, or taken together are $CH_2$═, allylidene, propylidene, propenylidene, or ethylidene. In other embodiments, $R^1$ and $R^2$ are independently selected from H and methyl, or taken together are $CH_2$═. According to another embodiment, $R^1$ and $R^2$ are independently selected from H, methyl, ethyl, or taken together are propylidene, allylidene, or $CH_2$═. In certain embodiments, each of $R^1$ and $R^2$ is independently selected from H, methyl, and ethyl. In other embodiments, one of $R^1$ and $R^2$ is H, and the other is methyl or ethyl. In still other embodiments, one of $R^1$ and $R^2$ is methyl and the other is H. Yet another aspect provides a compound of formula I wherein one of $R^1$ and $R^2$ is H. According to yet another embodiment, $R^1$ and $R^2$ taken together are propylidene, vinylidene, or $CH_2$═.

As defined generally above, X is methylene, ethylene, or propenylene. In certain embodiments, X is methylene or ethylene. In other embodiments, X is —$CH_2CH$═CH— in the trans configuration.

In certain embodiments, each of $R^3$, $R^4$, $R^6$, and $R^7$ is hydrogen.

According to one embodiment, $R^5$ is phenyl, quinolinyl, isoquinolinyl, indolyl, quinoxalinyl, or naphthyl, and substituted with between 0 and 3 substituents independently selected from methyl, methoxy, hydroxyl, bromo, fluoro, and chloro. According to another embodiment, $R^5$ is phenyl, quinolinyl, isoquinolinyl, indolyl, quinoxalinyl, or naphthyl, and substituted with between 0 and 3 substituents independently selected from hydrogen, fluoro, methyl, methoxy, hydroxyl, and bromo. In certain embodiments, $R^5$ is phenyl, quinolinyl, isoquinolinyl, indolyl, furyl, thienyl, pyrazolyl, quinoxalinyl, or naphthyl, and substituted with between 0 and 3 substituents independently selected from methyl, methoxy, fluoro, and bromo. In other embodiments, $R^5$ is phenyl, 4-quinolinyl, 5-quinolinyl, 8-quinolinyl, 5-isoquinolinyl, 3-indolyl, N-methyl-3-indolyl, 5-quinoxalinyl, 1-naphthyl, or 2-naphthyl, and substituted or further substituted with between 0 and 3 substituents independently selected from methyl, methoxy, and bromo. In still other embodiments, $R^5$ is phenyl, having the following substituents: fluoro, methyl or hydroxyl at the 2-position; hydrogen, methyl, or methoxy at the 3-position; and hydrogen, methyl, or methoxy at the 5-position. According to another aspect, $R^5$ is 2-fluoro-3,5-dimethylphenyl, 2-fluoro-3,5-dimethoxyphenyl, 3,5-dimethylphenyl, 2-hydroxy-3,5-dimethoxyphenyl, 2,3-dimethyl, or 2-methyl-3,5-dimethoxyphenyl.

According to one embodiment, $R^8$ is H, methyl, ethyl, methoxyethyl, methylthioethyl, hydroxyethyl, hydroxylpropyl, benzyl, or phenyl, optionally substituted. According to another embodiment, $R^8$ is H, methyl, ethyl, hydroxyethyl, benzyl, or phenyl; wherein phenyl is optionally substituted with pyrrolyl or pyrazolyl. In certain embodiments, $R^8$ is benzyl, phenyl, (pyrrolyl)phenyl, or (pyrazolyl)phenyl. In other embodiments, $R^8$ is H, methyl, ethyl, hydroxyethyl, or methoxyethyl. In still other embodiments, $R^8$ is methyl, ethyl, methoxy, ethyl, or hydroxyethyl.

In certain embodiments, each of $R^a$, $R^b$, and $R^c$ is independently selected from hydrogen, hydroxyl, methoxy, benzyloxy, fluoro, and chloro. In other embodiments, each of $R^a$, $R^b$, and $R^c$ is independently selected from hydrogen, methoxy, and fluoro. In still other embodiments, $R^c$ is methoxy or fluoro. According to another embodiment, $R^a$ and $R^c$ are methoxy or fluoro.

According to another aspect, the present invention provides a compound of formula I, wherein:
Q is —C($R^1$)($R^2$)—;
$R^1$ and $R^2$ are independently selected from H, methyl, ethyl, or taken together are $CH_2$=, allylidene, propylidene, propenylidene, or ethylidene;
each of $R^3$, $R^4$, $R^6$, and $R^7$ is hydrogen;
X is methylene, ethylene, or propenylene;
$R^5$ is phenyl, quinolinyl, isoquinolinyl, indolyl, quinoxalinyl, or naphthyl, and substituted with between 0 and 3 substituents independently selected from methyl, methoxy, hydroxyl, bromo, fluoro, and chloro;
$R^8$ is H, methyl, ethyl, methoxyethyl, methylthioethyl, hydroxyethyl, hydroxylpropyl, benzyl, or phenyl, optionally substituted; and
each of $R^a$, $R^b$, and $R^c$ is independently selected from hydrogen, hydroxyl, methoxy, benzyloxy, fluoro, and chloro.

According to another aspect, the present invention provides a compound of formula I wherein:
Q is —C($R^1$)($R^2$)—;
$R^1$ and $R^2$ are independently selected from H and methyl, or taken together are $CH_2$=,
each of $R^3$, $R^4$, $R^6$, and $R^7$ is hydrogen;
X is methylene, ethylene, or propenylene;
$R^5$ is phenyl, quinolinyl, isoquinolinyl, indolyl, quinoxalinyl, or naphthyl, and substituted with between 0 and 3 substituents independently selected from hydrogen, fluoro, methyl, methoxy, hydroxyl, and bromo;
$R^8$ is H, methyl, ethyl, hydroxyethyl, benzyl, or phenyl; wherein phenyl is optionally substituted with pyrrolyl or pyrazolyl; and
each of $R^a$, $R^b$, and $R^c$ is independently selected from hydrogen, methoxy, and fluoro.

Yet another aspect of the present invention provides a compound of formula I, wherein:
Q is —C($R^1$)($R^2$)—;
$R^1$ and $R^2$ are independently selected from H, methyl, ethyl, or taken together are propylidene, allylidene, or $CH_2$=;
each of $R^3$, $R^4$, $R^6$, and $R^7$ is hydrogen;
X is methylene or ethylene;
$R^5$ is phenyl, quinolinyl, isoquinolinyl, indolyl, furyl, thienyl, pyrazolyl, quinoxalinyl, or naphthyl, and substituted with between 0 and 3 substituents independently selected from methyl, methoxy, fluoro, and bromo; and
$R^8$ is H, methyl, ethyl, hydroxyethyl, benzyl, or phenyl; wherein phenyl is optionally substituted with pyrrolyl or pyrazolyl.

In certain embodiments, the present invention provides a compound of formula I, wherein:
Q is —C($R^1$)($R^2$);
one of $R^1$ and $R^2$ is H and the other is methyl or ethyl;
each of $R^3$, $R^4$, $R^6$, and $R^7$ is hydrogen;

$R^5$ is phenyl, having the following substituents: fluoro, methyl or hydroxyl at the 2-position; hydrogen, methyl, or methoxy at the 3-position; and hydrogen, methyl, or methoxy at the 5-position; and
$R^8$ is methyl, ethyl, methoxy, ethyl, or hydroxyethyl.

It will be appreciated that all embodiments, classes and subclasses described above and herein are contemplated both singly and in combination.

Exemplary compounds of formula I are set forth in the Examples section and in Tables 1-2, below. Thus particular examples of the compounds of the invention include, but are not limited to:

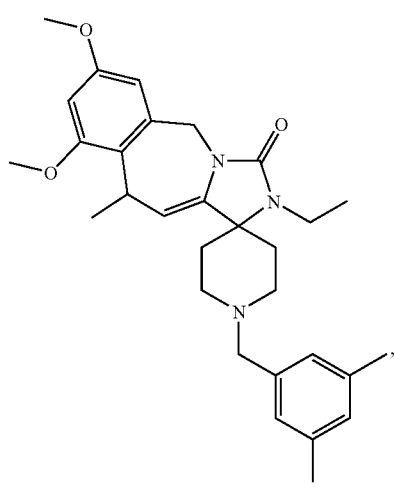

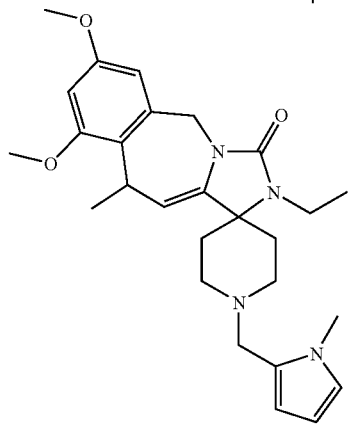

and pharmaceutically acceptable salts thereof.

C. Uses, Formulation and Administration

Pharmaceutically acceptable compositions. The compounds and compositions described herein are generally useful for the inhibition of Th1 cell formation. In particular, these compounds, and compositions thereof, are useful as inhibitors, directly or indirectly, of the T-bet signalling pathway. Thus, the compounds and compositions of the invention are therefore also particularly suited for the treatment of diseases and disease symptoms that are mediated by Th1 cells and/or T-bet signalling pathway.

In one particular embodiment, the compounds and compositions of the invention are inhibitors, directly or indirectly, of the T-bet signalling pathway, and thus the compounds and compositions are particularly useful for treating or lessening the severity of disease or disease symptoms associated with the T-bet signalling pathway.

The term "patient" or "subject," as used herein, means an animal, preferably a mammal, and most preferably a human, patient or subject.

In certain embodiments, the present invention provides a composition comprising a compound of formula I. In other embodiments, the present invention provides a composition comprising any of the compounds set forth in Tables 1 and 2. According to another aspect, the present invention provides a composition comprising a compound selected from ER-819724, ER-819755, ER-819750, ER-819749, ER-819735. According to yet another aspect, the present invention provides a composition comprising a compound selected from ER-819543, ER-819549, ER-819543, ER-819701, ER-819544, ER-819594, ER-819647, ER-819657, ER-819659, and ER-819592. In other embodiments, the present invention provides a composition comprising a compound selected from ER-819595, ER-819597, ER-819641, ER-819673, ER-819651, ER-819583, ER-819604, ER-819593, ER-819658, and ER-819648. In still other embodiments, the present invention provides a composition comprising a compound selected from ER-819602, ER-819689, ER-819646, ER-819655, ER-819703, ER-819667, ER-819601, ER-819605, ER-819652, ER-819688, ER-819603, ER-819642, and ER-819628. Yet another embodiment provides a composition comprising a compound selected from ER 819-891, ER-ER-819772, ER-819771, ER-819770, ER-819769, ER-819768, and ER-819767. In certain embodiments, the present invention provides a composition comprising a compound selected from ER-819556, ER-819557, ER-819558, and ER-819752. Yet another embodiment provides a composition comprising a compound selected from ER-819877, ER-819878, ER-819879, ER-819882, and ER-819763.

The term "pharmaceutically acceptable carrier, adjuvant, or vehicle" refers to a nontoxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, cyclodextrins, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+($C_{1-4}$ alkyl)$_4$ salts. This invention also envisions the quaternization of any basic nitrogen-containing groups of the compounds disclosed herein. Water- or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspensions. These suspensions may be formulated according to techniques known in the art using suitable dispersing or wetting agents and suspending agents. The sterile injectable preparation may also be a sterile injectable solution or suspension in a nontoxic, parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural, pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bio-availability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, and the particular mode of administration. Preferably, the compositions should be formulated so that a dosage of between 0.01-100 mg/kg body weight/day of the inhibitor can be administered to a patient receiving these compositions. In certain embodiments, the compositions of the present invention provide a dosage of between 0.01 mg and 50 mg is provided. In other embodiments, a dosage of between 0.1 and 25 mg or between 5 mg and 40 mg is provided.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

C. Uses of Compounds and Pharmaceutically Acceptable Compositions

T-bet (T-box expressed in T cells) is a Th1 specific transcription factor that is a key regulator of the Th1/Th2 balance. See S. J. Szabo, et al., *Cell*, 100:655-669 (2000). T-bet is selectively induced in Th1 cells and can transactivate the interferon-gamma gene, induce interferon-gamma production, redirect polarized Th2 cells into the Th1 pathway. T-bet also controls IFN-gamma production in CD8+ T cells, as well as in cells of the innate immune system, e.g., NK cells and dendritic cells. Accordingly, direct or indirect inhibitors of the T-bet signalling pathway (including compounds that inhibit T-bet expression) are therapeutically useful in balancing over-active Th1 responses, and therefore may be of value in treating Th1-mediated diseases, such as rheumatoid arthritis and multiple sclerosis.

According to one embodiment, the invention relates to a method of inhibiting the formation of Th1 cells in a biological sample comprising the step of contacting said biological sample with a compound of this invention, or a composition comprising said compound.

According to another embodiment, the invention relates to a method of directly or indirectly inhibiting activity of the T-bet signalling pathway in a biological sample comprising the step of contacting said biological sample with a compound of this invention, or a composition comprising said compound.

The term "biological sample," as used herein, includes, without limitation, cell cultures or extracts thereof; biopsied material obtained from a mammal or extracts thereof; and blood, saliva, urine, feces, semen, tears, or other body fluids or extracts thereof.

Active compounds of the present invention may be administered to patients or subjects to treat a variety of different conditions, particularly patients or subjects afflicted with:

(a) systemic lupus erythematosus (see, e.g., T-bet regulates IgG class switching and pathogenic auto Ab production, *Proc. Natl. Acad. Sci. USA* 99(8): 5545-50 (2002); Imbalance of Th1/Th2 transcription factors in patients with lupus nephritis, *Rheumatology (Oxford)* 45(8): 951-7 (2006));

(b) type I diabetes (see, e.g., Identification of a novel type 1 diabetes susceptibility gene, T-bet, *Human Genetics* 111(3): 177-84 (2004); T-bet controls autoaggressive CD8 lymphocyte response in type I diabetes, *J. Exp. Med.* 199(8): 1153-62 (2004));

(c) psoriasis (see, e.g., *J. Mol. Med.* 81(8): 471-80 (2003)); and (d) atherosclerosis (see, e.g., *Proc. Natl. Acad. Sci. USA* 102(5): 1596-601 (2005)).

In order that the invention described herein may be more fully understood, the following examples are set forth. It should be understood that these examples are for illustrative purposes only and are not to be construed as limiting this invention in any manner. For example, in the claims below, where compounds are identified by a number "ER-xxxxxx" herein, the compound is intended to be inclusive of that compound as both a free base (or salt-free) and any pharmaceutically acceptable salts thereof (e.g., as identified in the definitions above), even if that compound is specified as "salt free" or as a particular salt in the Examples below. Additionally, where structures of compounds are depicted in connection with a number "ER-xxxxxx" herein, and that structure contains a methyl group depicted by a sinusoidal or "wavy" line, that the compound is intended to be inclusive of that compound as both a racemic mixture and enantiomerically pure compounds.

EXAMPLES 1-32

Chemical Compounds

Microwave assisted reactions were carried out using an Emrys Liberator instrument supplied by Biotage Corporation. Solvent removal was carried out using either a Büchi rotary evaporator or a Genevac centrifugal evaporator. Analytical and preparative chromatography was carried out using a Waters autopurification instrument using reverse phase HPLC columns under either acidic, neutral, or basic conditions. Compounds were estimated to be >90% pure, as determined by area percent of ELSD chromatograms. NMR spectra were recorded using a Varian 300 MHz spectrometer.

General methods and experimentals for preparing compounds of the present invention are set forth below. In certain cases, a particular compound is described by way of example. However, it will be appreciated that in each case a series of compounds of the present invention were prepared in accordance with the schemes and experimentals described below.

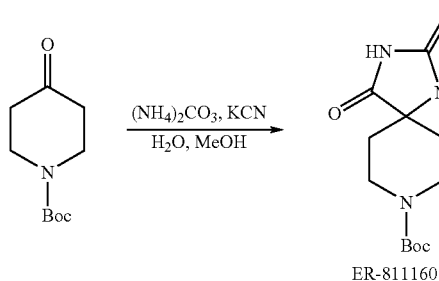

Scheme 1

ER-811160

ER-811160. As depicted in Scheme 1 above, a solution of potassium cyanide (22.5 g, 0.335 mol) in water (50 mL) was added dropwise over 5 minutes to a solution of 1-Boc-piperidone (32.48 g, 0.1598 mol) and ammonium carbonate (33.8 g, 0.351 mol) in water (90 mL) and methanol (110 mL). An off-white precipitate began to form soon after addition was complete. The reaction flask was sealed and the suspension stirred at room temperature for 72 hours. The resultant pale yellow precipitate was filtered and was washed with small portions of water to give ER-811160 (37.1 g, 86%) as a colorless solid.

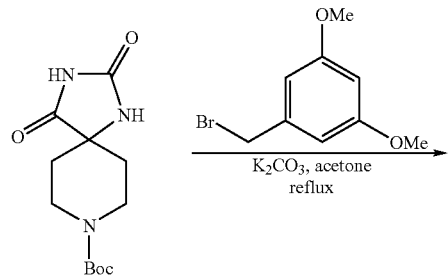

Scheme 2

ER-811160

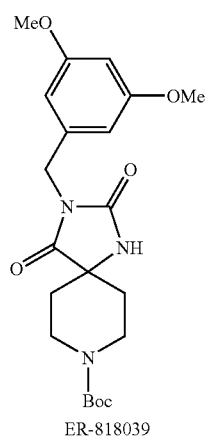

ER-818039

ER-818039. As depicted in Scheme 2 above, a suspension of ER-811160 (30.0 g, 0.111 mol), 3,5-dimethoxybenzyl bromide (30.9 g, 0.134 mol), and potassium carbonate (18.5 g, 0.134 mol) in acetone (555 mL) was heated under reflux overnight. The reaction solution was cooled to room temperature, filtered and concentrated in vacuo. The crude orange product was dissolved in a minimal amount of MTBE (250 mL). A small amount of hexanes was added (50 mL) and the product was allowed to precipitate out (2 hours) as a colorless solid which was isolated by vacuum filtration. The filter cake was washed with small amounts of MTBE, and dried in vacuo to provide ER-818039 (39.6 g, 85%).

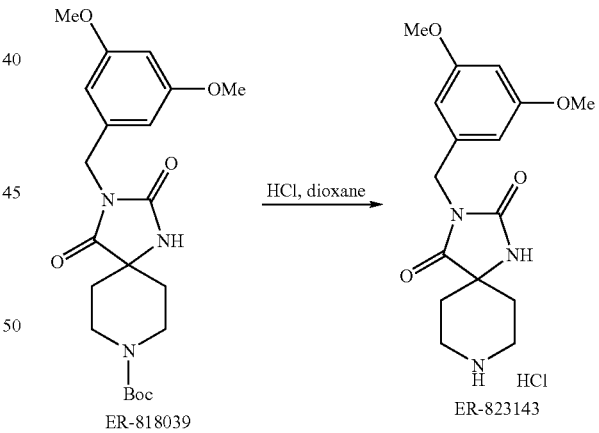

Scheme 3

ER-818039 → ER-823143

ER-823143. As depicted in Scheme 3 above, to a 1-neck round-bottom flask containing ER-818039 (2.15 g, 0.00512 mol) was slowly added a solution of 4N HCl in 1,4-Dioxane (3.8 mL, 0.049 mol). The starting material slowly dissolved over 20 minutes and a colorless precipitate formed after 30 minutes. MTBE (3 ml) was then added. After 2 hours, the reaction was filtered and washed with MTBE, which provided ER-823143 (1.81 g, 99%) as a colorless solid.

Scheme 4

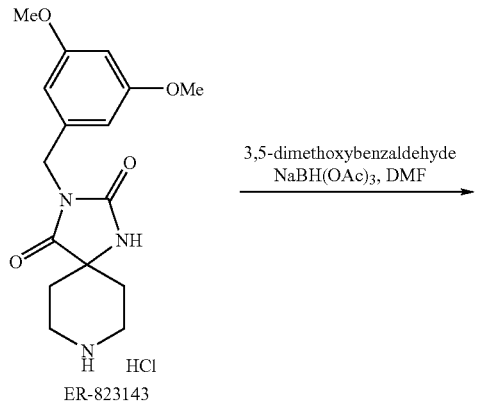

Scheme 5

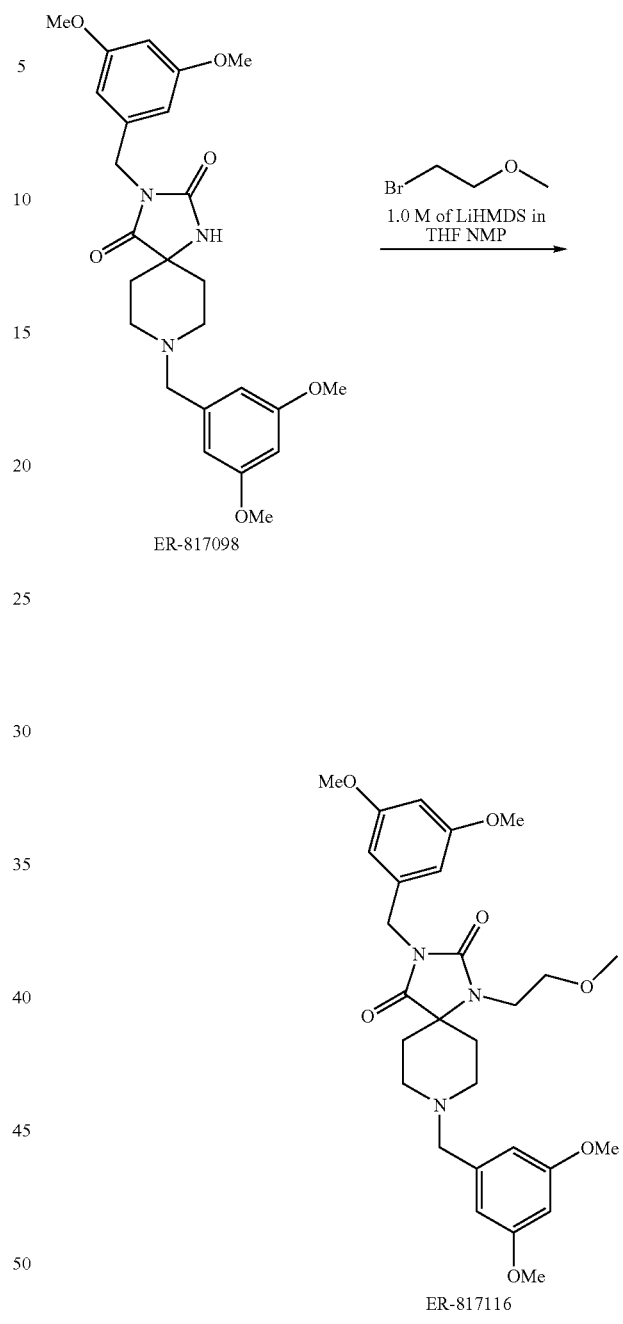

ER-817098: As depicted in Scheme 4 above, to a suspension of ER-823143 (41.5 mg, 0.000117 mol) and 4 Å molecular sieves in 1,2-dimethoxyethane (0.5 mL, 0.004 mol) under an atmosphere of nitrogen was added 3,5-dimethoxybenzaldehyde (21.3 mg, 0.000128 mol) followed by triethylamine (16.2 µL, 0.000117 mol). The reaction was stirred for 1 hour. Sodium triacetoxyborohydride (34.6 mg, 0.000163 mol) was added, and the reaction was stirred overnight. Flash chromatography using ethyl acetate as eluent yielded ER-817098 (45.3 mg, 83%) as a colorless solid.

ER-817116: As depicted in Scheme 5 above, to a solution of ER-817098-00 (50.0 mg, 0.000106 mol) and 1-bromo-2-methoxyethane (15.6 µL, 0.000160 mol) in N-methylpyrrolidinone (1.0 mL, 0.010 mol) was added 1.0 M lithium hexamethyldisilazide solution in tetrahydrofuran (0.16 mL). The temperature was increased to at 80° C. and the reaction mixture stirred overnight. The reaction mixture was cooled to room temperature, quenched with water and then extracted several times with MTBE. The MTBE extracts were combined and washed with water (2×) and brine (1×). The organic layer was dried over magnesium sulfate, filtered, and concentrated in vacuo. Flash chromatography using ethyl acetate as eluent provided ER-817116 (32.2 mg, 58%) as colorless oil.

Scheme 6

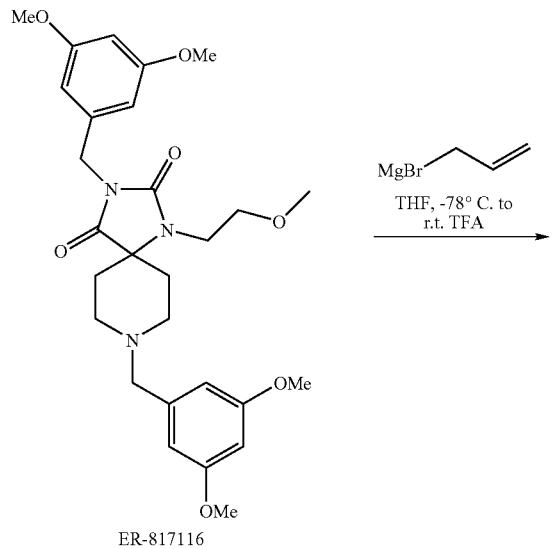

ER-817116

Scheme 7

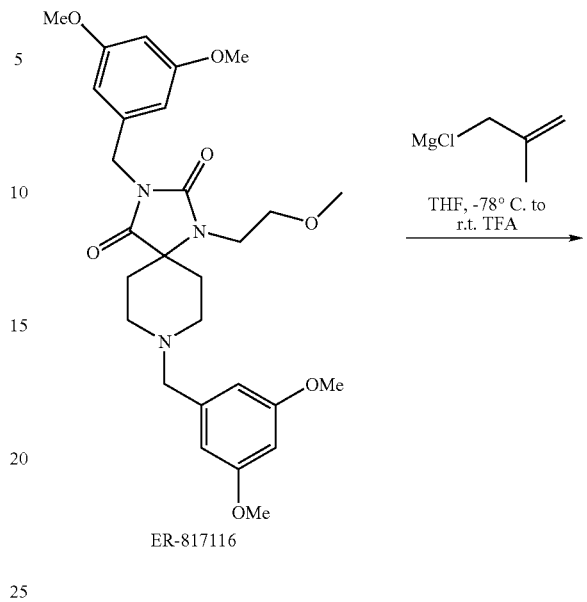

ER-817116

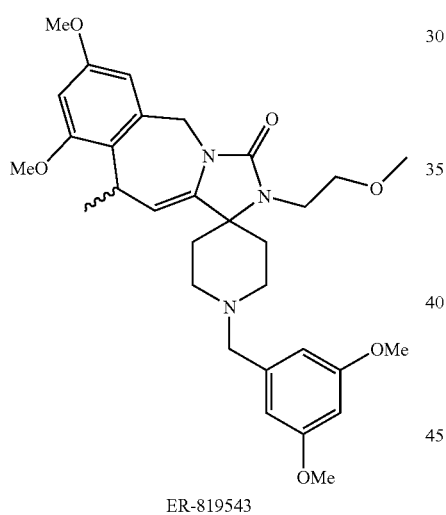

ER-819543

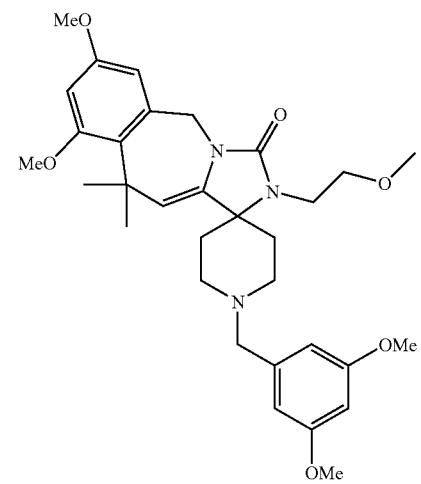

ER-819544

ER-819543: As depicted in Scheme 6 above, to a solution of ER-817116-00 (91.6 mg, 0.000174 mol) in tetrahydrofuran (1.8 mL, 0.022 mol) at −78° C. was slowly added a solution of 1.0 M allylmagnesium bromide in ether (0.35 mL). The reaction mixture was warmed to room temperature and stirred overnight. Mass spectroscopic analysis showed 25% conversion to product; consequently, the reaction mixture was re-cooled to −78° C. and an additional 1.35 mL of 1.0 M of allylmagnesium bromide in ether was added. The reaction mixture was warmed to room temperature and stirred for 4 hours. The reaction mixture was then cooled to 0° C. and was treated dropwise with trifluoroacetic acid (2.00 mL, 0.0260 mol) and then concentrated in vacuo. Triethylamine was then added to neutralize residual TFA. Ethyl acetate was added and the crude reaction product purified by flash chromatography (eluent: 100% Ethyl acetate) to provide ER-819543 (56.8 mg, 59%) as a colorless solid.

ER-819544: As depicted in Scheme 7 above, to a solution of ER-817116-00 (100.5 mg, 0.0001905 mol) in tetrahydrofuran (1.9 mL, 0.023 mol) at −78° C. was slowly added a 0.5 M solution of 2-methylallylmagnesium chloride in tetrahydrofuran (800 μL). The reaction mixture was warmed to room temperature and stirred for 6 hours. The reaction mixture was cooled to 0° C., treated dropwise with trifluoroacetic acid (1.00 mL, 0.0130 mol), and then concentrated in vacuo. Triethylamine was added to neutralize residual TFA. Ethyl acetate was added and the crude reaction product purified by flash chromatography using ethyl acetate as eluent to provide ER-819544 (66.2 mg, 61%) as a colorless solid.

Scheme 8

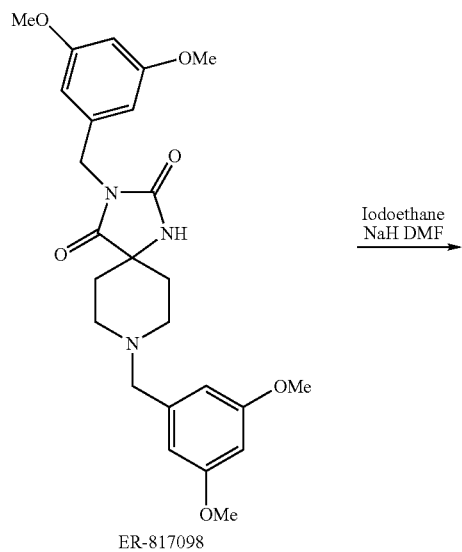

ER-817098

→ Iodoethane NaH DMF

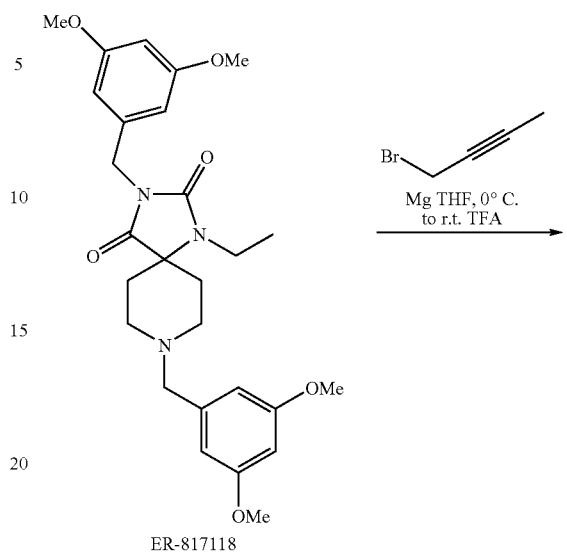

ER-817118

Scheme 9

ER-817118

$\xrightarrow[\text{Mg THF, 0° C.}]{\text{Br}\diagdown \diagup \diagdown \!\!\equiv\!\!\diagup}$ to r.t. TFA

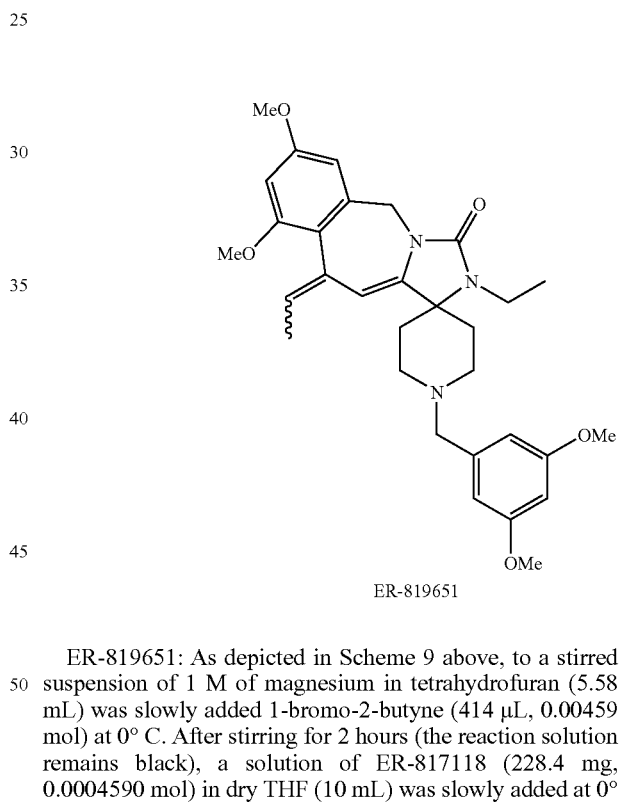

ER-819651

ER-817118: As depicted in Scheme 8 above, to a solution of ER-817098 (2.85 g, 0.00607 mol) in N,N-dimethylformamide (15 mL) was added sodium hydride (364 mg, 0.00910 mol) followed by iodoethane (758 µL, 0.00910 mol). The reaction mixture was stirred overnight. Water was very slowly added and the reaction mixture was extracted several times with MTBE. The MTBE extracts were combined and washed with water (2×) and brine (1×). The organic layer was dried over magnesium sulfate, filtered, and concentrated in vacuo. Flash chromatography using ethyl acetate as eluent provided ER-817098 (2.89 g, 96%) as a colorless oil.

ER-819651: As depicted in Scheme 9 above, to a stirred suspension of 1 M of magnesium in tetrahydrofuran (5.58 mL) was slowly added 1-bromo-2-butyne (414 µL, 0.00459 mol) at 0° C. After stirring for 2 hours (the reaction solution remains black), a solution of ER-817118 (228.4 mg, 0.0004590 mol) in dry THF (10 mL) was slowly added at 0° C. The reaction was warmed to room temperature and was stirred for 4 hours. The reaction mixture was then cooled to −78° C. and treated dropwise with trifluoroacetic acid (0.95 mL, 0.012 mol) to cause the solution to become clear. The reaction mixture was warmed to room temperature and stirred for 1 hour. The reaction mixture was concentrated in vacuo to dryness using a rotary evaporator with a water bath temperature of 40° C. The residual light brown solid was basified with triethylamine (clear solid) and purified by flash chromatography (eluent: 2% EtOH in methylene chloride) to provide impure ER-819651. Subsequent repurification by HPTLC (8% EtOH in Toluene) provided ER-819651 (128.8 mg, 53%) as a colorless solid.

Scheme 10

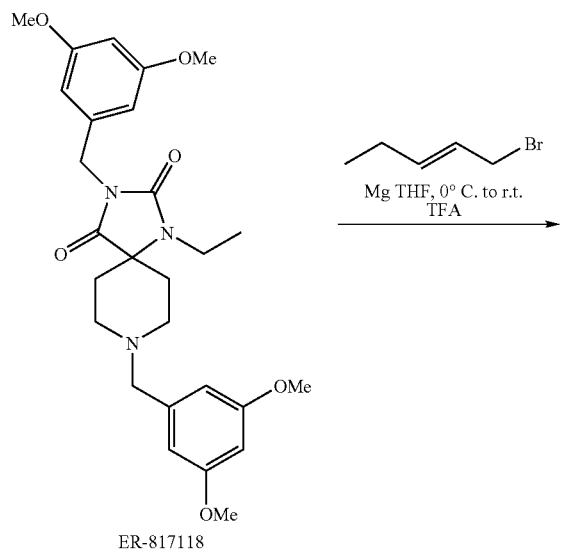

ER-817118

Scheme 11

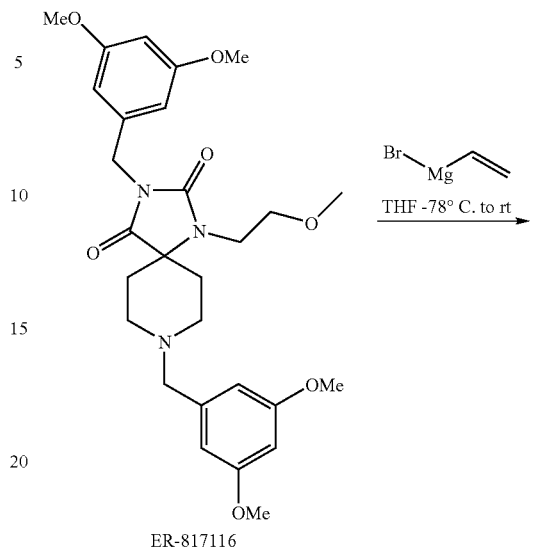

ER-817116

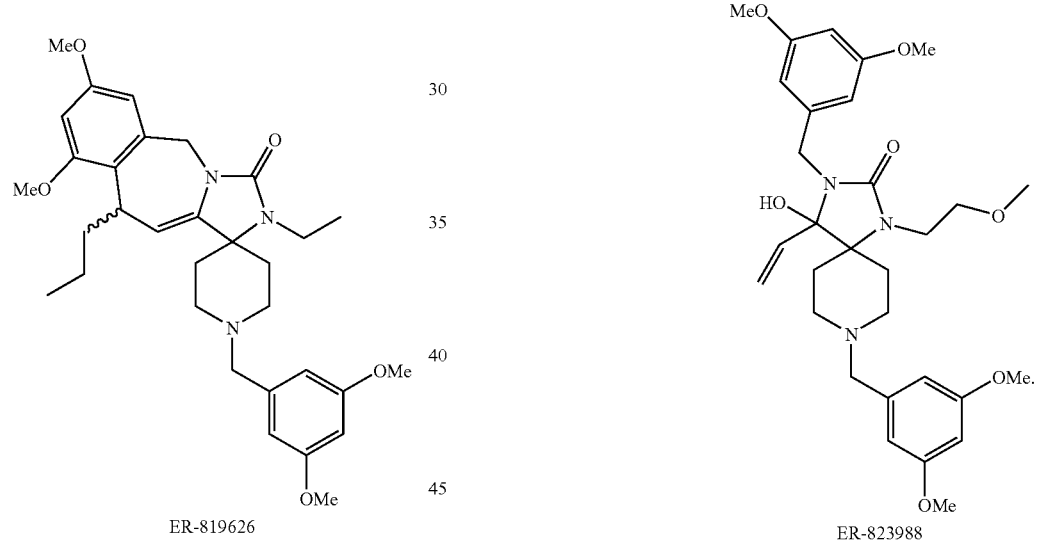

ER-819626

ER-823988

ER-819626: As depicted in Scheme 10 above, to a stirred suspension of 1 M of magnesium in tetrahydrofuran (4.990 mL) was slowly added 1-bromo-2-pentene (485.6 uL, mol) at 0° C. After stirring for 2 hours (the reaction solution remains black), a solution of ER-817118 (204.3 mg, 0.0004106 mol) in dry THF (10 mL) was slowly added at 0° C. The reaction mixture was warmed to room temperature and stirred for 4 hours (reaction solution remains black). The reaction was cooled to −78° C. and treated dropwise with trifluoroacetic acid (0.85 mL, 0.011 mol) to cause the reaction mixture to become clear. The reaction mixture was warmed to room temperature and stirred for 1 hour. The reaction mixture was concentrated in vacuo to dryness using a rotary evaporator with a water bath temperature of 40° C. The crude product (light brown solid) was basified with triethylamine (clear solid) and purified by flash chromatography (eluent: 2% EtOH in methylene chloride) to provide ER-819626 (110.2 mg, 49%) as a white solid.

ER-823988: As depicted in Scheme 11 above, to a solution of ER-817116 (1.006 g, 0.0019067 mol) in tetrahydrofuran (7.6 mL, 0.094 mol) was slowly added a 1.0 M solution of vinylmagnesium bromide in tetrahydrofuran (3.8 mL) at −78° C. The reaction mixture was warmed to room temperature and stirred for 1 hour. Mass spectroscopic analysis showed a significant amount of residual starting material; consequently, the reaction mixture was re-cooled to 0° C. and an additional 3.8 mL of 1.0 M vinylmagnesium bromide solution in tetrahydrofuran was added. The reaction mixture was stirred for 2 hours then quenched by dropwise addition of saturated aqueous ammonium hydroxide solution. The mixture was extracted several times with ethyl acetate. The organic extracts were combined and washed with water (2×) and brine. The organic layer was dried over magnesium sulfate, filtered, and concentrated in vacuo. Flash chromatography (eluent: 5% ethanol in ethyl acetate) provided ER-823988 (0.605 g, 57%) as a colorless solid.

Scheme 12

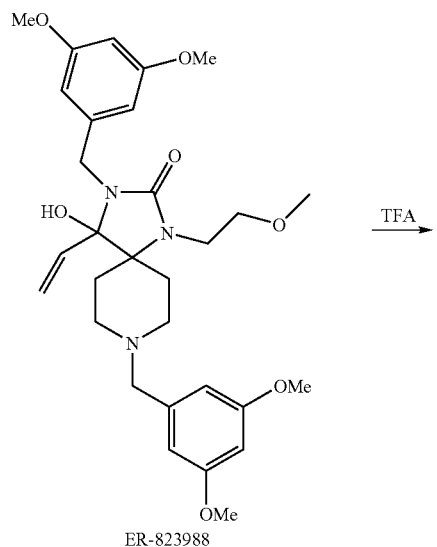

ER-823988

→ TFA →

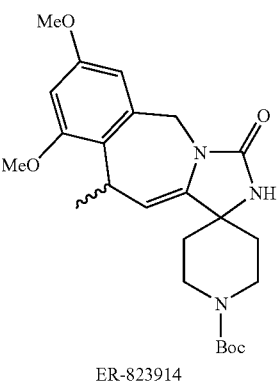

ER-819673

Scheme 13

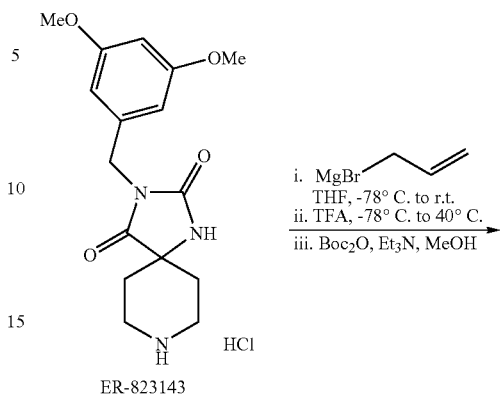

ER-823143 i. MgBr⁀/\/  
  THF, −78° C. to r.t.  
ii. TFA, −78° C. to 40° C.  
iii. Boc₂O, Et₃N, MeOH

→

ER-823914

ER-819673: As depicted in Scheme 12 above, ER-823988 (163.1 mg, 0.0002935 mol) was dissolved in trifluoroacetic acid (2.00 mL, 0.0260 mol) at room temperature. The reaction mixture was warmed to 40° C. and stirred for 2 hours then concentrated in vacuo. The residue was dissolved in a small amount of acetone and was treated with a small portion of potassium carbonate until basic. Flash chromatography (eluent: 2% ethanol in ethyl acetate) provided ER-819673 (0.101 g, 64%) as a colorless glassy solid.

ER-823914: As depicted in Scheme 13 above, to a solution of ER-823143 (5.03 g, 0.0141 mol) in tetrahydrofuran (30.0 mL, 0.370 mol) at −78° C. was slowly added a 1.0 M solution of allylmagnesium bromide in ether (71 mL). The reaction mixture was warmed to room temperature and stirred overnight. The reaction mixture was cooled to −78° C., treated dropwise with trifluoroacetic acid (21.8 mL, 0.283 mol), and then concentrated in vacuo to a small residual volume. Triethylamine was added to neutralize residual TFA and the mixture then concentrated in vacuo to dryness. The residual red oil was dissolved in methanol (138 mL, 3.41 mol) and treated with di-tert-butyldicarbonate (3.34 g, 0.0148 mol) followed by triethylamine (2.38 mL, 0.0169 mol) and stirred overnight at room temperature. The reaction mixture was concentrated in vacuo and purified by flash chromatography (eluent: 50% hexanes in ethyl acetate) to provide ER-823914 (3.25 g, 52%) as a colorless solid.

Scheme 14

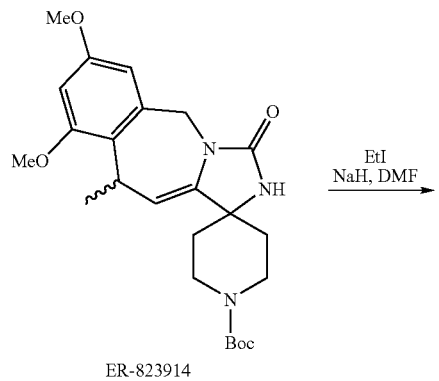
ER-823914

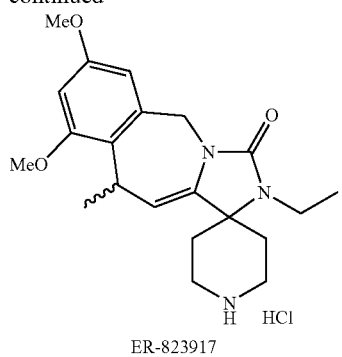
ER-823917

ER-823917: As depicted in Scheme 15 above, ER-823915 (799.2 mg, 0.001695 mol) was dissolved in a solution of 4 M hydrogen chloride in 1,4-dioxane (10 mL). The reaction mixture was stirred overnight and then concentrated in vacuo to provide ER-823917 (0.69 g, quantitative) as an orange solid.

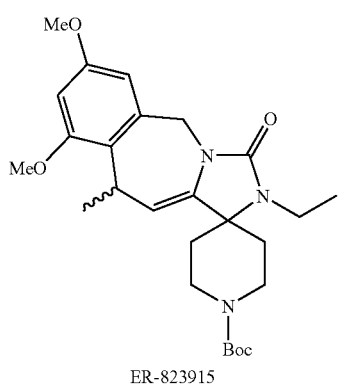
ER-823915

ER-823915: To a solution of ER-823914 (2.20 g, 0.00496 mol) in N,N-Dimethylformamide (12.4 mL, 0.160 mol) was added sodium hydride (298 mg, 0.00744 mol) followed by iodoethane (607 µL, 0.00744 mol). The reaction mixture was stirred overnight then quenched with water and extracted several times with MTBE. The MTBE extracts were combined and washed with water and brine. The organic layer was dried over magnesium sulfate, filtered, and concentrated in vacuo. Flash chromatography (eluent: 40% hexanes in ethyl acetate) provided ER-823915 (0.80 g, 34%) as a colorless foam.

Scheme 15

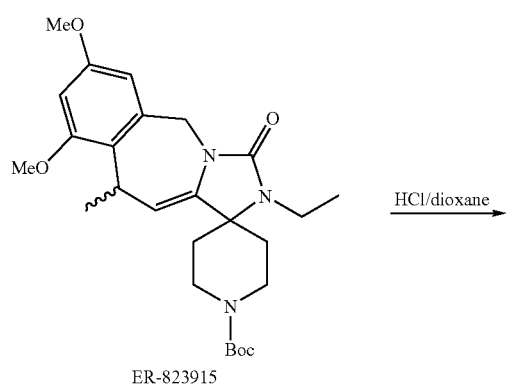
ER-823915

Scheme 16

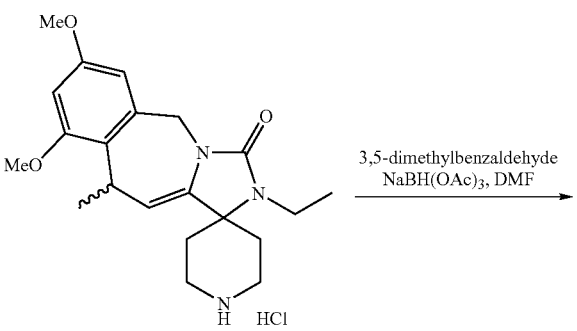
ER-823917

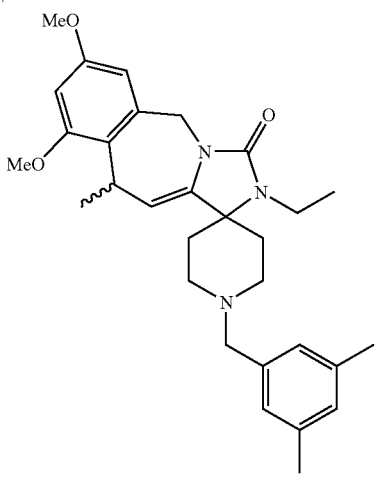
ER-819597

ER-819597: As depicted in Scheme 16 above, ER-823917 (100.0 mg, 0.0002451 mol), 4 Å molecular sieves, and 3,5-dimethylbenzaldehyde (50.9 mg, 0.000368 mol) were dissolved/suspended in N,N-dimethylformamide (1.0 mL, 0.013 mol). After stirring for 30 minutes, sodium triacetoxyborohydride (76.6 mg, 0.000343 mol) was added. The reaction mixture was stirred overnight. Water was added until a white precipitate formed. The precipitate was collected by filtration washing several times with water. The filtrate was then dried in vacuo to provide ER-819597 (108.0 mg, 90%) as a colorless solid.

ER-819689, ER-819688, ER-819604, ER-819595, ER-819594, ER-819593, ER-819592, ER-819582, and ER-819777 were prepared in substantially the same manner as for ER-819597. In some instances the desired product could be precipitated from the reaction mixture; in other cases the reaction mixture would be quenched with water then extracted with a suitable water-immiscible solvent, followed by chromatographic purification.

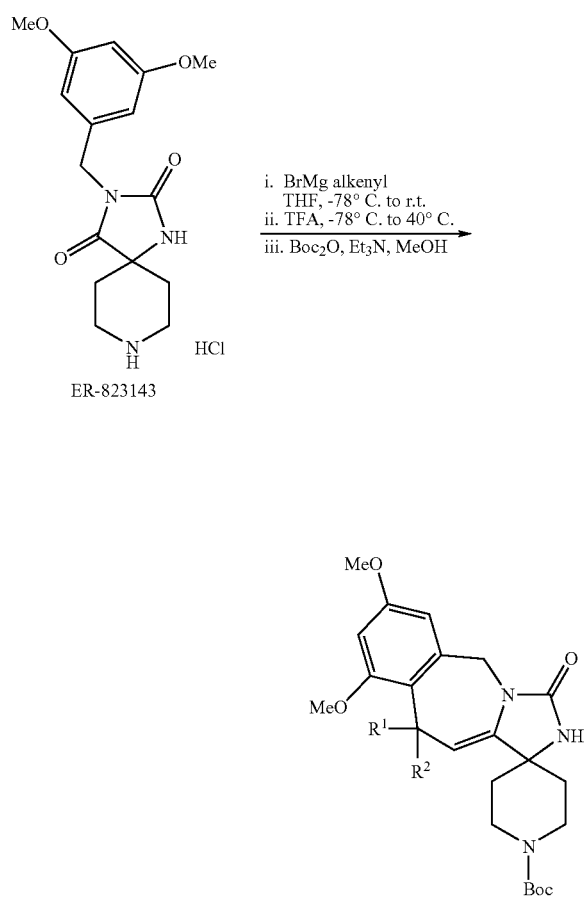

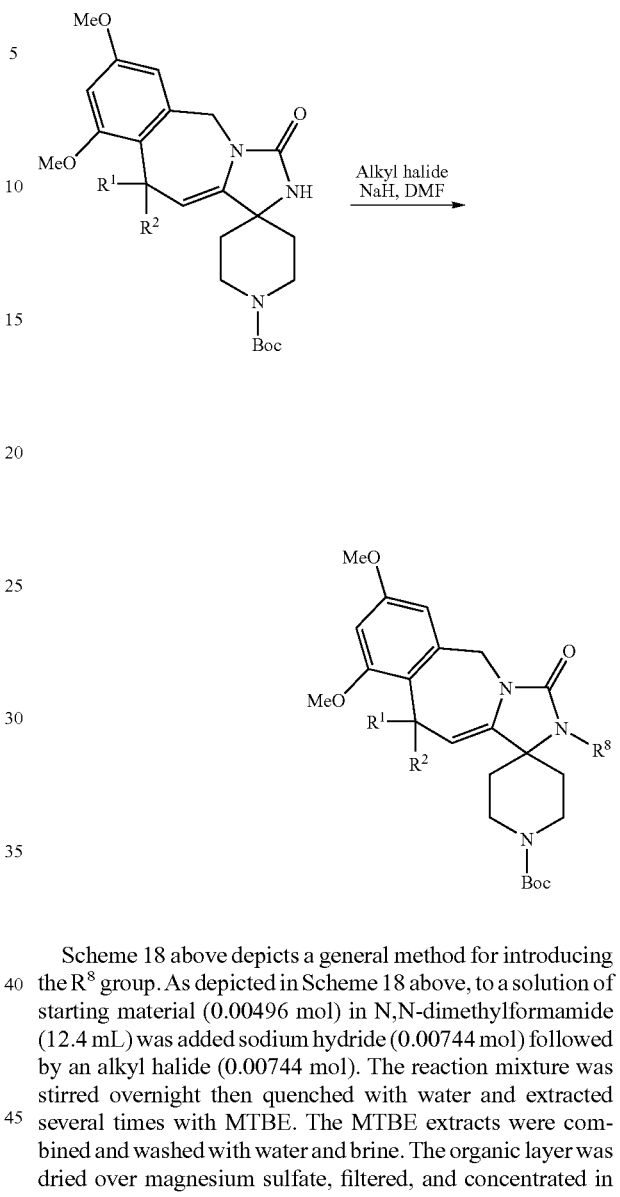

Scheme 17 above depicts a general cyclization method. As depicted in Scheme 17 above, to a solution of ER-823143. (0.0141 mol) in tetrahydrofuran (30.0 mL) at −78° C. was slowly added a 1.0 M solution of an alkenyl magnesium bromide in ether (71 mL). The reaction mixture was warmed to room temperature and stirred overnight. The reaction mixture was cooled to −78° C. and treated dropwise with trifluoroacetic acid (0.283 mol). The reaction solution was concentrated in vacuo to a small volume then treated with triethylamine to neutralize the residual TFA. The crude product was concentrated in vacuo to dryness. The resultant residue was then dissolved in methanol (138 mL) and treated with di-tert-butyldicarbonate (0.0148 mol) followed by triethylamine (0.0169 mol). The reaction mixture was stirred overnight then concentrated in vacuo. Purification by flash chromatography provided the desired product.

Scheme 18 above depicts a general method for introducing the $R^8$ group. As depicted in Scheme 18 above, to a solution of starting material (0.00496 mol) in N,N-dimethylformamide (12.4 mL) was added sodium hydride (0.00744 mol) followed by an alkyl halide (0.00744 mol). The reaction mixture was stirred overnight then quenched with water and extracted several times with MTBE. The MTBE extracts were combined and washed with water and brine. The organic layer was dried over magnesium sulfate, filtered, and concentrated in vacuo. Flash chromatography provided the desired product.

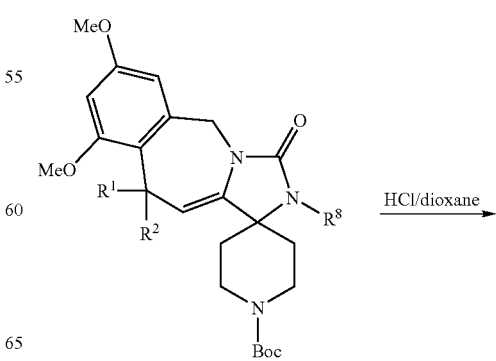

-continued

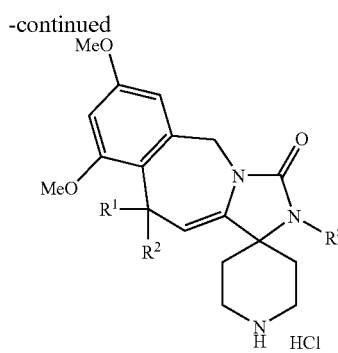

As depicted in Scheme 19 above, starting material (0.001695 mol) was dissolved in 4 M of hydrogen chloride in 1,4-dioxane (10 mL). The reaction mixture was stirred overnight and then concentrated in vacuo to provide the desired product.

Scheme 20

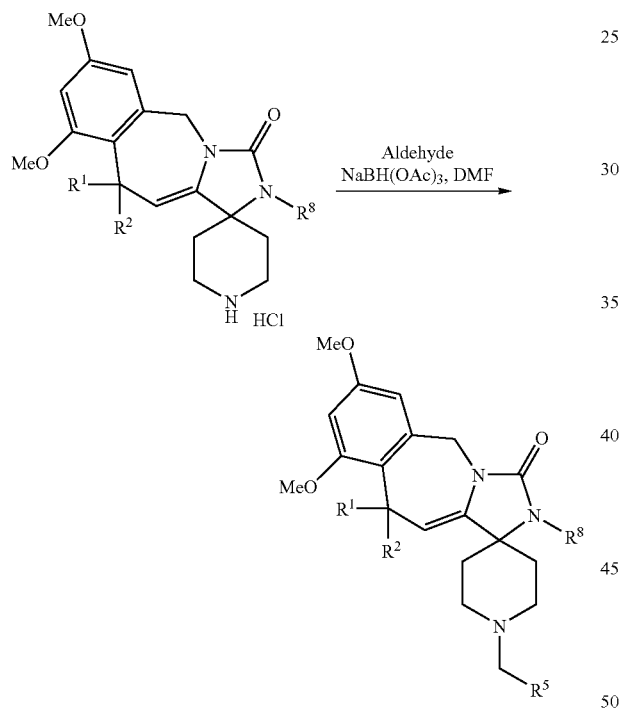

Scheme 20 above depicts a general method for introducing the —X—R⁵ group, where X is —CH₂—. As depicted in Scheme 20 above, starting material (0.0002451 mol), 4 Å molecular sieves, and aldehyde (0.000368 mol) were dissolved/suspended in N,N-dimethylformamide (1.0 mL). After stirring for 30 minutes, sodium triacetoxyborohydride (0.000343 mol) was added. The reaction mixture was stirred overnight then quenched with water. In some cases the desired product would precipitate upon quenching the reaction with water, in which case it could be isolated by filtration and subsequently purified by flash chromatography. In other cases the desired product could be extracted using a suitable water-immiscible organic solvent and then subsequently purified by either flash chromatography or reverse phase preparative HPLC.

Compounds ER-819991 and ER-819995 were prepared in substantially the same manner as described in connection with Schemes 18-20 above.

Scheme 21

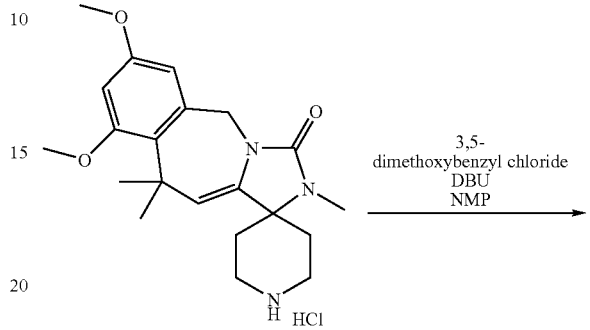

ER-819623

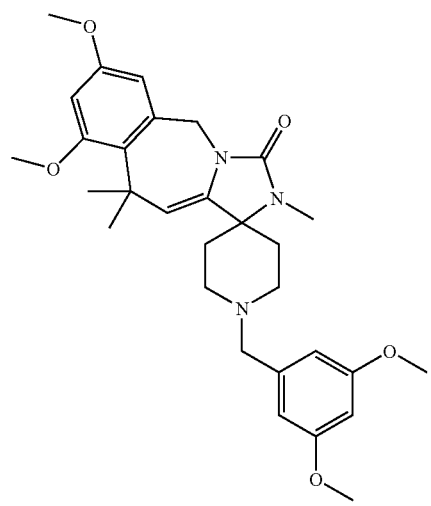

ER-819658

ER-819658: As depicted in Scheme 21 above, a 2 mL microwave reactor vial was charged with ER-819623 (71.6 mg, 0.000176 mol), 3,5-dimethoxybenzyl chloride (41.1 mg, 0.000220 mol), N-methylpyrrolidinone (700.0 µL) and 1,8-diazabicyclo[5.4.0]undec-7-ene (60.0 µL, 0.000401 mol). The reaction mixture was sealed and was heated at 180° C. for 60 seconds in the microwave. Purification by reverse phase HPLC provided ER-819658 (54.9 mg, 60%).

ER-819637 and ER-819627 were prepared in substantially the same manner as ER-819658.

Scheme 22

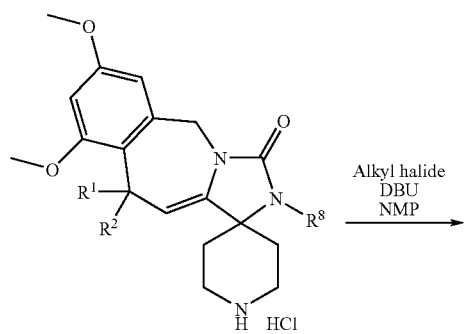

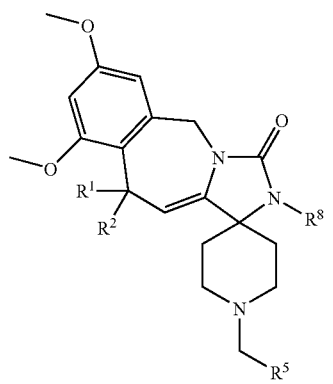

Scheme 22 above depicts another general method for introducing the —X—R⁵ group, where X is —CH₂—. As depicted in Scheme 22 above, a 2 mL microwave reactor vial was charged with starting material (0.000176 mol), an alkyl halide (0.000220 mol), N-methylpyrrolidinone (700.0 μL) and 1,8-diazabicyclo[5.4.0]undec-7-ene (0.000401 mol). The reactor vial was sealed and heated at 180° C. for 60 seconds in the microwave. Purification by reverse phase HPLC provided the desired product.

Scheme 23

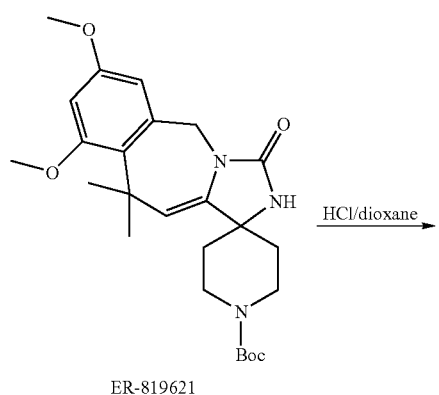

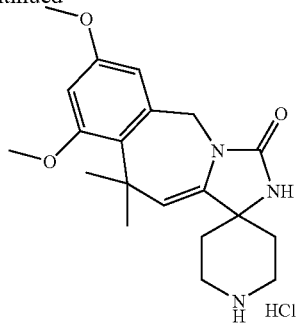

ER-819666: As depicted in Scheme 23 above, to a flask containing ER-819621 (2.30 g, 0.00503 mol) was added a 4 M solution of hydrogen chloride in 1,4-dioxane (15.0 mL). The reaction mixture was stirred at room temperature for 30 minutes then concentrated in vacuo to provide ER-819666 (1.98 g, quantitative).

Scheme 24

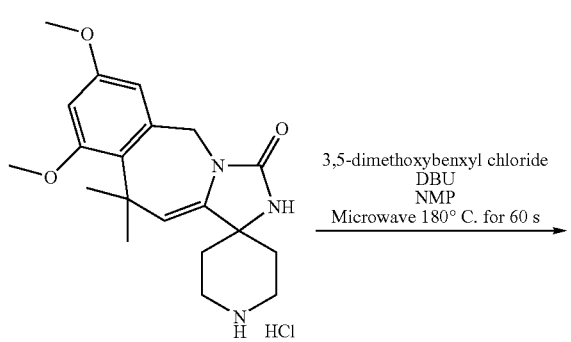

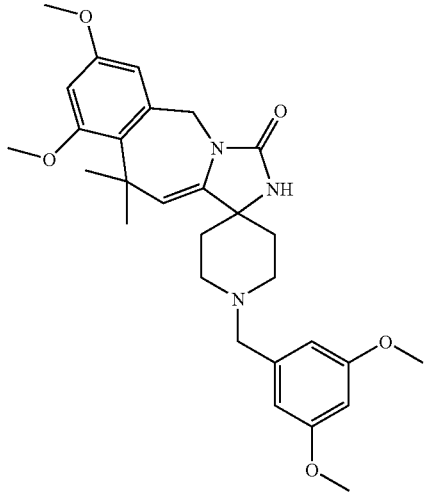

ER-819585: As depicted in Scheme 24 above, a 2 mL microwave reactor vial containing a stir bar was charged with ER-819666 (653.4 mg, 0.001659 mol), 3,5-dimethoxybenzyl chloride (377.6 mg, 0.002023 mol), N-methylpyrrolidinone (5.00 mL, 0.0518 mol) and 1,8-diazabicyclo[5.4.0]undec-7-ene (560.0 μL, 0.003745 mol). The reactor vial was sealed and heated at 180° C. for 60 seconds in the microwave. Purification by reverse phase HPLC provided ER-819585 (52.1 mg, 68%).

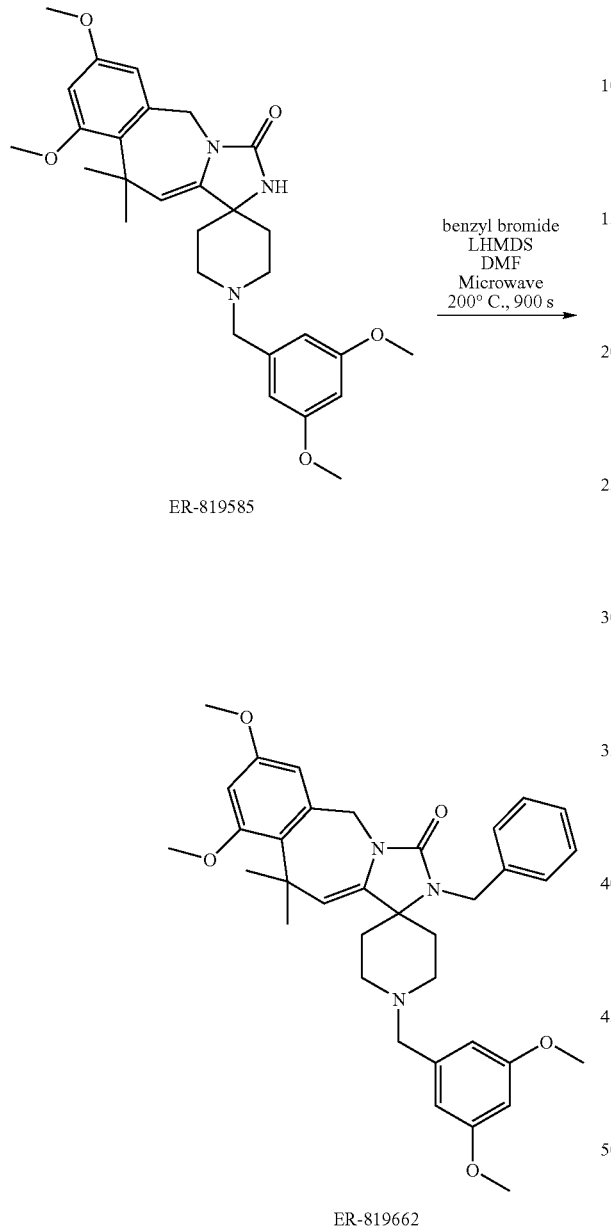

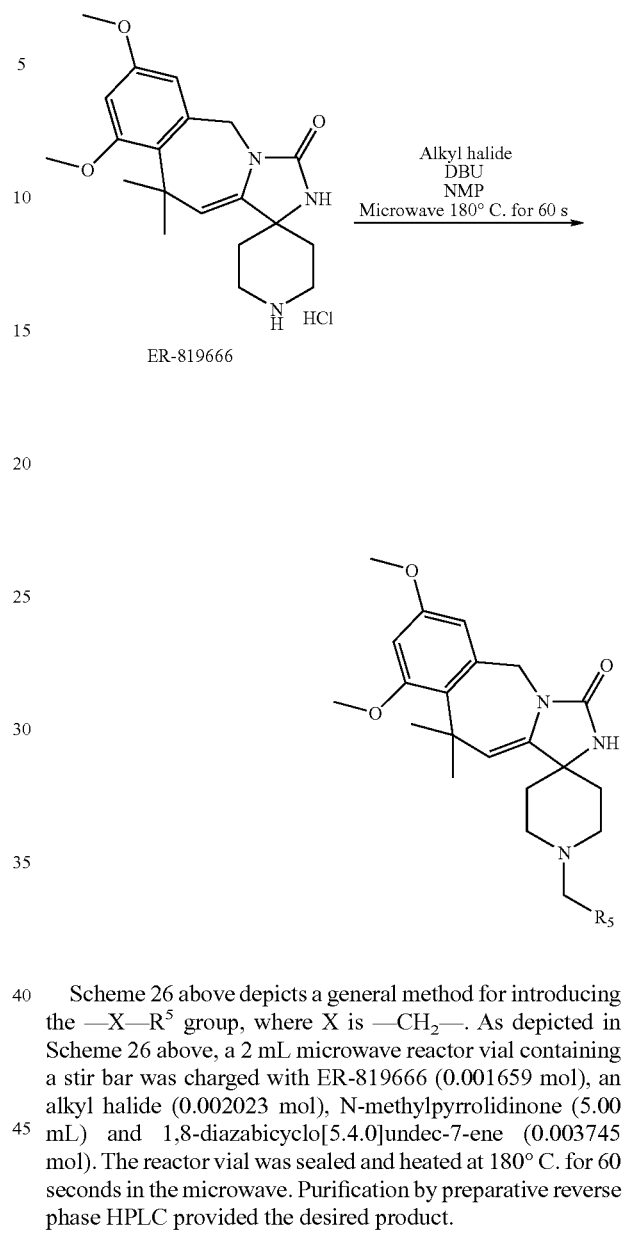

Scheme 26 above depicts a general method for introducing the —X—$R^5$ group, where X is —$CH_2$—. As depicted in Scheme 26 above, a 2 mL microwave reactor vial containing a stir bar was charged with ER-819666 (0.001659 mol), an alkyl halide (0.002023 mol), N-methylpyrrolidinone (5.00 mL) and 1,8-diazabicyclo[5.4.0]undec-7-ene (0.003745 mol). The reactor vial was sealed and heated at 180° C. for 60 seconds in the microwave. Purification by preparative reverse phase HPLC provided the desired product.

ER-819621: As depicted in Scheme 25 above, a 2 mL microwave reactor vial equipped with a stir bar was charged with ER-819585 (70.0 mg, 0.000138 mol), N,N-dimethylformamide (830.0 μL, 0.01072 mol), benzyl bromide (40.0 μL, 0.000336 mol) and a 1.00 M solution of lithium hexamethyldisilazide in tetrahydrofuran (350.0 μL). The reactor vial was sealed and heated at 200° C. for 900 sec in the microwave. Purification by preparative reverse phase HPLC provided ER-819662 (35.14 mg, 43%).

ER-819663, ER-819661, ER-819659, ER-819650, ER-819647, ER-819641 were prepared in substantially the same manner as ER-819662.

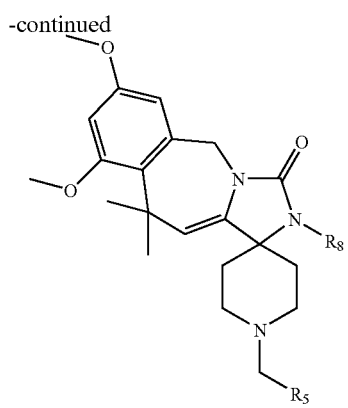

Scheme 27 above depicts a general method for introducing the $R^8$ group. As depicted in Scheme 27 above, a 2 mL microwave reactor vial equipped with a stir bar was charged with starting material (0.000138 mol), N,N-dimethylformamide (830 µL), $R^8$-bromide (0.000336 mol) and a 1.00 M solution of lithium hexamethyldisilazide in tetrahydrofuran (350 µL). The reactor vial was sealed and heated at 200° C. for up to 2700 sec in the microwave. Purification by preparative reverse phase HPLC provided the desired product.

ER-819590: As depicted in Scheme 28 above, to a solution of ER-819585 (31.6 mg, 0.0000622 mol) and 1-[3-(bromomethyl)phenyl]-1H-pyrrole (18.2 mg, 0.0000747 mol) in N,N-dimethylformamide (500 µL, 0.007 mol) was added sodium hydride (2.99 mg, 0.0000747 mol). The reaction mixture was stirred overnight then quenched cautiously with water (1 mL), and extracted several times with ethyl acetate. The organic extracts were combined, washed with water and brine, dried over magnesium sulfate, filtered, and concentrated in vacuo. Flash chromatography (eluent: 50% ethyl acetate in hexanes) provided ER-819590 (18.8 mg, 46%) as a colorless solid.

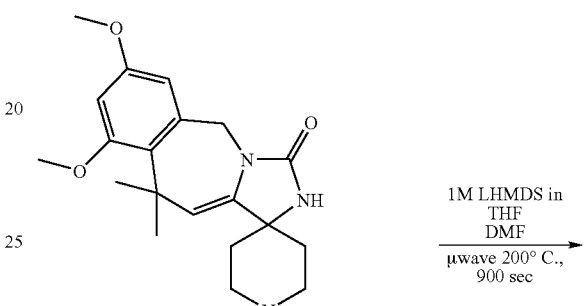

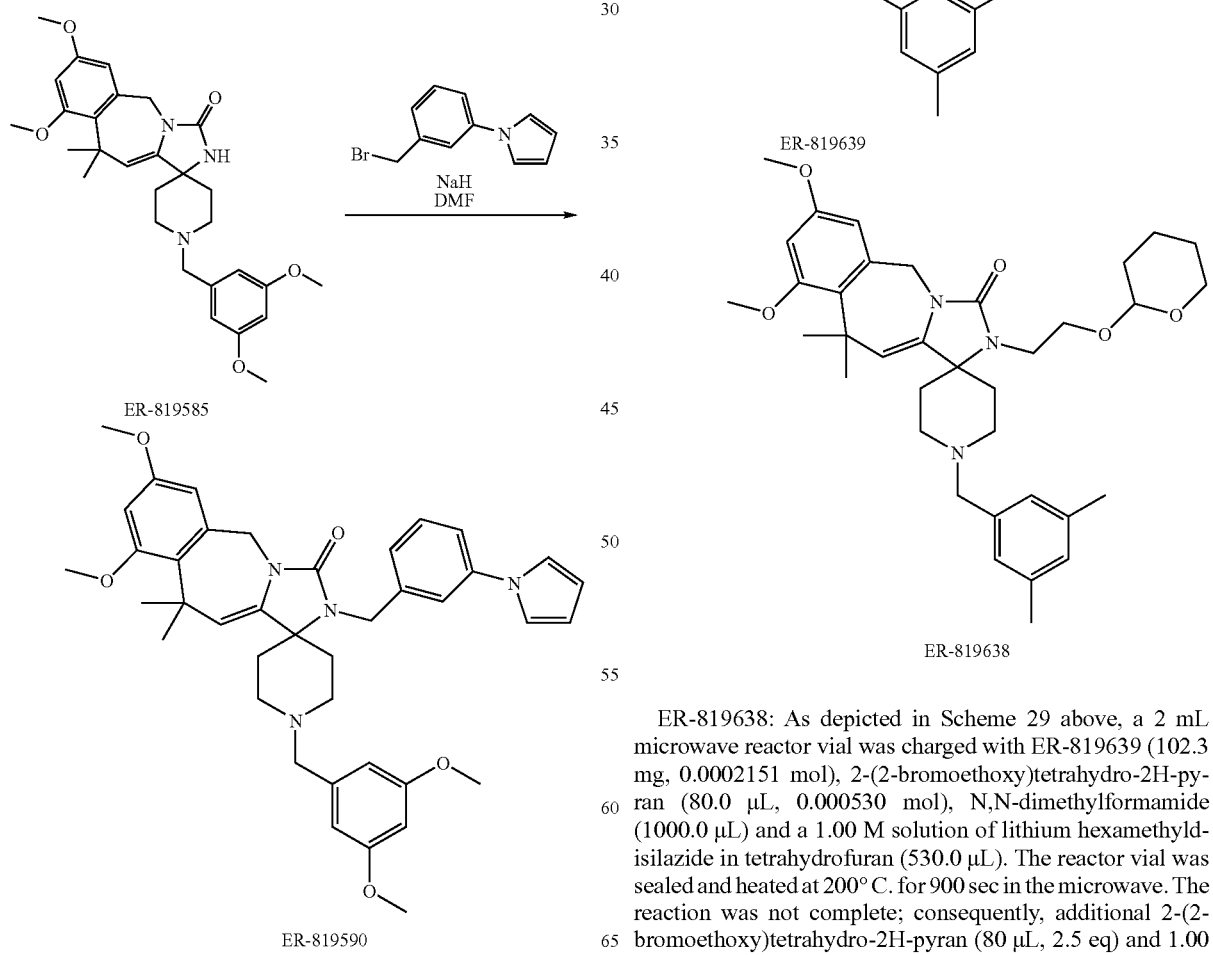

ER-819638: As depicted in Scheme 29 above, a 2 mL microwave reactor vial was charged with ER-819639 (102.3 mg, 0.0002151 mol), 2-(2-bromoethoxy)tetrahydro-2H-pyran (80.0 µL, 0.000530 mol), N,N-dimethylformamide (1000.0 µL) and a 1.00 M solution of lithium hexamethyldisilazide in tetrahydrofuran (530.0 µL). The reactor vial was sealed and heated at 200° C. for 900 sec in the microwave. The reaction was not complete; consequently, additional 2-(2-bromoethoxy)tetrahydro-2H-pyran (80 µL, 2.5 eq) and 1.00 M lithium hexamethyldisilazide solution in tetrahydrofuran (530 µL, 2.4 eq) were added and the vial reheated at 200° C.

for 900 sec. Purification by preparative reverse phase HPLC provided ER-819638 (57.8 mg, 44.5%).

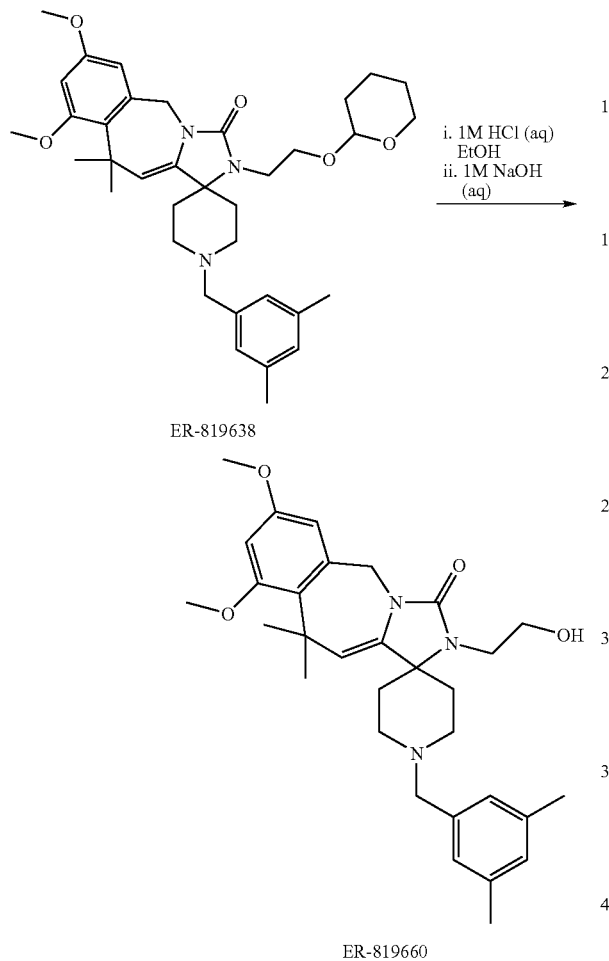

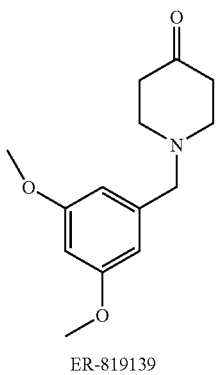

ER-819660: As depicted in Scheme 30 above, a solution of ER-819638 (57.8 mg, 0.0000957 mol) in ethanol (0.539 mL, 0.00922 mol) was treated with 1M hydrochloric acid (0.970 mL) and stirred at room temperature for 3 hours. The reaction mixture was neutralized by dropwise addition of 1 M aqueous sodium hydroxide (0.970 mL). Purification by preparative reverse phase HPLC provided ER-819660 (29.06 mg, 58.4%).

ER-819657 and ER-819642 were prepared in substantially the same manner as ER-819660.

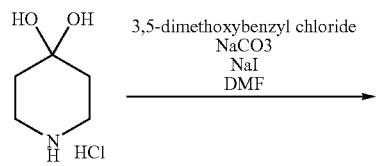

ER-819139: As depicted in Scheme 31 above, a 2 L round bottom flask was charged with 4-piperidone monochloride monohydrate (46.5 g, 0.302 mol) and N,N-dimethylformamide (600 mL). To the resulting suspension were added sodium carbonate (58.3 g, 0.550 mol), sodium iodide (28.9 g, 0.193 mol) and 3,5-dimethoxybenzyl chloride (51.4 g, 0.275 mol) under nitrogen. The resulting beige suspension was then heated to 90° C. and left to stir overnight under nitrogen. The reaction mixture became cloudy and golden yellow. The reaction mixture was filtered and then the resultant orange filtrate concentrated to a minimum amount of solvent by high vacuum rotavap. Saturated aqueous ammonium chloride solution (300 mL) was added and the mixture extracted with MTBE (250 mL extractions). The combined organic phases were dried (anhydrous Na$_2$SO$_4$) and concentrated to give a reddish brown oil ER-823139 (quantitative yield assumed).

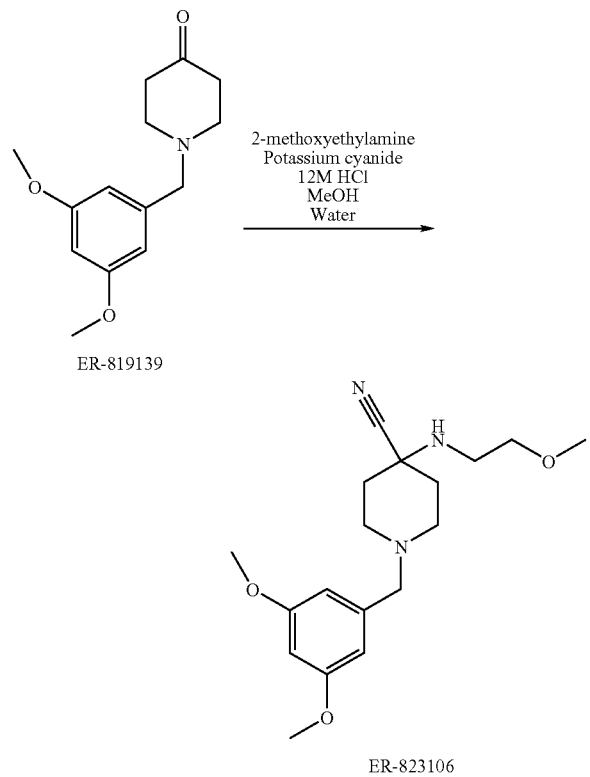

ER-823106: As depicted in Scheme 32 above, to a suspension of ER-823139 in water (2.8 mL) and methanol (3.0 mL) was added 2-methoxyethylamine (1.36 mL, 0.0157 mol). To the resultant brown suspension was added dropwise a 12M solution of aqueous hydrochloric acid (1.31 mL). The reaction mixture was heated to 40° C. and a solution of potassium cyanide (1.02 g, 0.0157 mol) in water (2.3 mL, 0.13 mol) was added dropwise. A significant amount of starting material was still not dissolved. Thus, additional methanol (3.0 mL, 0.074 mol) and water (2.8 mL, 0.16 mol) were added and the suspension was stirred at room temperature for 18 hr. The reaction mixture was then extracted with ethyl acetate (2×). The combined organics were washed with water, brine, dried over sodium sulfate, filtered and concentrated in vacuo to give yellow-brown crude product ER-823106 (4.70 g, 99%).

with brine, dried over sodium sulfate, filtered and concentrated to give a dark yellow oil. The oil was purified by flash chromatography using DCM/Ethyl acetate (1:1), DCM/Ethyl acetate/MeOH (9:9:1) and Ethyl acetate/MeOH (9:1) to give ER-819669 (17 mg, 31%).

Scheme 33

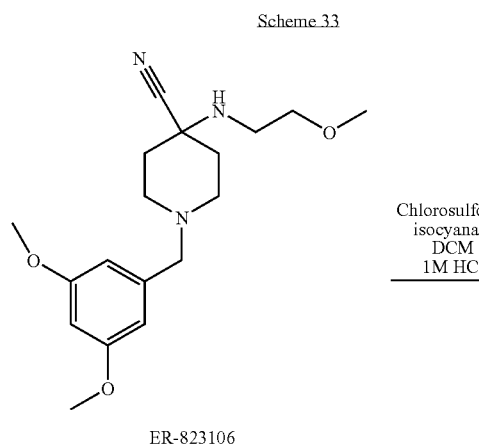

ER-823106

Scheme 34

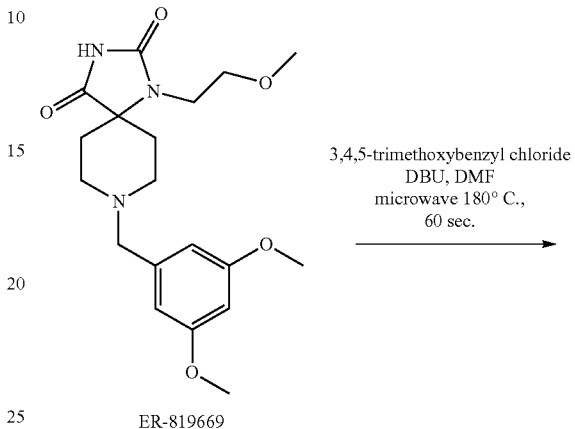

ER-819669

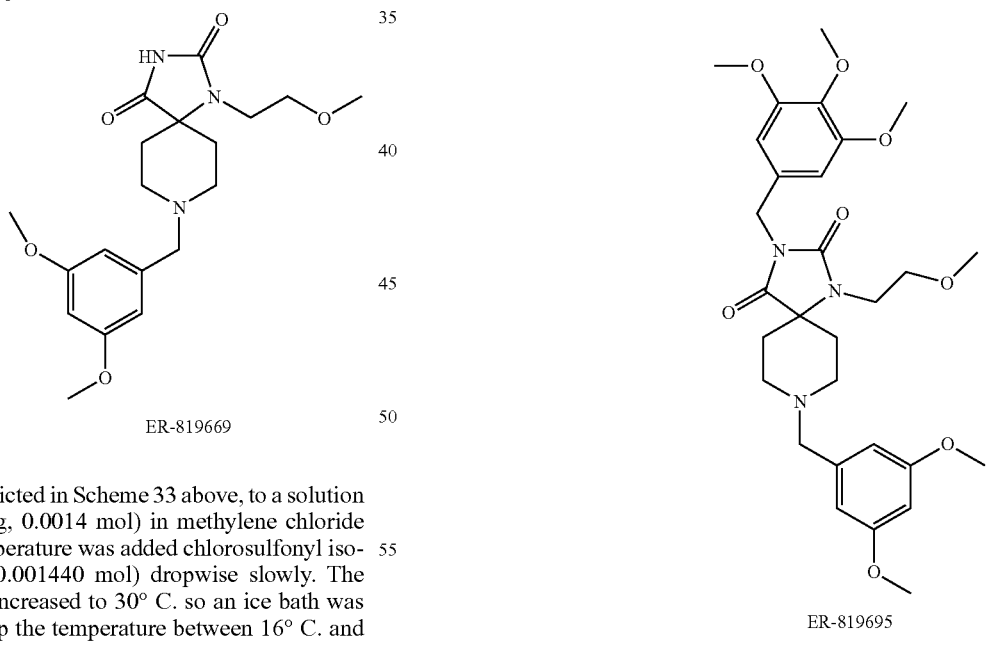

ER-819669

ER-819669: As depicted in Scheme 33 above, to a solution of ER-823106 (0.48 g, 0.0014 mol) in methylene chloride (2.0 mL) at room temperature was added chlorosulfonyl isocyanate (0.125 mL, 0.001440 mol) dropwise slowly. The internal temperature increased to 30° C. so an ice bath was then employed to keep the temperature between 16° C. and 25° C. The mixture was stirred at room temperature for 1 hr then concentrated in vacuo to give pale yellow foam. To the residue was added 1M hydrochloric acid (4.0 mL). The resulting suspension was stirred for 10 min at room temperature, than heated at 110° C. for 1 hr. The reaction mixture was then cooled to 0° C., neutralized with 5 M aqueous sodium hydroxide (~1.2 mL). A light yellow milky precipitate formed, which was extracted with ethyl acetate (5×—until little/no product in last extract by TLC). The combined organics were washed

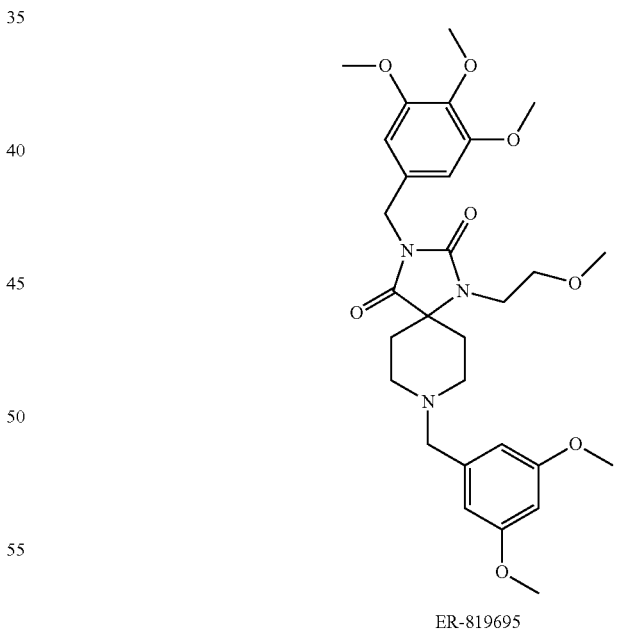

ER-819695

ER-819695: As depicted in Scheme 34 above, a solution of ER-819669 (110 mg, 0.00029 mol), 1,8-diazabicyclo[5.4.0]undec-7-ene (87.2 μL, 0.000583 mol) and 3,4,5-trimethoxybenzyl chloride (107 mg, 0.000495 mol) in N,N-dimethylformamide (1.1 mL) was heated at 180° C. for 60 seconds in the microwave. Purification by preparative reverse phase HPLC provided ER-819695 (129 mg, 79%) as colorless oil.

Scheme 35

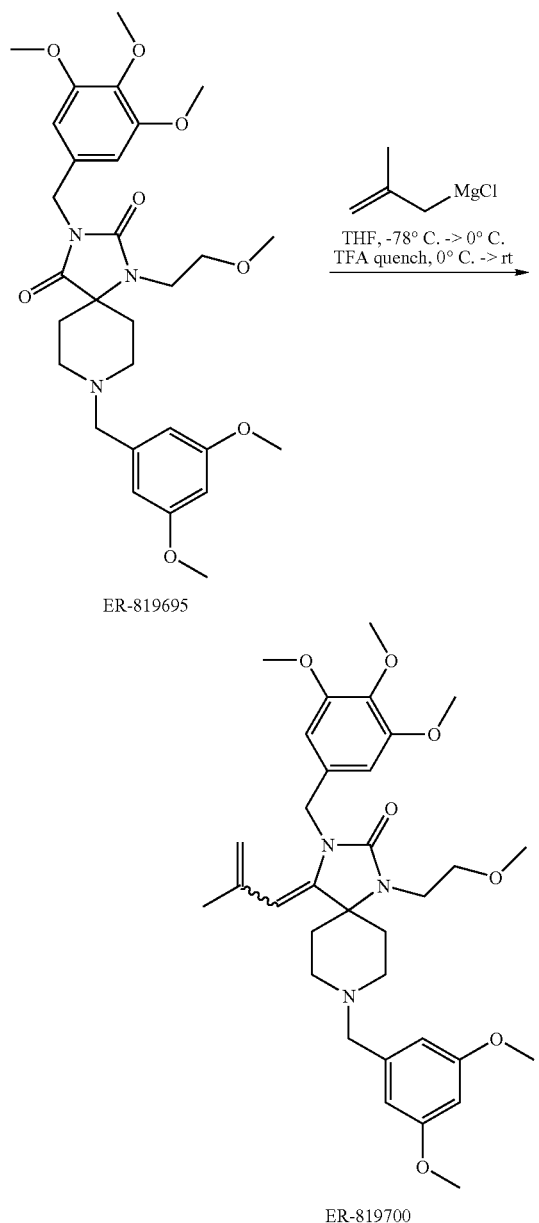

ER-819695

ER-819700

ER-819700: As depicted in Scheme 35 above, to a solution of ER-819695 (118 mg, 0.000212 mol) in tetrahydrofuran (4 mL, 0.05 mol) at −78° C. was added a 0.5 M solution of 2-methylallylmagnesium chloride in tetrahydrofuran (4.232 mL) dropwise over 3 min keeping internal temperature below at −50° C. The cooling bath was removed, and the reaction mixture allowed to warm to 0° C. After 2 h at 0° C., TLC (9:1 Ethyl acetate-MeOH, ninhydrin stain, UV) showed complete reaction. The reaction mixture was quenched by slow careful addition of trifluoroacetic acid (0.978 mL, 0.0127 mol) at 0° C. to give yellow solution. The reaction mixture was then warmed to room temperature, stirred for 10 min and then concentrated in vacuo using a rotary evaporator with a water bath temperature of 30° C. The resultant yellow residue was dissolved in ethyl acetate, and treated cautiously with an excess of saturated aqueous sodium bicarbonate solution. The biphasic mixture was stirred until gas evolution ceased. The organic layer was separated and the aqueous layer was re-extracted with ethyl acetate. The combined organic extracts were dried over $Na_2SO_4$, filtered, and concentrated in vacuo. Purification by preparative TLC ethyl acetate/MeOH (9:1) gave ER-819700 (85 mg, 67%).

Scheme 36

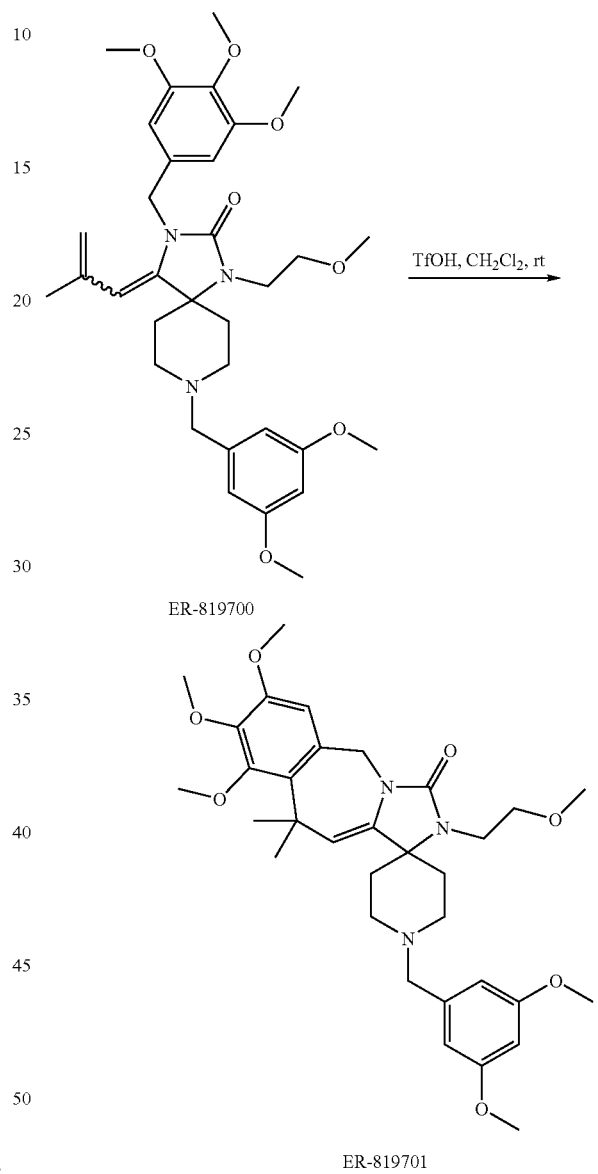

ER-819700

ER-819701

ER-819701: As depicted in Scheme 36 above, to a solution of ER-819700 (45 mg, 0.000076 mol) in methylene chloride (2.25 mL) was added trifluoromethanesulfonic acid (20 μL, 0.0002 mol) dropwise at room temperature. After 40 min the reaction was quenched with sat. $NaHCO_3$ (color changed from dark yellow to almost colorless), vigorously stirred for 20 min at room temperature, extracted with methylene chloride (3×). The combined extracts were dried over $Na_2SO_4$, filtered, concentrated in vacuo. Purification by flash chromatography using 100% ethyl acetate followed by ethyl acetate/methanol (19:1) afforded ER-819701 (26 mg, 58%).

ER-819655, ER-819672, ER-819698, ER-819704 were prepared in substantially the same manner as ER-819701.

Scheme 37

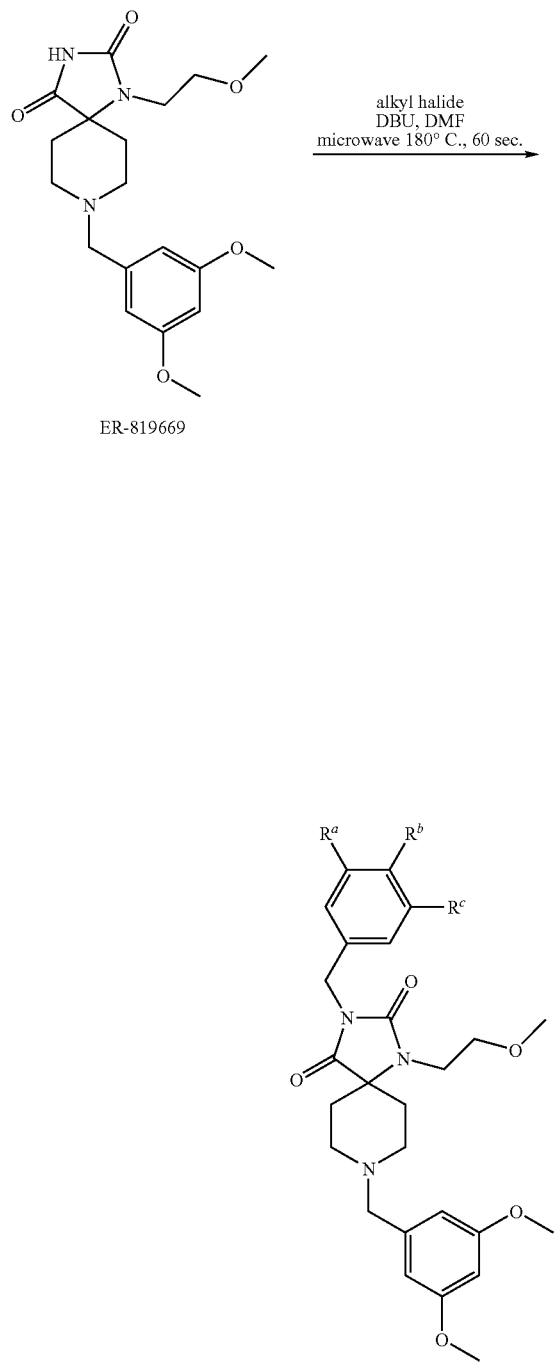

ER-819669

Scheme 37 above depicts a general method for introducing various $R^a$, $R^b$, and $R^c$ groups. As depicted in Scheme 37 above, a solution of ER-819669 (0.00029 mol), 1,8-diazabicyclo[5.4.0]undec-7-ene (87.2 μL, 0.000583 mol) and an alkyl halide (0.000495 mol) in N,N-dimethylformamide (1.1 mL) was heated at 180° C. for 60 seconds in the microwave. Purification by preparative reverse phase HPLC provided the desired product.

Scheme 38

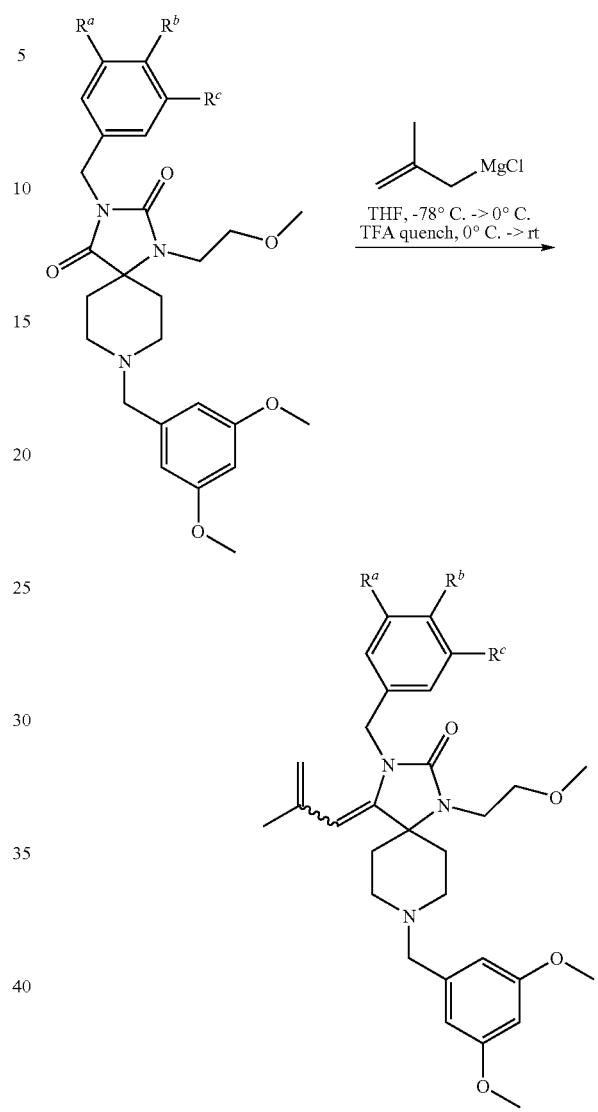

As depicted in Scheme 38 above, to a solution of starting material (0.000212 mol) in tetrahydrofuran (4 mL) at –78° C. was added a 0.5 M solution of 2-methylallylmagnesium chloride in tetrahydrofuran (4.232 mL) dropwise over 3 min keeping internal temperature below at –50° C. The cooling bath was removed to allow the reaction mixture to warm to 0° C. After stirring for 2 hrs at 0° C., the reaction mixture was quenched by slow careful addition of trifluoroacetic acid (0.978 mL, 0.0127 mol). The reaction mixture was then warmed to room temperature, stirred for 10 min and then concentrated in vacuo using a rotary evaporator with the water bath temperature set at 30° C. The resultant residue was dissolved in ethyl acetate, and excess saturated aqueous sodium bicarbonate was added cautiously. The biphasic mixture was stirred until gas evolution ceased. The organic layer was separated; the aqueous layer was extracted with ethyl acetate. The combined organic extracts were dried over $Na_2SO_4$, filtered, and concentrated in vacuo. Purification by preparative TLC with ethyl acetate/methanol (9:1) afforded the desired product.

Scheme 39

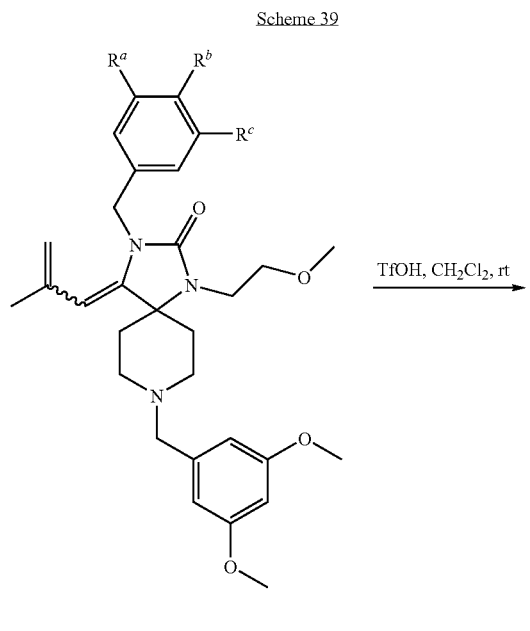

Scheme 40

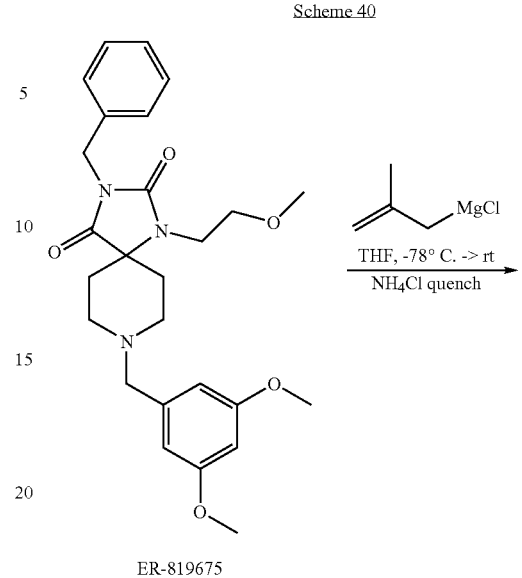

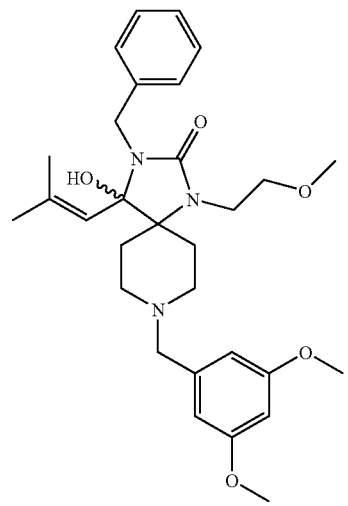

As depicted in Scheme 39 above, to a solution of starting material (0.000076 mol) in methylene chloride (2.25 mL) was added trifluoromethanesulfonic acid (20 μL, 0.0002 mol) dropwise at room temperature. After 40 min the reaction was quenched with an excess of saturated aqueous sodium bicarbonate, vigorously stirred for 20 min at room temperature, and extracted with methylene chloride (3×). The combined extracts were dried over $Na_2SO_4$, filtered, and concentrated in vacuo. Purification by flash chromatography using 100% ethyl acetate followed by ethyl acetate/methanol (19:1) afforded the desired product.

ER-819676: As depicted in Scheme 40 above, to a solution of ER-819675 (80.0 mg, 0.000171 mol) in tetrahydrofuran (2 mL, 0.03 mol) at −78° C. was added a 0.5 M solution of 2-methylallylmagnesium chloride in tetrahydrofuran (3.422 mL) dropwise over 3 min keeping internal temperature below −60° C. The reaction mixture was allowed to warm slowly to −35° C. (over approximately 1.5 hours). The reaction was quenched with saturated aqueous ammonium chloride solution, and extracted with ethyl acetate (2×). The combined extracts were dried over $Na_2SO_4$, and concentrated in vacuo. The crude product was purified by flash chromatography eluting with ethyl acetate/methanol (19:1) to afford ER-819676 (85 mg, 95%).

Scheme 41

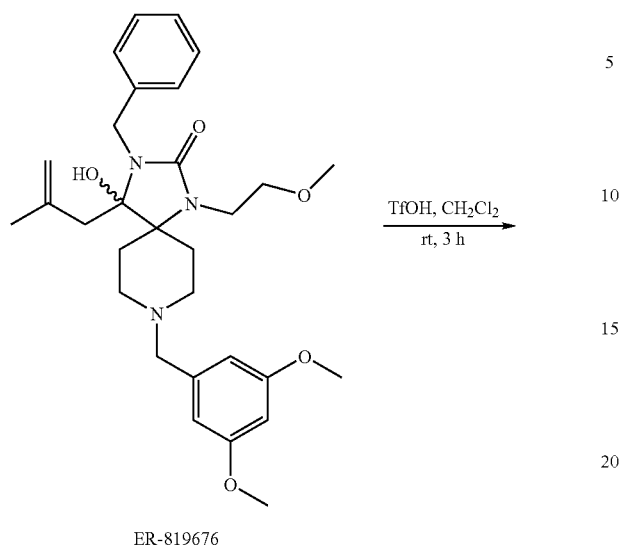

ER-819676

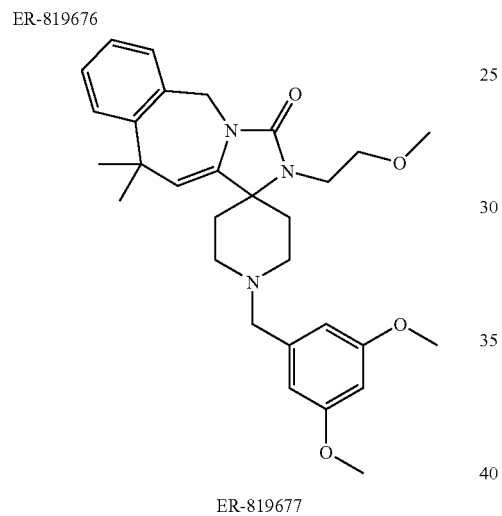

ER-819677

ER-819677: As depicted in Scheme 41 above, to a solution of ER-819676 (56 mg, 0.00011 mol) in methylene chloride (5000 µL) was added trifluoromethanesulfonic acid (90 µL, 0.001 mol) dropwise at room temperature to give yellow solution. After 3 h, the reaction was quenched with saturated aqueous sodium bicarbonate solution, vigorously stirred for 20 min at room temperature and extracted with methylene chloride (3x). The combined extracts were dried with Na$_2$SO$_4$, filtered and concentrated in vacuo. Purification by preparative TLC using ethyl acetate/methanol (9:1) as eluent afforded ER-819677 (22 mg, 40%).

Scheme 42

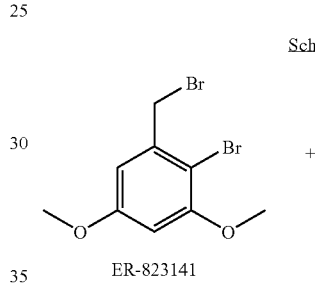

ER-820757

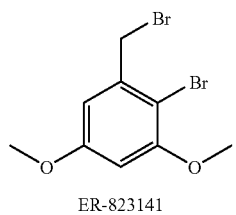

ER-823141

ER-823141: As depicted in Scheme 42 above, ER-820757 (1.62 g, 6.556 mmol) was dissolved in methylene chloride (80 mL). Triphenylphosphine (3.44 g, 13.1 mmol) and carbon tetrabromide (4.35 g, 13.1 mmol) were added and the mixture stirred overnight at room temperature. Concentration in vacuo followed by flash chromatography using ethyl acetate/heptane (1:9) as eluent afforded ER-823141 (1.93 g, 95%) as a light grey solid.

Scheme 43

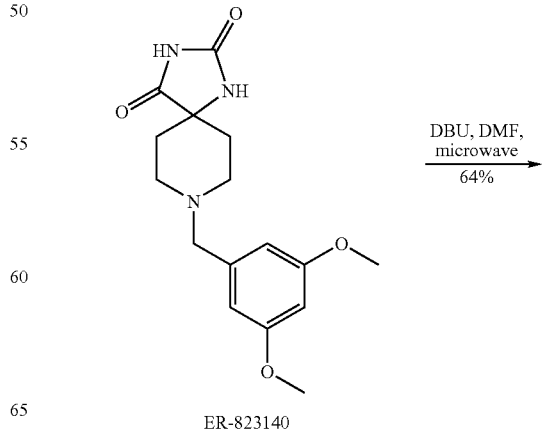

ER-823140

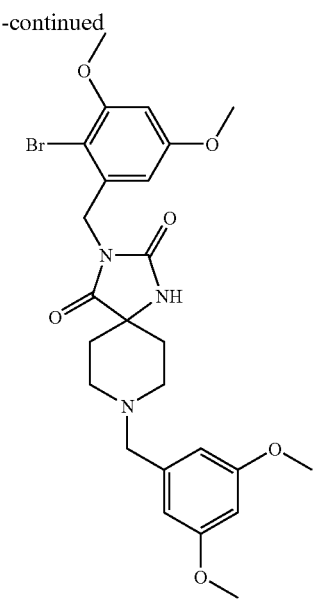

ER-823142

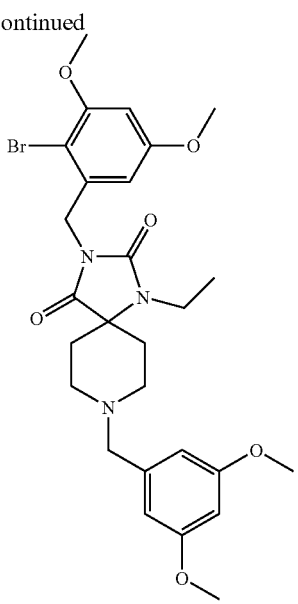

ER-823163

ER-823142: As depicted in Scheme 43 above, a 5 mL microwave reactor vial, equipped with a magnetic stir bar, was charged with ER-823140 (200.0 mg, 0.6263 mmol), N,N-dimethylformamide (2.0 mL), ER-823141 (388 mg, 1.25 mmol) and 1,8-diazabicyclo[5.4.0]undec-7-ene (211 μL, 1.41 mmol) to give a light yellow solution. The reaction mixture was heated at 180° C. for 90 seconds in the microwave. Ethyl acetate (5.0 mL) was added followed by a saturated aqueous ammonium chloride solution (2.5 mL) and water (2.5 mL). The organic layer was isolated and the aqueous layer extracted (2×) with ethyl acetate (5.0 mL). The combined organic extracts were washed with saturated aqueous sodium chloride solution (5.0 mL). The organic layer was dried with sodium sulfate, filtered and concentrated in vacuo. The residue was purified by flash chromatography (0-2.5% methanol/ethyl acetate) to give ER-823142 (218 mg, 63%) as a colorless solid.

ER-823163: As depicted in Scheme 44 above, a 5 mL microwave reactor vial, equipped with a magnetic stir bar, was charged with ER-823142 (100.0 mg, 0.1823 mmol), N,N-dimethylformamide (1.00 mL), 1 M lithium hexamethyldisilazide solution in tetrahydrofuran (0.43 mL), and ethyl bromide (0.032 mL, 0.438 mmol). The mixture was heated at 170° C. for 150 seconds in the microwave. The reactor mixture was cooled to room temperature and treated with MTBE (2 mL). Saturated aqueous ammonium chloride solution (1 mL) was added and the mixture was stirred for 10 minutes. The organic layer was isolated and the aqueous layer back extracted with MTBE (2×2 mL). The combined organic layers were washed with saturated aqueous sodium chloride solution (2 mL). The organic layer was dried with sodium sulfate, filtered and concentrated in vacuo. The crude material was purified by flash chromatography (ethyl acetate) to give ER-823163 (83 mg, 79%) as a light yellow solid.

Scheme 44

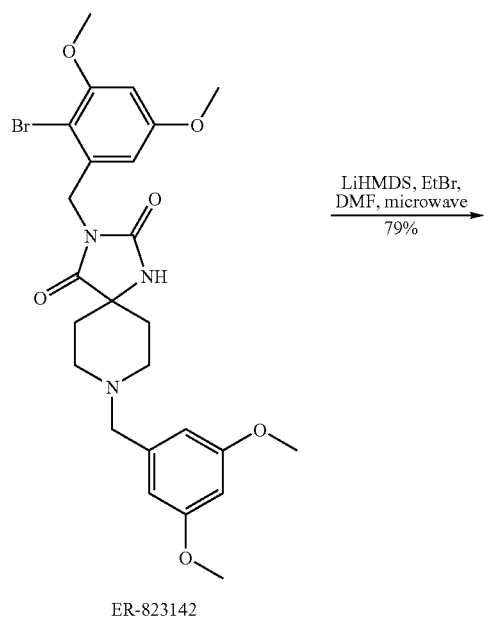

Scheme 45

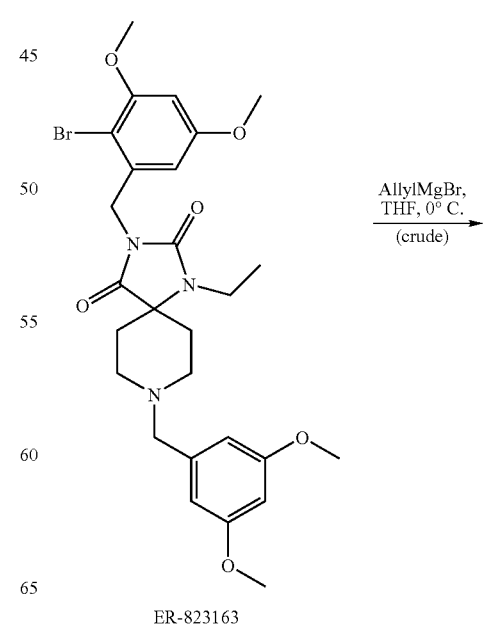

-continued

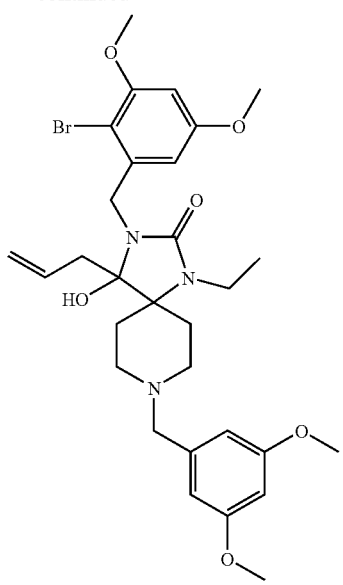

ER-823166

-continued

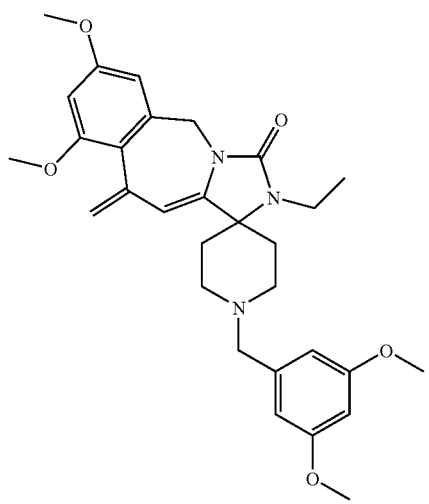

ER-819703

ER-823166: As depicted in Scheme 45 above, ER-823163 (153.0 mg, 0.2654 mmol) was dissolved in anhydrous tetrahydrofuran (1.5 mL) and the solution cooled to 0° C. A 1.0 M solution of allylmagnesium bromide in ether (1.327 mL) was added and the mixture stirred at 0° C. for 1.5 hours. Saturated aqueous ammonium chloride solution (1.5 mL) was added and the mixture was stirred for 10 minutes. The mixture was extracted (2×) with MTBE (7 mL). The combined organic layers were washed with saturated aqueous sodium chloride solution (3 mL). The organic layer was dried with sodium sulfate, filtered and concentrated in vacuo to afford crude ER-823166 (160 mg) which was used immediately without purification.

ER-819703: As depicted in Scheme 46 above, to a solution of ER-823166 (110.0 mg, 0.1778 mmol) in acetonitrile (2.5 mL) under an atmosphere of nitrogen in a 5 mL microwave reactor vial was added palladium acetate (20.0 mg, 0.0889 mmol), tri-o-tolylphosphine (27.6 mg, 0.0907 mmol) and triethylamine (99.1 µL, 0.711 mmol). The mixture was heated at 120° C. for 60 minutes in the microwave. The reaction mixture was filtered through a short pad of Celite and silica gel, and the pad subsequently washed with ethyl acetate/methanol (9:1). The filtrate was concentrated in vacuo. Purification of the resultant residue by preparative reverse phase HPLC provided ER-819703 (10 mg, 12%).

Scheme 46

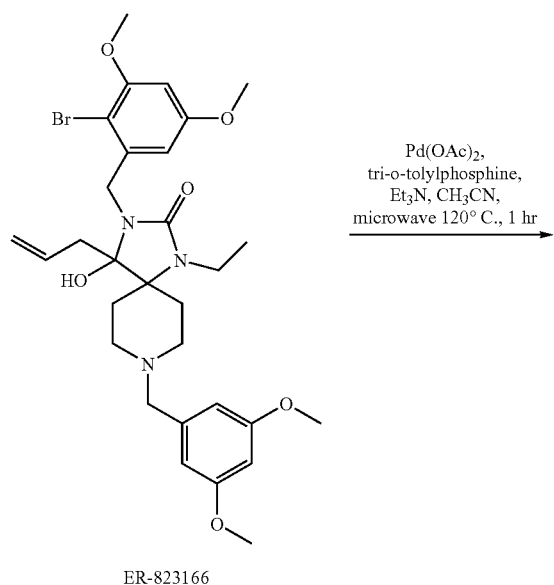

ER-823166

Scheme 47

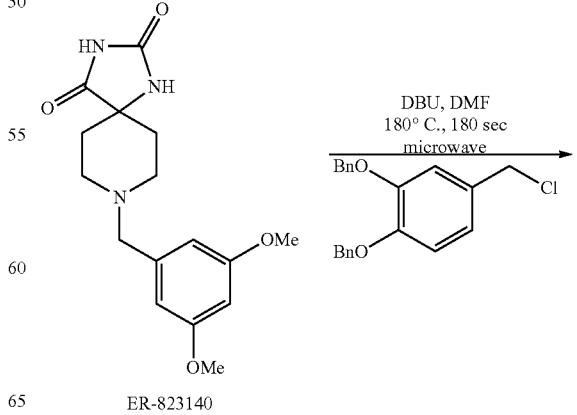

ER-823140

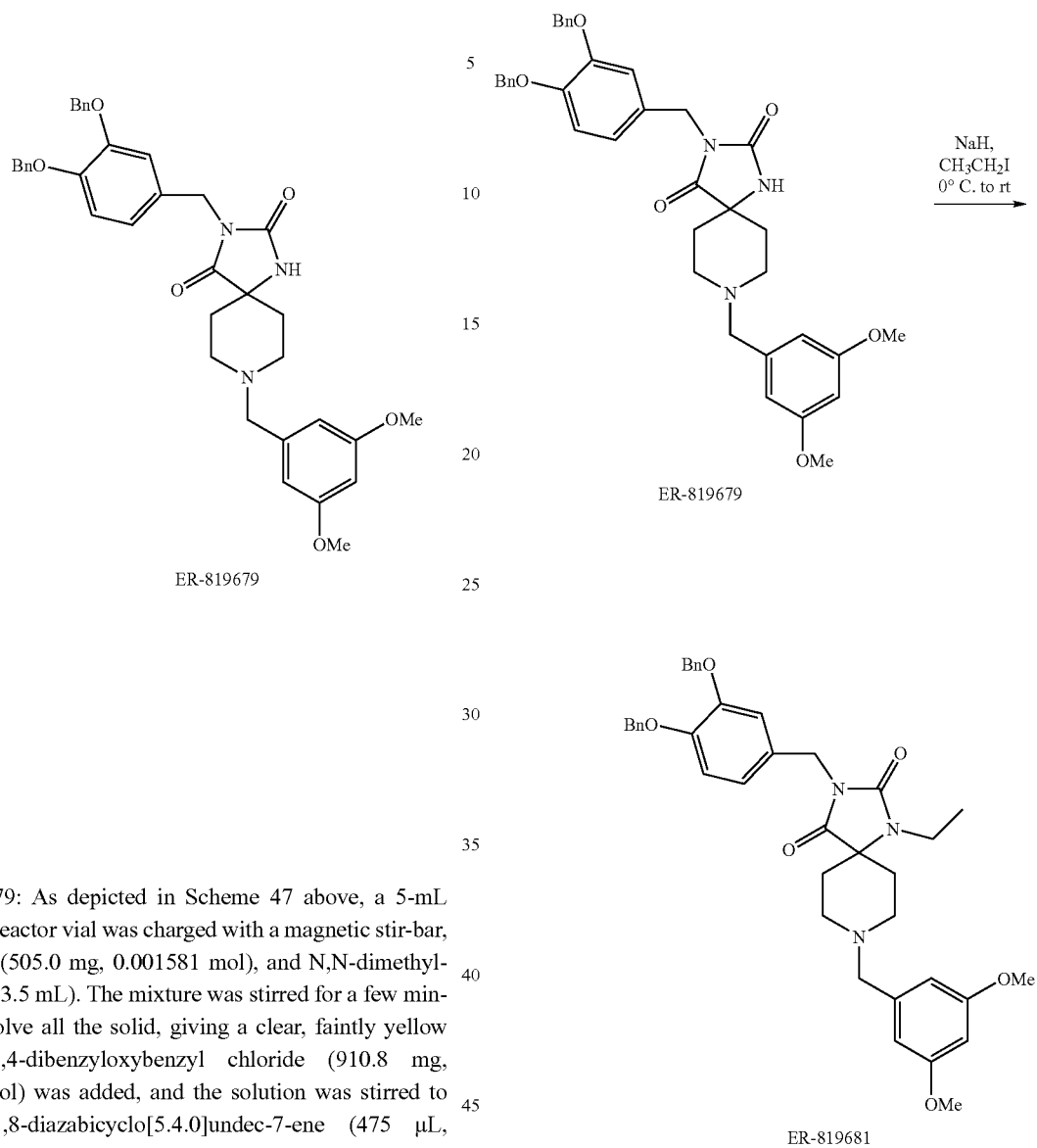

ER-819679: As depicted in Scheme 47 above, a 5-mL microwave reactor vial was charged with a magnetic stir-bar, ER-823140 (505.0 mg, 0.001581 mol), and N,N-dimethylformamide (3.5 mL). The mixture was stirred for a few minutes to dissolve all the solid, giving a clear, faintly yellow solution. 3,4-dibenzyloxybenzyl chloride (910.8 mg, 0.002688 mol) was added, and the solution was stirred to dissolve. 1,8-diazabicyclo[5.4.0]undec-7-ene (475 µL, 0.00318 mol) was then added via syringe. The solution rapidly took on a slightly greenish tint after the 1,8-diazabicyclo[5.4.0]undec-7-ene was added, but the color did not darken further. The clear solution was stirred to mix, the tube was sealed with a septum cap, and the reactor vial heated in the microwave at 180° C. for 90 sec., and then allowed to stand at room temperature overnight. TLC and mass spectroscopic analysis indicated a small amount of ER-823140 remaining. Consequently, the reactor vial was heated in the microwave again for 90 sec at 180° C. The clear, amber solution was diluted with ethyl acetate (80 mL) and washed with water (2×30 mL), saturated aqueous sodium bicarbonate solution (30 mL), water (30 mL), and saturated brine (30 mL), dried over anhydrous magnesium sulfate, filtered, and concentrated in vacuo to give ER-819679 (1.02 g, 104%) as a light tan solid. $^1$H NMR (CDCl$_3$) indicated sufficient purity for use in the next step without further purification.

ER-819681: As depicted in Scheme 48 above, ER-819679 (0.6204 g, 0.0009979 mol) was dissolved in N,N-dimethylformamide (5.0 mL, 0.064 mol) at room temperature, and the solution was cooled in an ice-water bath under nitrogen. Sodium hydride (47.9 mg, 0.00120 mol) was added all at once, and the mixture stirred for 40 min. Iodoethane (100 µL, 0.001250 mol) was added via syringe. The resultant cloudy solution was stirred with ice-water bath cooling for 2.3 h, and the bath was then removed. Stirring was continued at room temperature overnight. The reaction solution was diluted with ethyl acetate (80 mL) and water (25 mL), and the phases separated. The ethyl acetate phase was washed with water (2×25 mL), and saturated brine (30 mL), dried over anhydrous magnesium sulfate, filtered, and concentrated in vacuo to give an off-white film. This film was rinsed with heptanes (3×~2 mL), and the heptanes was decanted by pipette. The solid was re-dried under vacuum to give ER-819681 (648.0 mg, 100%) as a semi-solid foam that melted with warming.

Scheme 35

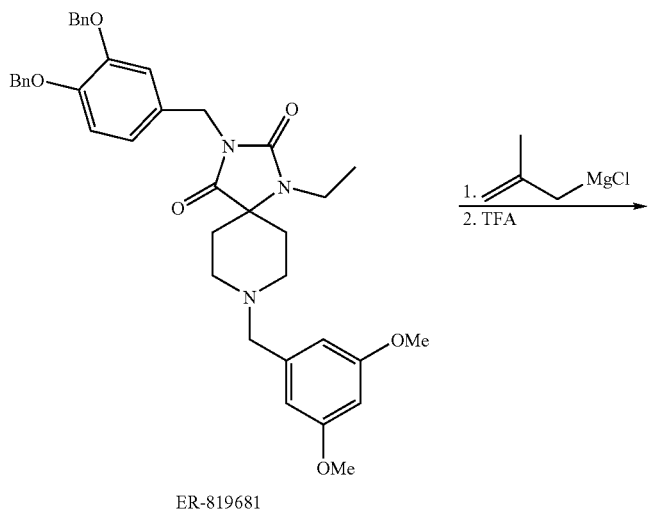

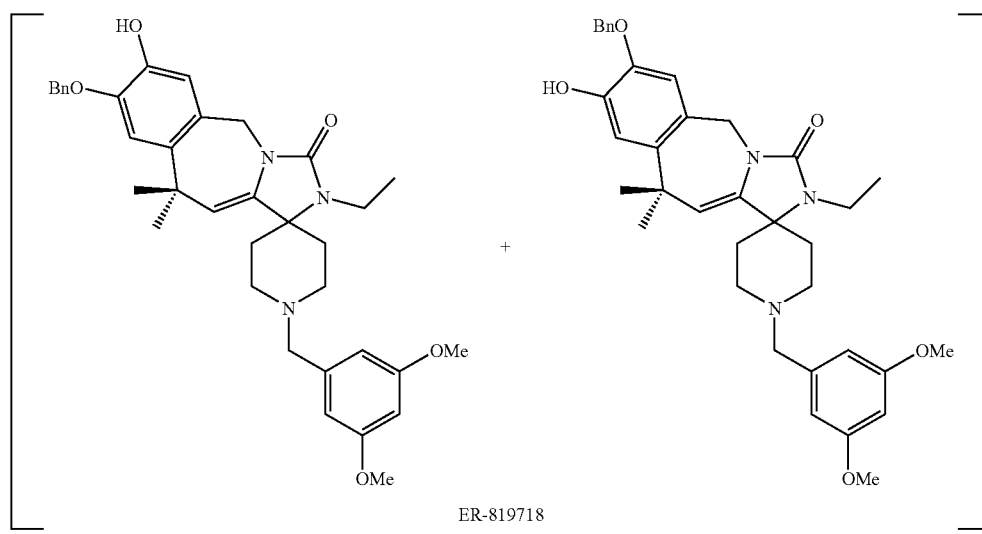

ER-819718: As depicted in Scheme 49 above, ER-819681 (200.3 mg, 0.0003083 mol) was dissolved in tetrahydrofuran (3.0 mL) under nitrogen, and the solution cooled to −78° C. in a dry ice/acetone bath. A 0.5 M solution of 2-methylallylmagnesium chloride in tetrahydrofuran (2.0 mL) was added via syringe over ca. 3 min, and the solution was allowed to stir at −78° C. for 5 min, and then the bath was removed, and the solution was stirred at room temperature for 2.5 h. The solution was re-cooled to −78° C. and quenched with 0.1 mL trifluoroacetic acid. This solution was then concentrated in vacuo to give a yellow foam. The flask was cooled to −78° C. in a dry ice/acetone bath and 3.0 mL of trifluoroacetic acid was added. The trifluoroacetic acid solidified, so the flask was removed from the bath, and allowed to warm to room temperature. After 3 hours, 1 mL of methylene chloride was added to help dissolve the solid. After ~7 hours total at room temperature, the red solution was concentrated in vacuo using a rotary evaporator with the water bath temperature set to approximately 40° C. The residual red-brown oil was dissolved in a few mL of ethyl acetate (with sonication) and diluted with a total of approximately 80 mL of ethyl acetate. This solution was washed with saturated sodium bicarbonate solution (40 mL), water (40 mL), and saturated brine (40 mL). The organic extract was then dried over anhydrous magnesium sulfate, filtered, and concentrated in vacuo to afford a yellow-brown oil (200.4 mg). Purification by preparative reverse phase HPLC provided ER-819717 (1.0 mg, 1.8%) and ER-819718 (1.2 mg, 2.2%).

Compounds of the present invention were prepared in accordance with the methods described herein and those known to one of ordinary skill in the art. Such compounds include those listed in Table 1 set forth below. Table 1 provides analytical data, including $^1$H NMR data, for exemplary compounds of the present invention.

TABLE 1

Analytical Data for Exemplary Compounds of Formula I

| Example # | Structure | ER-# | Analytical Data |
|---|---|---|---|
| 1 | 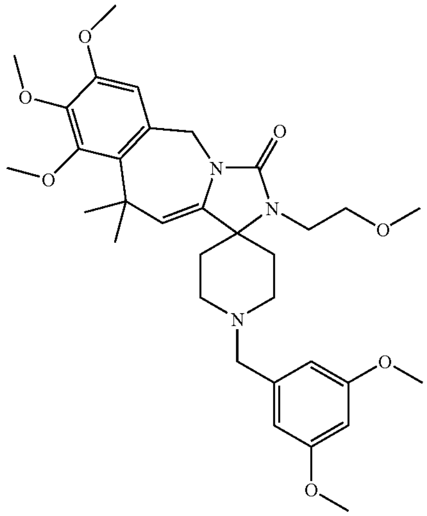 | 819701 Salt free | NMR $^1$H (400 MHz, CDCl$_3$) δ 6.63 (s, 1H), 6.51 (d, J = 2.3 Hz, 2H), 6.38 (t, J = 2.2 Hz 1H), 4.70 (s, 1H), 4.68 (s, 2H), 3.85 (s, 3H), 3.84 (s, 3H), 3.81 (s, 6H), 3.80 (s, 3H), 3.54 (s, 2H), 3.51 (t, J = 6.2 Hz, 2H), 3.38 (t, J = 6.6 Hz, 2H), 3.35 (s, 3H), 2.78-2.75 (m, 2H), 2.54 (t, J = 10.9 Hz, 2H), 2.01-1.93 (m, 2H), 1.69 (s, 6H), 1.65-1.62 (m, 2H) |
| 2 | 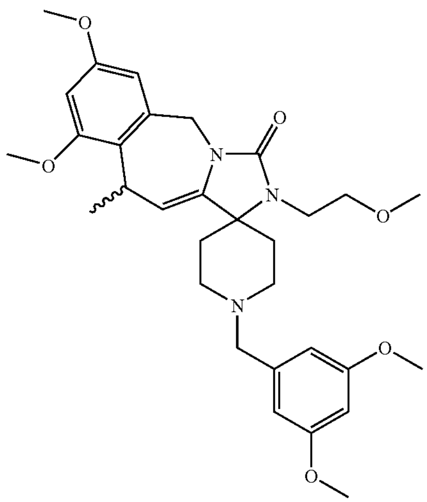 | 819543 Salt free | NMR $^1$H (400 MHz, DMSO) δ 6.48-6.46 (m, 3H), 6.38 (d, J = 2.6 Hz, 1H), 6.35 (t, J = 2.3 Hz, 1H), 5.04 (d, J = 8.5 Hz, 1H), 4.56 (dd, J = 14.1 Hz, 2 H) 4.06-4.01 (m, 1H), 3.74 (s, 3H), 3.72 (s, 3H), 3.70 (s, 6H), 3.46 (s, 2H), 3.35 (t, J = 6.74 Hz, 2H), 3.26-3.16 (m, 2H), 3.20 (s, 3H), 2.70-2.60 (m, 2H), 2.49-2.39 (m, 2H), 1.89-1.78 (m, 2H), 1.54-1.50 (m, 1H), 1.40-1.36 (m, 1H), 1.26 (d, J = 7.3 Hz, 3H), |
| 3 | 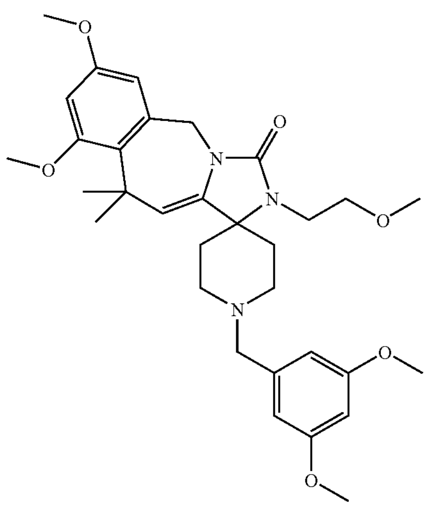 | 819544 Salt free | NMR $^1$H (400 MHz, CDCl$_3$) δ 6.52-6.50 (m, 2H), 6.46-6.45 (m, 2H), 6.38-6.37 (m, 1H), 4.69 (s, 1H), 4.62 (s, 2H), 3.80 (s, 6H), 3.79 (s, 3H), 3.76 (s, 3H), 3.53-3.50 (m, 4H), 3.40-3.37 (m, 2H), 3.35 (s, 3H), 2.78-2.75 (m, 2H), 2.58-2.55 (m, 2H), 2.01-1.97 (m, 2H), 1.66 (s, 6H), 1.67-1.62 (m, 2H) |

TABLE 1-continued

Analytical Data for Exemplary Compounds of Formula I

| Example # | Structure | ER-# | Analytical Data |
|---|---|---|---|
| 4 | 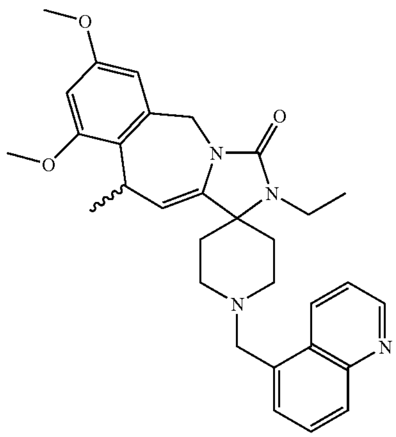 | 819592 Salt free | NMR $^1$H (400 MHz, DMSO) δ 8.89-8.87 (m, 1H), 8.70 (d, J = 8.8 Hz, 1H), 7.92 (d, J = 8.2 Hz, 1H), 7.67 (t, J = 7.9 Hz, 1H), 7.56-7.53 (m, 2H), 6.48-6.47 (m, 1H), 6.38-6.37 (m, 1H), 5.10 (d, J = 8.2 Hz, 1H), 4.56 (dd, J = 14.2 Hz, 2H), 4.09-4.04 (m, 1H), 3.99 (s, 2H), 3.75 (s, 3H), 3.72 (s, 3H), 3.12-3.03 (m, 2H), 2.78-2.55 (m, 4H), 1.83-1.71 (m, 2H), 1.57-1.53 (m, 1H), 1.40-1.37 (m, 1H), 1.28 (d, J = 7.3 Hz, 3H), 1.00 (t, J = 6.9 Hz, 3H) |
| 5 | 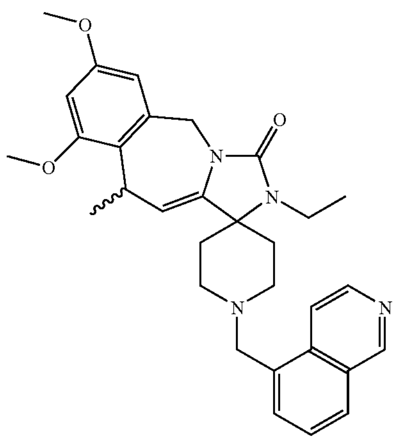 | 819593 Salt free | NMR $^1$H (400 MHz, DMSO) δ 8.85-8.84 (m, 1H), 8.33 (d, J = 8.2 Hz, 1H), 7.98-7.93 (m, 1H), 7.87 (s, 1H), 7.75-7.73 (m, 1H), 7.51-7.48 (m, 1H), 6.47 (s, 1H), 6.38 (s, 1H), 5.05 (d, J = 8.2 Hz, 1H), 4.55, (dd, J = 14.2 Hz, 2H), 4.05-4.01 (m, 1H), 3.74 (s, 5H), 3.72 (s, 3H), 3.18-3.11 (m, 2H), 2.75-2.52 (m, 4H), 1.91-1.82 (m, 2H), 1.58-1.55 (m, 1H), 1.43-1.40 (m, 1H), 1.26 (d, J = 7.3 Hz, 3H), 1.03 (t, J = 6.7 Hz, 3H) |
| 6 | 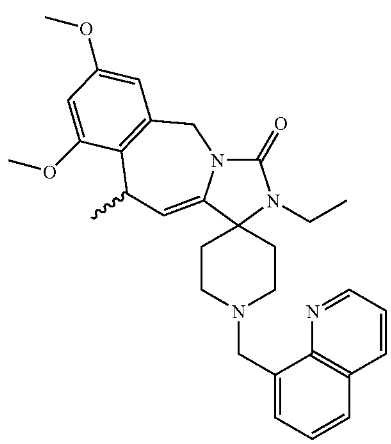 | 819594 Salt free | NMR $^1$H (400 MHz, DMSO) δ 8.91-8.90 (m, 1H), 8.36-8.34 (m, 1H), 7.87-7.85 (m, 2H), 7.59 (t, J = 7.8 Hz, 1H), 7.54-7.51 (m, 1H), 6.48-6.47 (m, 1H), 6.38-6.37 (m, 1H), 5.07 (d, J = 8.5 Hz, 1H), 4.55 (dd, J = 14.2 Hz, 2H), 4.25 (s, 2H), 4.06-4.02 (m, 1H), 3.74 (s, 3H), 3.72 (s, 3H), 3.19-3.12 (m, 2H), 2.86-2.60 (m, 4H), 1.96-1.85 (m, 2H), 1.60-1.57 (m, 1H), 1.45-1.42 (m, 1H), 1.26 (d, J = 7.3 Hz, 3H), 1.04 (t, J = 6.9 Hz, 3H) |

TABLE 1-continued

Analytical Data for Exemplary Compounds of Formula I

| Example # | Structure | ER-# | Analytical Data |
|---|---|---|---|
| 7 | 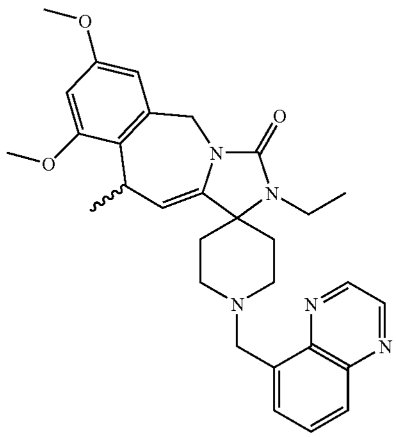 | 819595 Salt free | NMR ¹H (400 MHz, DMSO) δ 8.96-8.95 (m, 2H), 8.00-7.93 (m, 2H), 7.87-7.83 (m, 1H), 6.48-6.47 (m, 1H), 6.38-6.37 (m, 1H), 5.06 (d, J = 8.5 Hz, 1H), 4.55, (dd, J = 14.1 Hz, 2H), 4.24 (s, 2H), 4.05-4.01 (m, 1H), 3.74 (s, 3H), 3.72 (s, 3H), 3.19-3.11 (m, 2H), 2.79-2.60 (m, 4H), 1.95-1.84 (m, 2H), 1.59-1.56 (m, 1H), 1.44-1.41 (m, 1H), 1.26 (d, J = 7.0 Hz, 3H), 1.03 (t, J = 7.0 Hz, 3H), |
| 8 | 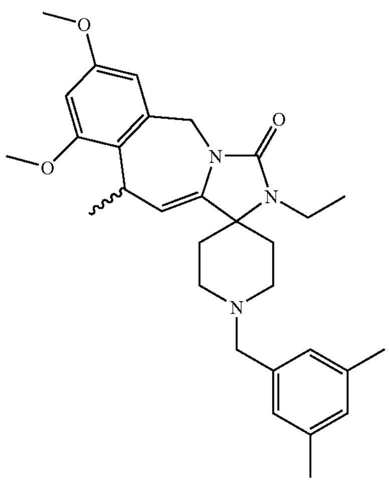 | 819597 Salt free | NMR ¹H (400 MHz, DMSO) δ 6.89 (s, 2H), 6.85 (s, 1H), 6.48-6.47 (m, 1H), 6.38-6.37 (m, 1H), 5.00 (d, J = 8.5 Hz, 1H), 4.55 (dd, J = 14.2 Hz, 2H), 4.04-4.00 (m, 1H), 3.74 (s, 3H), 3.72 (s, 3H), 3.44 (s, 2H), 3.17-3.08 (m, 2H), 2.68-2.57 (m, 2H), 2.51-2.38 (m, 2H), 2.23 (s, 6H), 1.88-1.75 (m, 2H), 1.56-1.52 (m, 1H), 1.40-1.37 (m, 1H), 1.26 (d, J = 7.0 Hz, 3H), 1.02 (t, J = 7.0 Hz, 3H), |
| 9 | 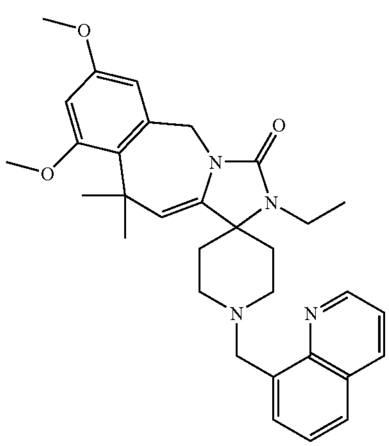 | 819604 Salt free | NMR ¹H (400 MHz, DMSO) δ 8.91-8.92 (m, 1H), 8.37-8.35 (m, 1H), 7.89-7.82 (m, 2H), 7.62-7.51 (m, 2H), 6.50-6.49 (m, 1H), 6.38-6.37 (m, 1H), 4.56 (s, 1H), 4.44 (s, 2H), 4.28 (s, 2H), 3.71 (s, 3H), 3.70 (s, 3H), 3.19-3.16 (m, 2H), 2.85-2.80 (m, 2H), 2.65-2.59 (m, 2H), 1.98-1.90 (m, 2H), 1.58-1.52 (m, 2H), 1.50 (s, 6H), 1.08-1.03 (m, 3H) |

TABLE 1-continued

Analytical Data for Exemplary Compounds of Formula I

| Example # | Structure | ER-# | Analytical Data |
|---|---|---|---|
| 10 | 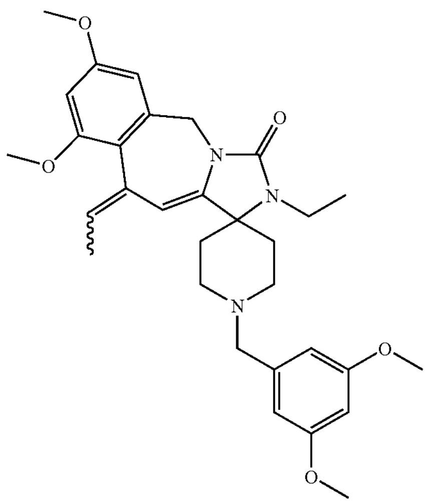 | 819651 Salt free | NMR $^1$H (400 MHz, CD$_3$OD) δ 6.56-6.49 (m, 4H), 6.44-6.42 (m, 1H), 5.73-5.72; 5.60-5.59 (2m, 1H), 5.70-5.68; 5.54-5.52 (2m, 1H), 4.54 (dd, J = 13.6 Hz, 2H), 3.80-3.65 (m, 14H), 3.21-3.18 (m, 2H), 2.89-2.61 (m, 4H), 2.10-1.94 (m, 2H), 1.76-1.74 (m, 2H), 1.50-1.48; 1.32-1.28 (2m, 3H), 1.18-1.12 (m, 3H) |
| 11 | 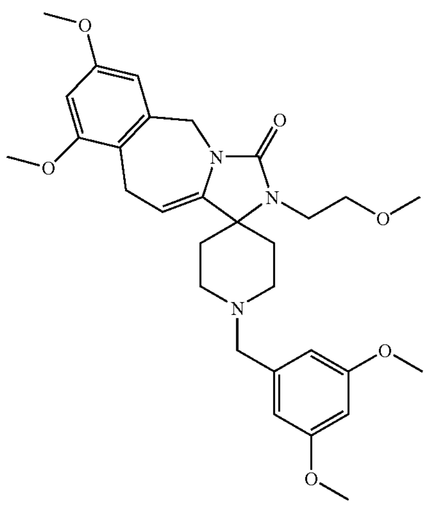 | 819673 Salt free | NMR $^1$H (400 MHz, CD$_3$OD) δ 6.55-6.54 (m, 2H), 6.50-6.49 (m, 1H), 6.46-6.45 (m, 1H), 6.41 (br, 1H), 5.08 (t, J = 6.2 Hz, 1H), 4.73 (s, 2H), 3.79 (s, 3H), 3.77 (s, 9H), 3.61-3.57 (m, 4H), 3.45 (t, J = 6.2 Hz, 2H), 3.33-3.31 (m, 2H), 2.91-2.82 (m, 2H), 2.66-2.56 (m, 2H), 2.15 (s, 3H), 2.01-1.96 (m, 2H), 1.60-1.56 (m, 2H), |
| 12 | 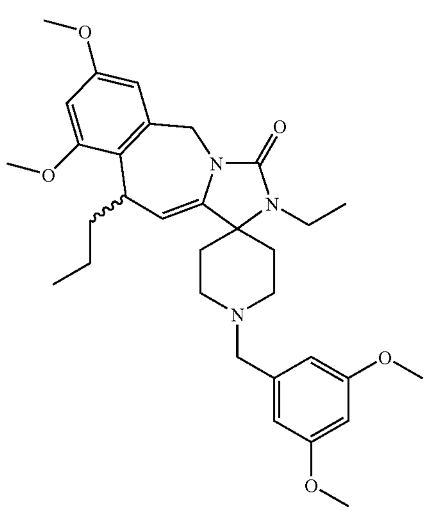 | 819626 Salt free | NMR $^1$H (400 MHz, CD$_3$OD) δ 6.71-6.62 (m, 3H), 6.47-6.46 (m, 1H), 3.69-6.38 (m, 1H), 4.79-4.78 (m, 2H), 4.38 (br, 1H), 4.12-4.10 (m, 1H), 3.82-3.56 (m, 16H), 3.64-3.56 (m, 2H), 3.48-3.45 (m, 2H), 2.58-2.43 (m, 2H), 2.22-2.05 (m, 2H), 1.43-1.41 (m, 4H), 1.18-1.15 (m, 6H) |

TABLE 1-continued

Analytical Data for Exemplary Compounds of Formula I

| Example # | Structure | ER-# | Analytical Data |
|---|---|---|---|
| 13 | 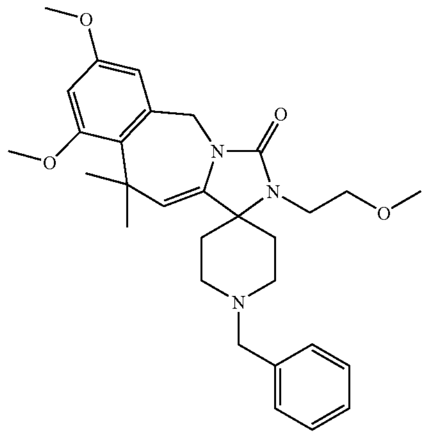 | 819641 Salt free | NMR ¹H (400 MHz, CD₃OD) δ 7.37-7.28 (m, 5H), 6.51 (d, J = 2.6 Hz, 1H), 6.43 (d, J = 2.6 Hz, 1H), 4.67 (s, 1H), 4.54 (s, 2H), 3.78 (s, 3H), 3.76 (s, 3H), 3.69 (s, 2H), 3.51-3.48 (m, 2H), 3.39-3.35 (m, 2H), 3.32 (s, 3H), 2.85-2.82 (m, 2H), 2.70-2.61 (m, 2H), 2.09-2.01 (m, 2H), 1.65-1.60 (m, 2H), 1.59 (s, 6H) |
| 14 | 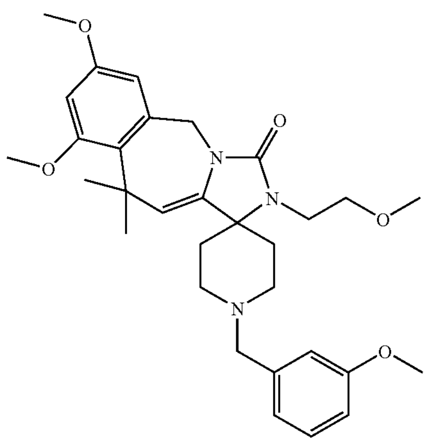 | 819647 Salt free | NMR ¹H (400 MHz, CD₃OD) δ 7.27 (t, J = 7.9 Hz, 1H), 6.93-6.91 (m, 2H), 6.88-6.86 (m, 1H), 6.52 (d, J = 2.6 Hz, 1H), 6.43 (d, J = 2.9 Hz, 1H), 4.68 (s, 1H), 4.54 (s, 2H), 3.81 (s, 3H), 3.78 (s, 3H), 3.76 (s, 3H), 3.66 (s, 2H), 3.52-3.48 (m, 2H), 3.39-3.36 (m, 2H), 3.33 (s, 3H), 2.85-2.81 (m, 2H), 2.69-2.62 (m, 2H), 2.09-2.01 (m, 2H), 1.64-1.60 (m, 2H), 1.59 (s, 6H) |
| 15 | 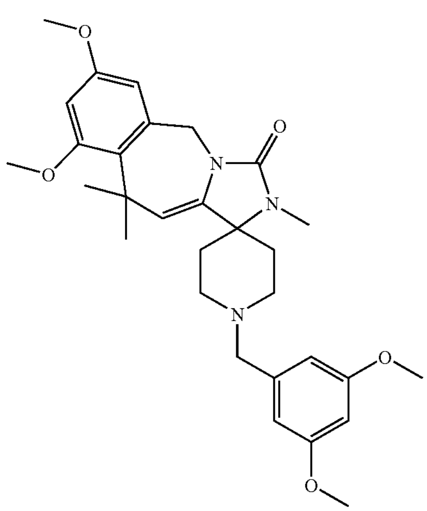 | 819658 Salt free | NMR ¹H (400 MHz, CD₃OD) δ 6.54-6.53 (m, 2H), 6.51-6.50 (m, 1H), 6.44-6.42 (m, 2H), 4.67 (s, 1H), 4.55 (s, 2H), 3.79 (s, 6H), 3.78 (s, 3H), 3.76 (s, 3H), 3.62 (s, 2H), 2.85 (s, 3H), 2.83-2.77 (m, 2H), 2.75-2.69 (m, 2H), 2.14-2.06 (m, 2H), 1.67-1.61 (m, 2H). 1.60 (s, 6H) |

TABLE 1-continued

Analytical Data for Exemplary Compounds of Formula I

| Example # | Structure | ER-# | Analytical Data |
| --- | --- | --- | --- |
| 16 | 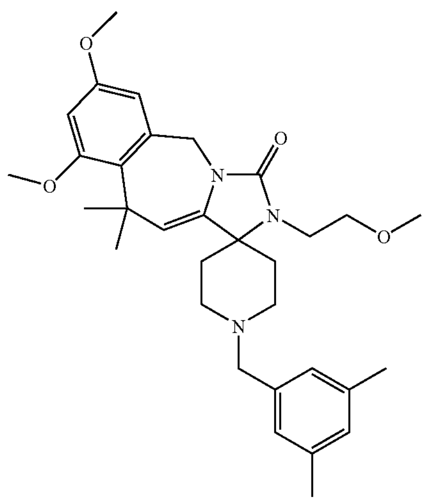 | 819659 Salt free | NMR $^1$H (400 MHz, CD$_3$OD) δ 6.96 (s, 3H), 6.51 (d, J = 2.6 Hz, 1H), 6.43 (d, J = 2.6 Hz, 1H), 4.63 (s, 1H), 4.54 (s, 2H), 3.77 (s, 3H), 3.46 (s, 3H), 3.62 (s, 2H), 3.51-3.48 (m, 2H), 3.39-3.36 (m, 2H), 3.32 (s, 3H), 2.83-2.77 (m, 2H), 2.69-2.62 (m, 2H), 2.31 (s, 6H), 2.11-2.01 (m, 2H), 1.64-1.59 (m, 2H), 1.57 (s, 6H), |
| 17 | 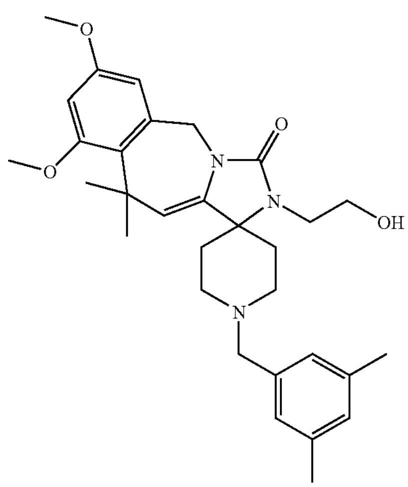 | 819660 Salt free | NMR $^1$H (400 MHz, CD$_3$OD) δ 6.96 (s, 3H), 6.50 (d, J = 2.6 Hz, 1H), 6.43 (d, J = 2.6 Hz, 1H), 4.64 (s, 1H), 4.54 (s, 2H), 3.77 (s, 3H), 3.75 (s, 3H), 3.66-3.62 (m, 2H), 3.33-3.30 (m, 2H), 2.83-2.80 (m, 2H), 2.69-2.61 (m, 2H), 2.31 (s, 6H), 2.07-1.99 (m, 2H), 1.66-1.62 (m, 2H), 1.57 (s, 6H) |
| 18 | 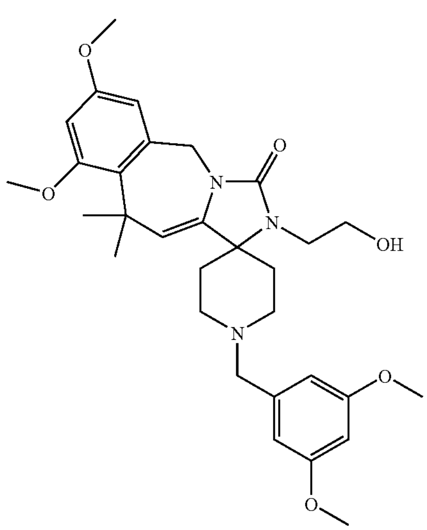 | 819657 Salt free | NMR $^1$H (400 MHz, CD$_3$OD) δ 6.53-6.52 (m, 2H), 6.51-6.50 (m, 1H), 6.44-6.42 (m, 2H), 4.70 (s, 1H), 4.55 (2H), 3.79 (s, 6H), 3.77 (s, 3H), 3.76 (s, 3H), 3.65 (t, J = 6.4 Hz, 2H), 3.62 (s, 2H), 3.33-3.31 (m, 2H), 2.85-2.82 (m, 2H), 2.70-2.64 (m, 2H), 2.08-2.00 (m, 2H), 1.67-1.64 (m, 2H), 1.61 (s, 6H) |

TABLE 1-continued

Analytical Data for Exemplary Compounds of Formula I

| Example # | Structure | ER-# | Analytical Data |
|---|---|---|---|
| 19 | 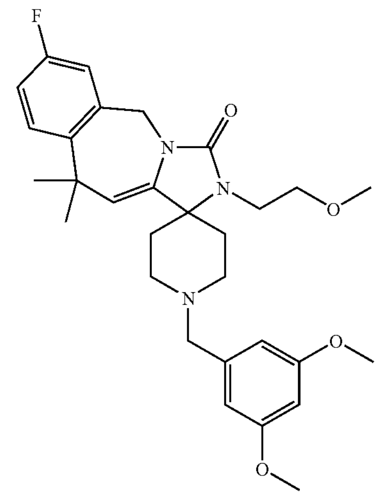 | ER-819672 Salt free | NMR $^1$H (400 MHz, CDCl$_3$) δ 7.32-2.27 (m, 1H), 7.02-6.99 (m, 2H), 6.51 (d, J = 2.3 Hz, 2H), 6.38 (t, J = 2.3 Hz, 1H), 4.82 (s, 2H), 4.78 (s, 1H), 3.81 (s, 6H), 3.52 (s, 2H), 3.52-3.48 (m, 2H), 3.39-3.35 (m, 2H), 3.34 (s, 3H), 2.77-2.72 (m, 2H), 2.54-2.47 (m, 2H), 1.99-1.91 (m, 2H), 1.62-1.57- (m, 2H), 1.55 (s, 6H) |
| 20 | 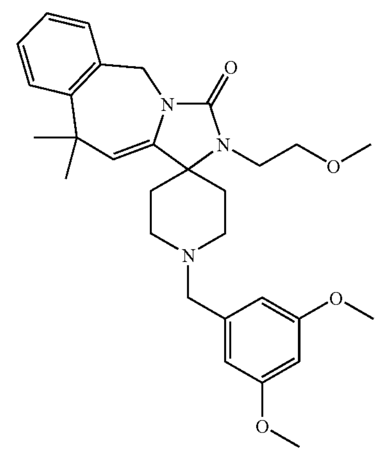 | 819677 Salt free | NMR $^1$H (400 MHz, CDCl$_3$) δ 7.37-7.34 (m, 1H), 7.31-7.27 (m, 2H), 7.23-7.19 (m, 1H), 6.51 (d, J = 2.3 Hz, 2H), 6.38 (t, J = 2.3 Hz, 1H), 4.88 (s, 2H), 4.78 (s, 1H), 3.81 (s, 6H), 3.54-3.48 (m, 4H), 3.39-3.34 (m, 2H), 3.33 (s, 3H), 2.78-2.72 (m, 2H), 2.56-2.49 (m, 2H), 1.99-1.91 (m, 2H), 1.64-1.58 (m, 2H), 1.57 (s, 6H) |
| 21 | 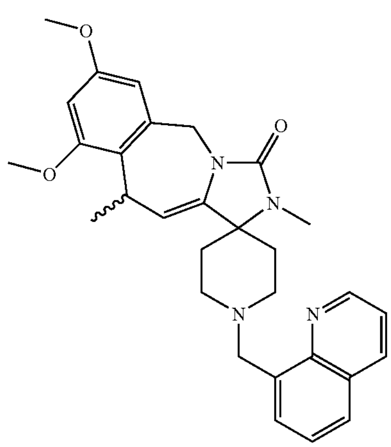 | 819689 Salt free | NMR $^1$H (400 MHz, DMSO) δ 8.92-8.90 (m, 1H), 8.36-8.34 (m, 1H), 7.87-7.83 (m, 2H), 7.61-7.60 (m, 1H), 7.53-7.51 (m, 1H), 6.47 (m, 1H), 6.38 (m, 1H), 5.06 (d, J = 8.5 Hz, 1H), 4.57 (dd, J = 14.3 Hz, 2H), 4.24 (s, 2H), 4.06-4.02 (m, 1H), 3.74 (s, 3H), 3.71 (s, 3H), 2.81-2.63 (m, 4H), 2.73 (s, 3H), 2.00- 1.92 (m, 2H), 1.59-1.56 (m, 1H), 1.44-1.40 (m, 1H), 1.26 (d, J = 7.3 Hz, 3H) |

TABLE 1-continued

Analytical Data for Exemplary Compounds of Formula I

| Example # | Structure | ER-# | Analytical Data |
|---|---|---|---|
| 22 | 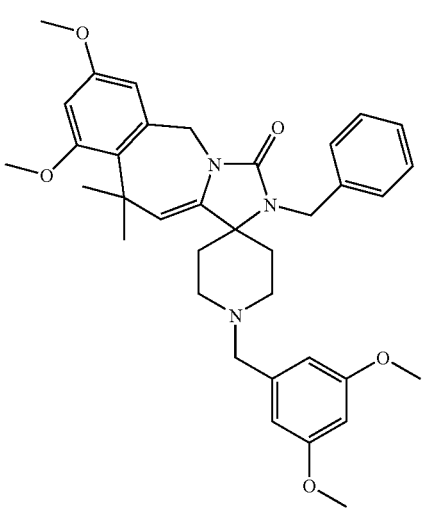 | 819662 Salt free | M/Z (ES+)<br>Calc.: 597.3<br>Found: 598.3 (M + H)<br>Analytical HPLC:<br>Method A1<br>Xterra MS C18 (4.6 × 100 mm) 5 um<br>Retention time: 9.98 min |
| 23 | 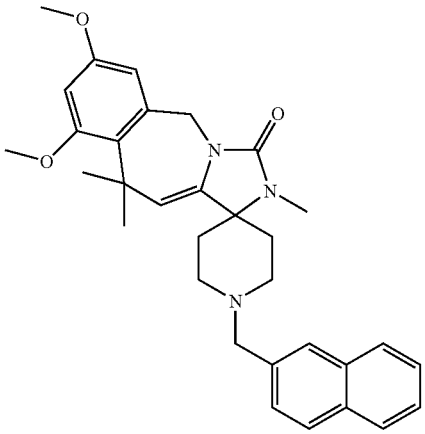 | 819627 TFA salt | M/Z (ES+)<br>Calc.: 511.3<br>Found: 512.4 (M + H)<br>Analytical HPLC:<br>Method A2<br>Xterra MS C18 (4.6 × 100 mm) 5 um<br>Retention time: 6.80 min |
| 24 | 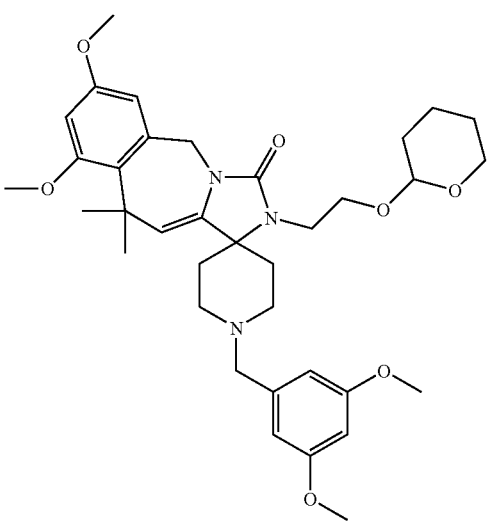 | 819661 Salt free | M/Z (ES+)<br>Calc.: 635.4<br>Found: 636.4 (M + H)<br>Analytical HPLC:<br>Method A1<br>Xterra MS C18 (4.6 × 100 mm) 5 um<br>Retention time: 9.54 min |

TABLE 1-continued

Analytical Data for Exemplary Compounds of Formula I

| Example # | Structure | ER-# | Analytical Data |
|---|---|---|---|
| 25 | 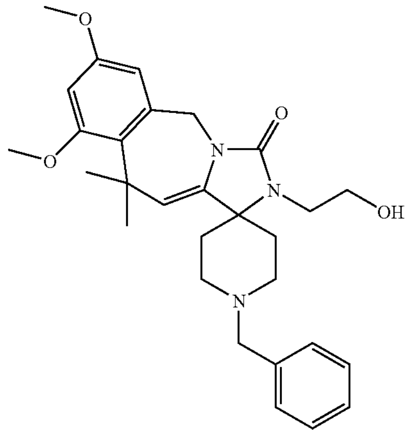 | 819642 Salt free | M/Z (ES+) Calc.: 491.3 Found: 492.4 (M + H) Analytical HPLC: Method A1 Xterra MS C18 (4.6 × 100 mm) 5 um Retention time: 7.28 min |
| 26 | 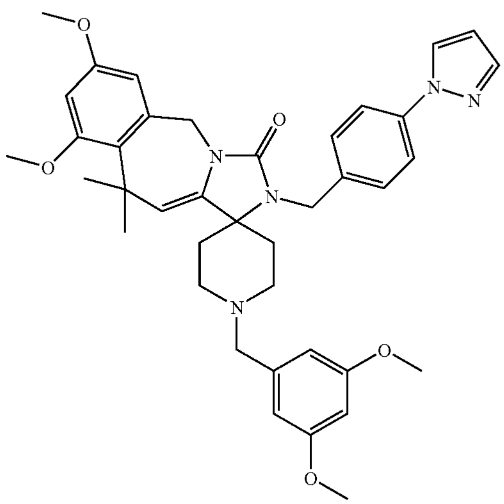 | 819663 Salt free | M/Z (ES+) Calc.: 663.3 Found: 664.7 (M + H) Analytical HPLC: Method A1 Xterra MS C18 (4.6 × 100 mm) 5 um Retention time: 9.60 min |
| 27 | 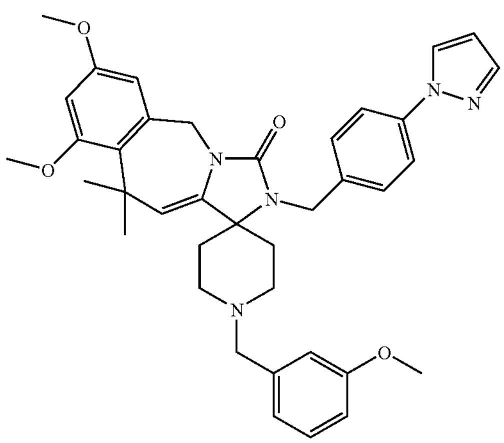 | 819650 Salt free | M/Z (ES+) Calc.: 633.3 Found: 634.4 (M + H) Analytical HPLC: Method A1 Xterra MS C18 (4.6 × 100 mm) 5 um Retention time: 9.72 min |

TABLE 1-continued
Analytical Data for Exemplary Compounds of Formula I
| Example # | Structure | ER-# | Analytical Data |
|---|---|---|---|
| 28 | 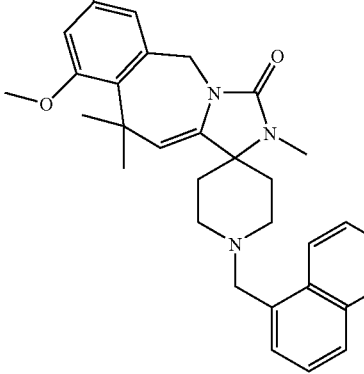 | 819637 TFA salt | M/Z (ES+) Calc.: 551.3 Found: 512.3 (M + H) Analytical HPLC: Method A2 Xterra MS C18 (4.6 × 100 mm) 5 um Retention time: 7.17 min |
| 29 | 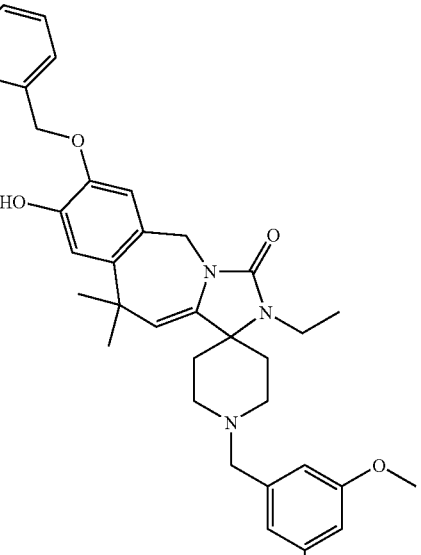 | 819718 TFA salt | M/Z (ES+) Calc.: 597.3 Found: 598.4 (M + H) |
| 30 | 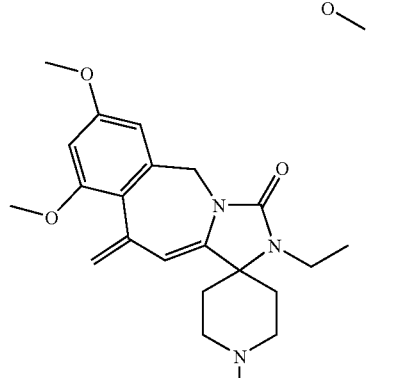 | 819703 TFA salt | M/Z (ES+) Calc.: 519.3 Found: 520.4 (M + H) |

TABLE 1-continued

Analytical Data for Exemplary Compounds of Formula I

| Example # | Structure | ER-# | Analytical Data |
|---|---|---|---|
| 31 | 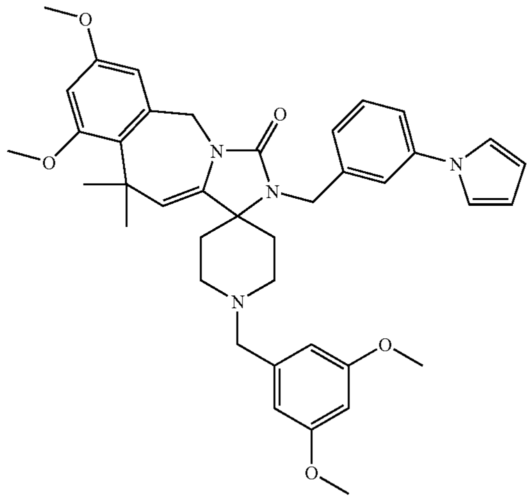 | 819590 Salt free | NMR ¹H (400 MHz, DMSO) δ 7.45 (s, 1H), 7.40-7.32 (m, 2H), 7.27 (m, 2H), 7.05 (d, J = 7.6 Hz, 1H), 6.49 (d, J = 2.3 Hz, 1H), 6.42 (s, 2H), 6.34-6.30 (m, 2H), 6.23 (s, 2H), 4.62-4.40 (m, 4H), 3.75-3.62 (m, 12H), 3.43 (s, 2H), 2.64-2.55 (m, 2H), 2.50-2.42 (m, 2H), 1.73-1.83 (m, 2H), 1.50-1.43 (m, 2H), 1.38 (s, 6H) |
| 32 | 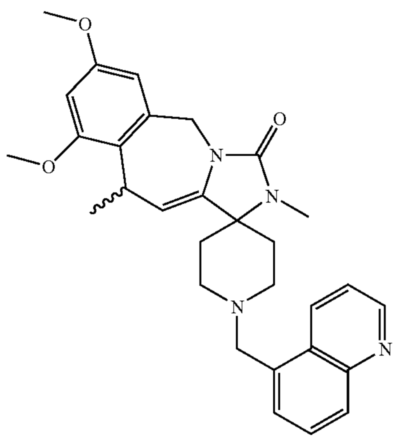 | 819688 Salt free | NMR ¹H (400 MHz, DMSO) δ 8.88-8.87 (m, 1H), 8.70-8.68 (m, 1H), 7.93-7.91 (m, 1H), 7.69-7.65 (m, 1H), 7.56-7.53 (m, 2H), 6.48-6.47 (m, 1H), 6.38-36.37 (m, 1H), 5.07 (d, J = 9.1 Hz, 1H), 4.65-4.48 (m, 2H), 4.08-4.04 (m, 1H), 3.99 (s, 2H), 3.75 (s, 3H), 3.71 (s, 3H), 2.75-2.58 (m, 7H), 1.89-1.80 (m, 2H), 1.54-1.51 (m, 1H), 1.37-1.34 (m, 1H), 1.27 (d, J = 7.3 Hz, 3H) |

EXAMPLES 33-106

Biological Activity

HEKT-bet-luc assay: This assay measures a T-bet dependent reporter (luciferase) activity in engineered HEK cells that express a human T-bet and a T-box responsive element driving luciferase reporter. HEKT-bet cells were plated at 2×10⁴/well in 96-well plate and compound was added into cell culture for 24 hours. Luciferase activity was measured by adding 50 μl of Steady-Glo reagent (Promega) and samples were read in Victor V reader (PerkinElmer). The activity of compound was determined by comparing compound treated samples to non-compound treated vehicle controls. The $IC_{50}$ values were calculated utilizing a maximum value corresponding to the amount of luciferase in the absence of a test compound and a minimum value corresponding to a test compound value obtained at maximum inhibition.

Determination of Normalized HEKT-bet IC50 values: Compounds were assayed in microtiter plates. Each plate included a reference compound which was ER-819544. The un-normalized $IC_{50}$ value for a particular compound was divided by the $IC_{50}$ value determined for the reference compound in the same microtiter plate to provide a relative potency value. The relative potency value was then multiplied by the established potency of the reference compound to provide the normalized HEKT-bet $IC_{50}$ value. In this assay, the established potency for ER-819544 was 0.035 μM. The $IC_{50}$ values provided herein were obtained using this normalization method.

Exemplary compounds of the present invention were assayed according to the methods set forth above in the HEKT-bet-luc assay described above. Table 2 below sets forth exemplary compounds of the present invention having an $IC_{50}$ of up to 5.0 μM as determined by the normalized HEKT-bet-luc assay described above.

TABLE 2

| | IC$_{50}$ Values of Exemplary Compounds | | |
|---|---|---|---|
| Example # | Structure | ER-Number | IC$_{50}$ (μm) |
| 33 | | 819543 | 0.015 |
| 34 | | 819549 | 0.015 |
| 35 | | 819543 | 0.015 |

TABLE 2-continued

| IC$_{50}$ Values of Exemplary Compounds | | | |
|---|---|---|---|
| Example # | Structure | ER-Number | IC$_{50}$ (μm) |
| 36 | | 819701 | 0.021 |
| 37 | | 819544 | 0.035 |
| 38 | | 819594 | 0.060 |

TABLE 2-continued

IC$_{50}$ Values of Exemplary Compounds

| Example # | Structure | ER-Number | IC$_{50}$ (μm) |
|---|---|---|---|
| 39 | 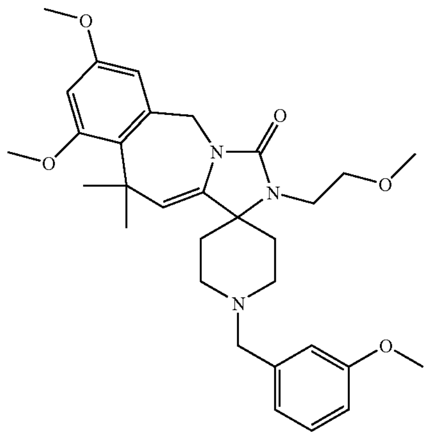 | 819647 | 0.064 |
| 40 | 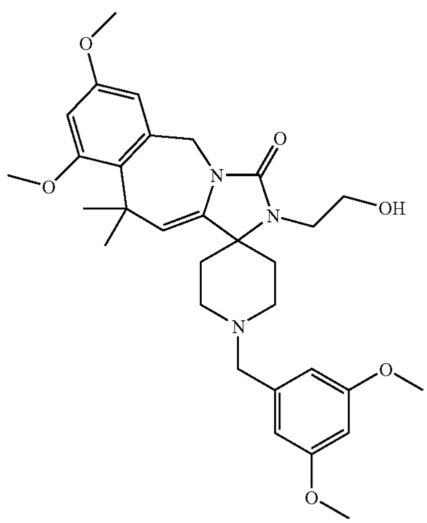 | 819657 | 0.065 |
| 41 | 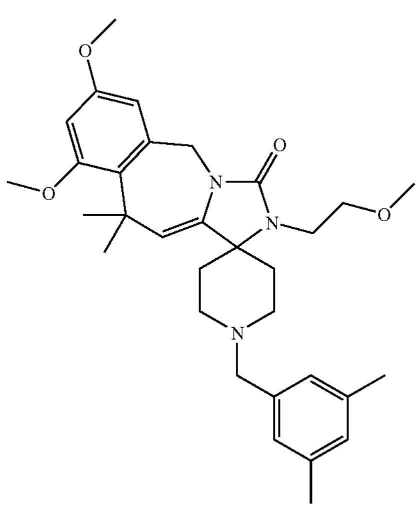 | 819659 | 0.068 |

TABLE 2-continued

IC$_{50}$ Values of Exemplary Compounds

| Example # | Structure | ER-Number | IC$_{50}$ (μm) |
|---|---|---|---|
| 42 | 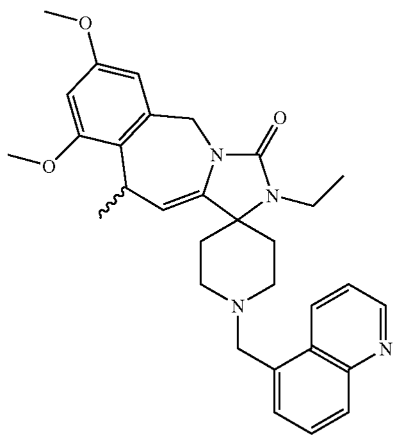 | 819592 | 0.086 |
| 43 | 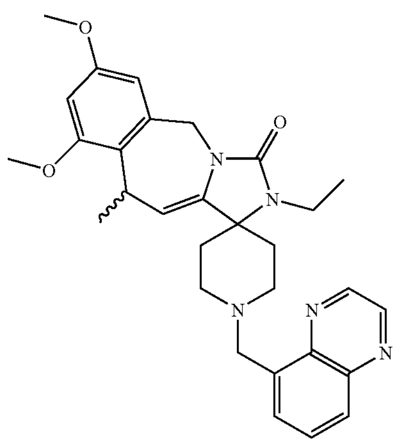 | 819595 | 0.090 |
| 44 | 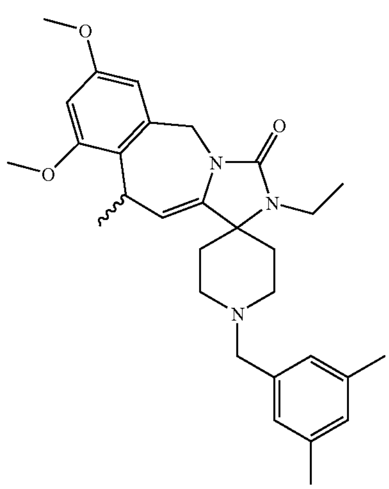 | 819597 | 0.090 |

TABLE 2-continued

| IC$_{50}$ Values of Exemplary Compounds | | | |
|---|---|---|---|
| Example # | Structure | ER-Number | IC$_{50}$ (μm) |
| 45 | | 819641 | 0.098 |
| 46 | | 819673 | 0.102 |
| 47 | | 819651 | 0.110 |

TABLE 2-continued

IC$_{50}$ Values of Exemplary Compounds

| Example # | Structure | ER-Number | IC$_{50}$ (μm) |
|---|---|---|---|
| 48 | 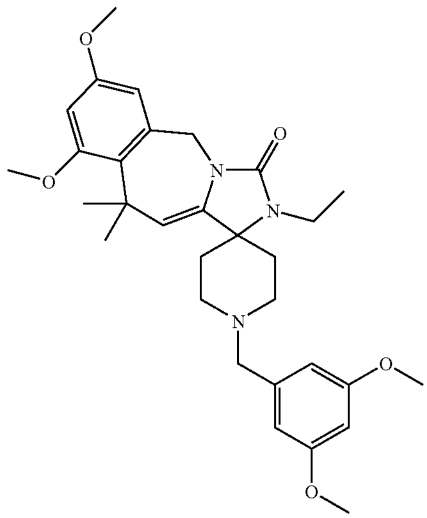 | 819583 | 0.112 |
| 49 | 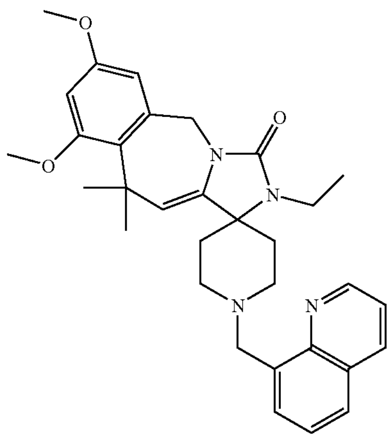 | 819604 | 0.120 |
| 50 | 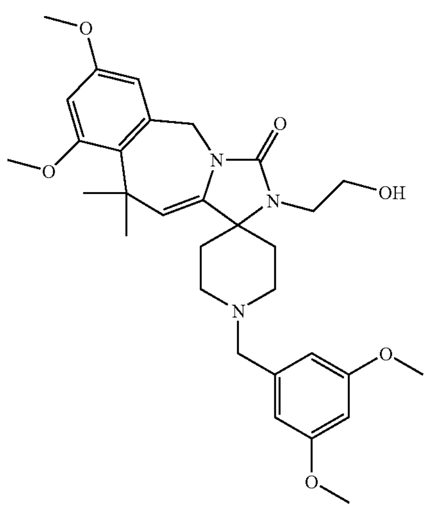 | 819657 | 0.124 |

TABLE 2-continued

IC$_{50}$ Values of Exemplary Compounds

| Example # | Structure | ER-Number | IC$_{50}$ (μm) |
|---|---|---|---|
| 51 | 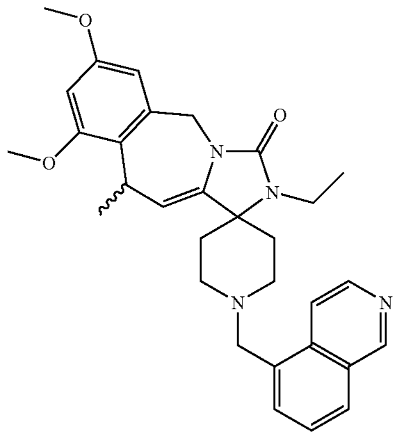 | 819593 | 0.140 |
| 52 | 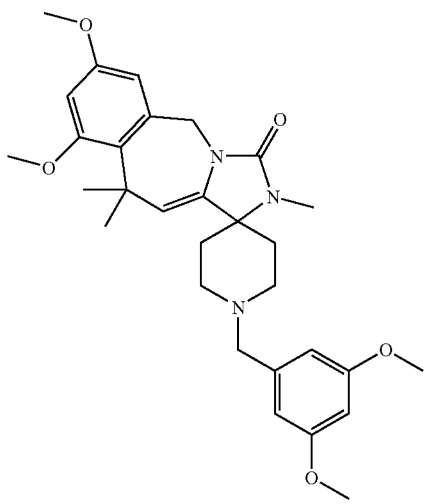 | 819658 | 0.141 |
| 53 | 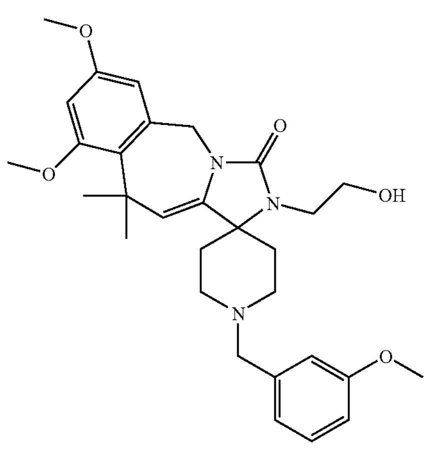 | 819648 | 0.147 |

TABLE 2-continued

IC$_{50}$ Values of Exemplary Compounds

| Example # | Structure | ER-Number | IC$_{50}$ (μm) |
|---|---|---|---|
| 54 | 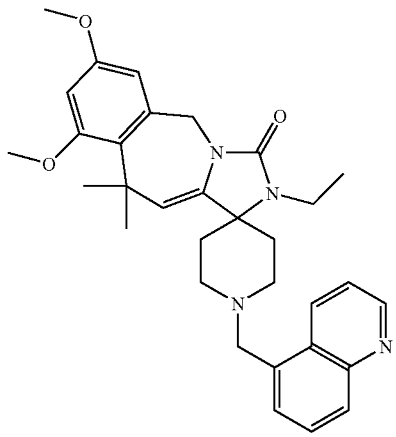 | 819602 | 0.150 |
| 55 | 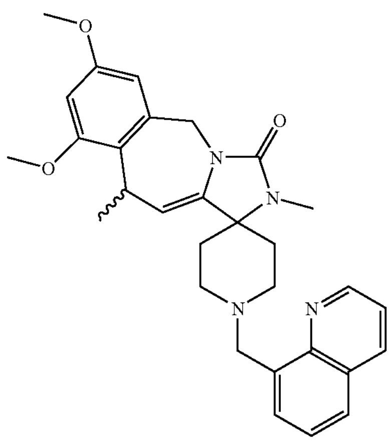 | 819689 | 0.169 |
| 56 | 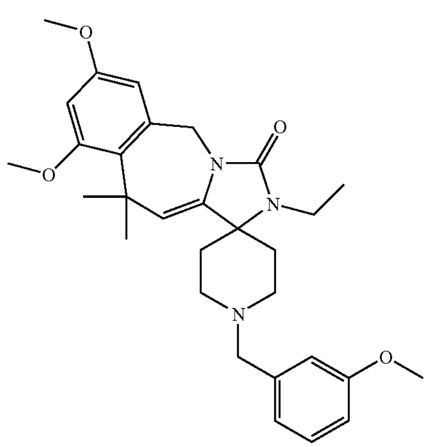 | 819646 | 0.184 |

TABLE 2-continued

IC$_{50}$ Values of Exemplary Compounds

| Example # | Structure | ER-Number | IC$_{50}$ (μm) |
|---|---|---|---|
| 57 | 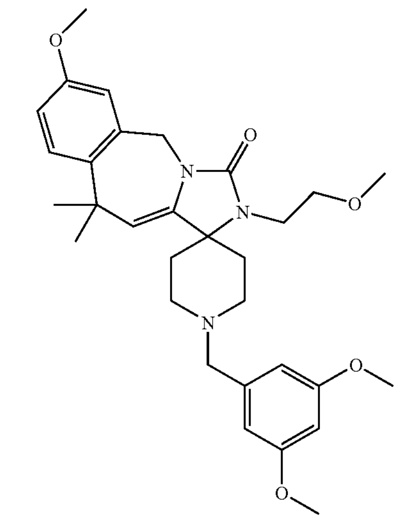 | 819655 | 0.204 |
| 58 | 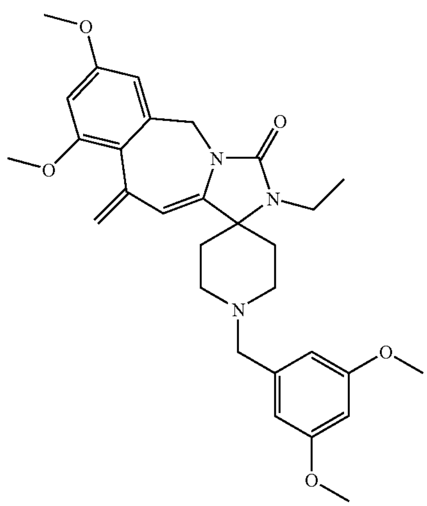 | 819703 | 0.247 |
| 59 | 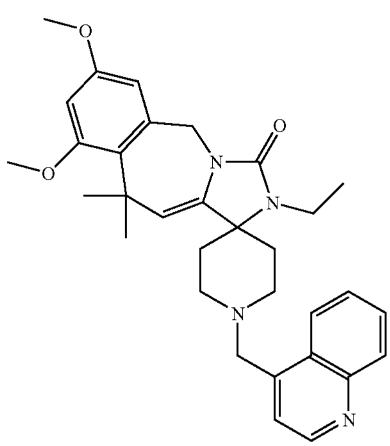 | 819601 | 0.260 |

TABLE 2-continued

IC₅₀ Values of Exemplary Compounds

| Example # | Structure | ER-Number | IC₅₀ (μm) |
|---|---|---|---|
| 60 | 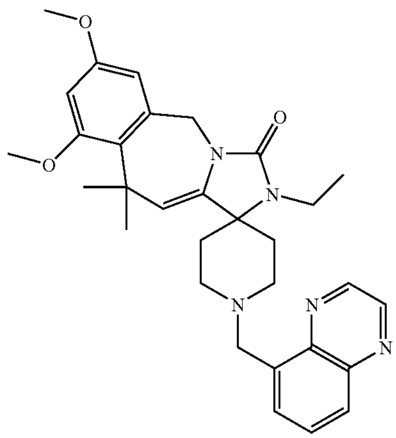 | 819605 | 0.260 |
| 61 | 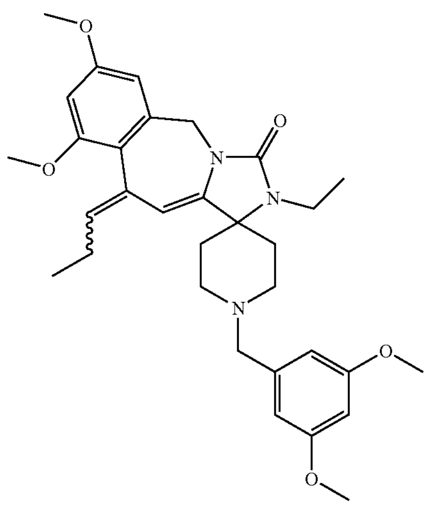 | 819652 | 0.270 |
| 62 | 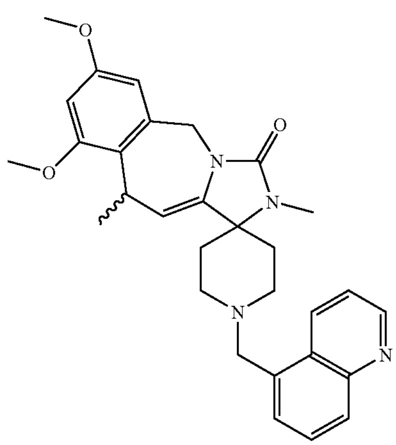 | 819688 | 0.288 |

TABLE 2-continued

| IC$_{50}$ Values of Exemplary Compounds | | | |
|---|---|---|---|
| Example # | Structure | ER-Number | IC$_{50}$ (μm) |
| 63 | | 819603 | 0.340 |
| 64 | | 819628 | 0.360 |
| 65 | | 819642 | 0.365 |

TABLE 2-continued

IC$_{50}$ Values of Exemplary Compounds

| Example # | Structure | ER-Number | IC$_{50}$ (μm) |
|---|---|---|---|
| 66 | 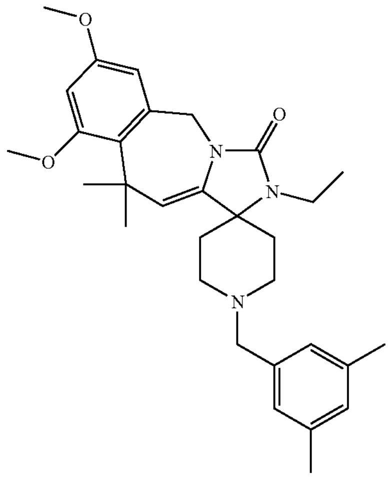 | 819607 | 0.500 |
| 67 | 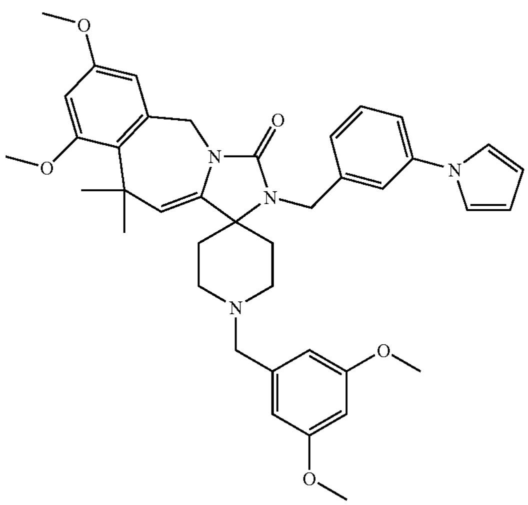 | 819590 | 0.514 |
| 68 | 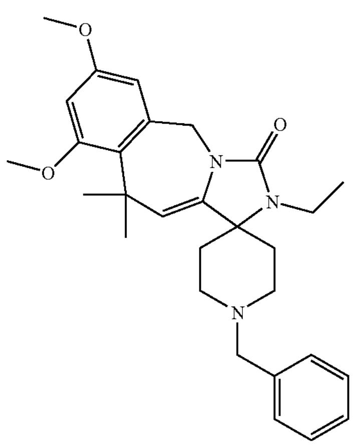 | 819640 | 0.542 |

TABLE 2-continued

IC$_{50}$ Values of Exemplary Compounds

| Example # | Structure | ER-Number | IC$_{50}$ (μm) |
|---|---|---|---|
| 69 | 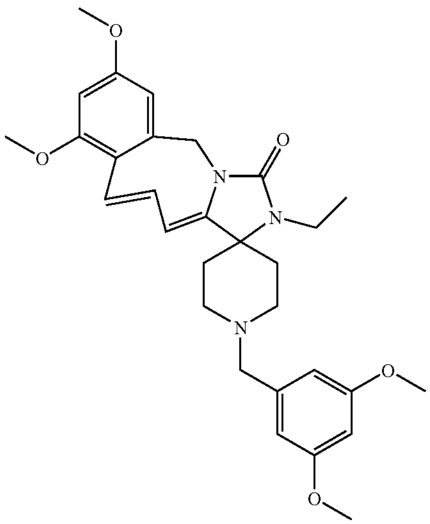 | 819702 | 0.600 |
| 70 | 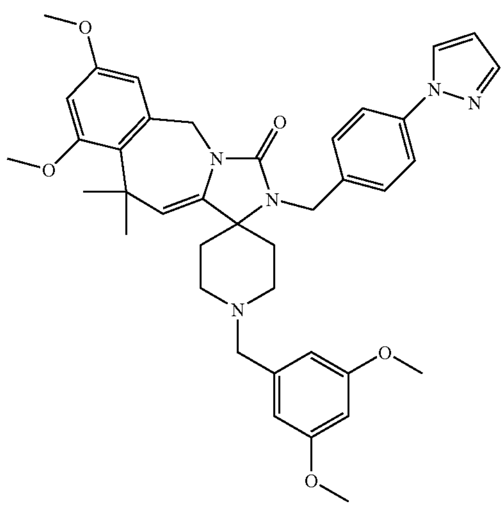 | 819663 | 0.637 |
| 71 | 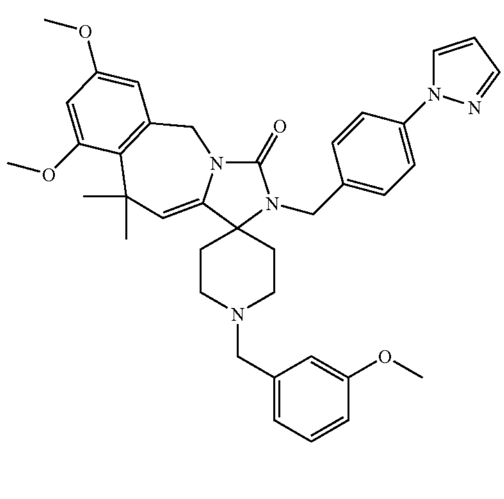 | 819650 | 0.669 |

TABLE 2-continued
IC$_{50}$ Values of Exemplary Compounds
| Example # | Structure | ER-Number | IC$_{50}$ (μm) |
|---|---|---|---|
| 72 | 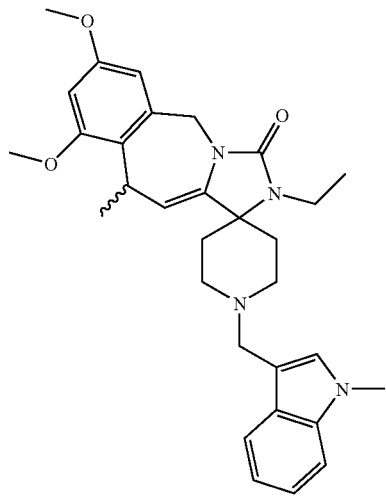 | 819596 | 0.720 |
| 73 | 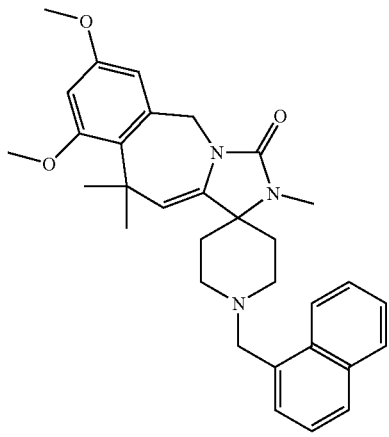 | 819637 | 0.734 |
| 74 | 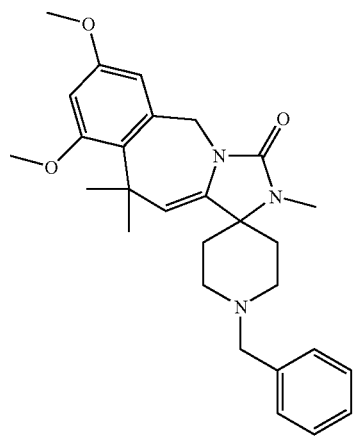 | 819629 | 0.840 |

TABLE 2-continued

| IC$_{50}$ Values of Exemplary Compounds | | | |
|---|---|---|---|
| Example # | Structure | ER-Number | IC$_{50}$ (μm) |
| 75 | | 819672 | 0.877 |
| 76 | | 819662 | 0.898 |
| 77 | | 819677 | 1.024 |

TABLE 2-continued

IC$_{50}$ Values of Exemplary Compounds

| Example # | Structure | ER-Number | IC$_{50}$ (μm) |
|---|---|---|---|
| 78 | 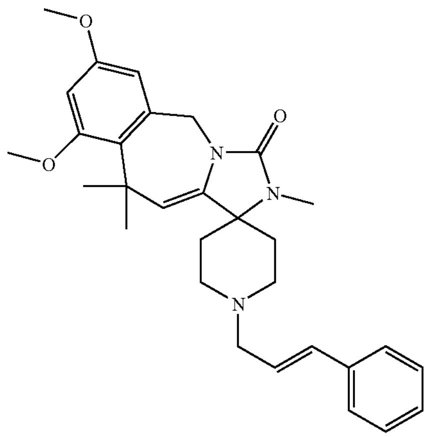 | 819634 | 1.150 |
| 79 | 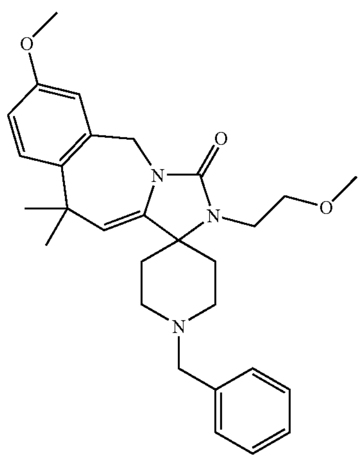 | 819613 | 1.310 |
| 80 | 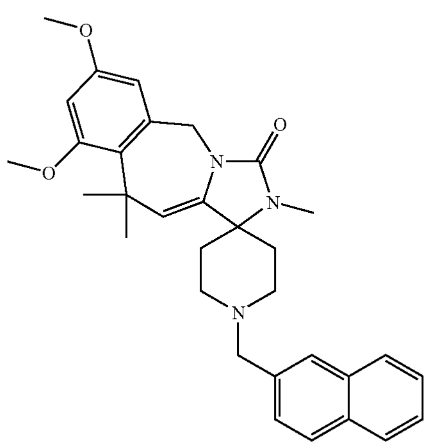 | 819627 | 1.600 |

TABLE 2-continued

| | IC$_{50}$ Values of Exemplary Compounds | | |
|---|---|---|---|
| Example # | Structure | ER-Number | IC$_{50}$ (μm) |
| 81 | | 819698 | 1.983 |
| 82 | | 819704 | 2.759 |
| 83 | | 819606 | 2.870 |

TABLE 2-continued
IC₅₀ Values of Exemplary Compounds
| Example # | Structure | ER-Number | IC₅₀ (μm) |
|---|---|---|---|
| 84 | 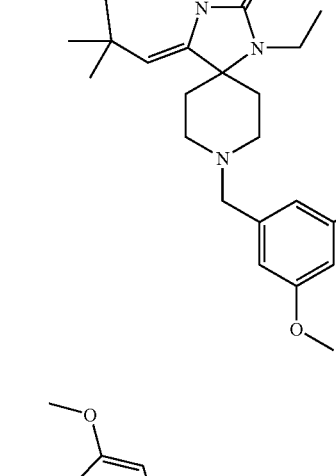 | 819708 | 3.599 |
| 85 | 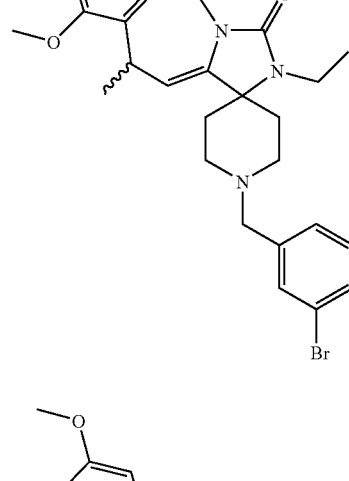 | 819599 | 4.710 |
| 86 | 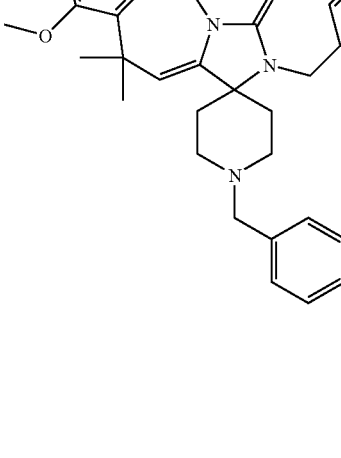 | 819649 | 4.945 |

TABLE 2-continued

IC$_{50}$ Values of Exemplary Compounds

| Example # | Structure | ER-Number | IC$_{50}$ (μm) |
|---|---|---|---|
| 87 | 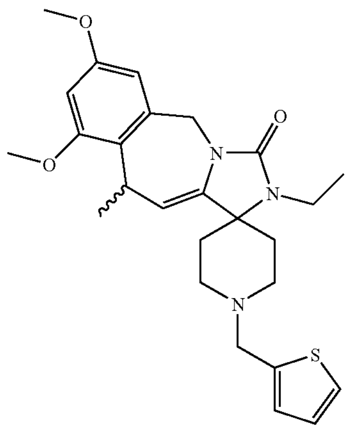 | 819556 | 0.166 |
| 88 | 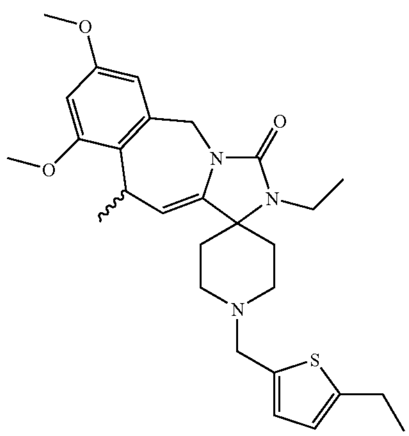 | 819557 | 0.51 |
| 89 | 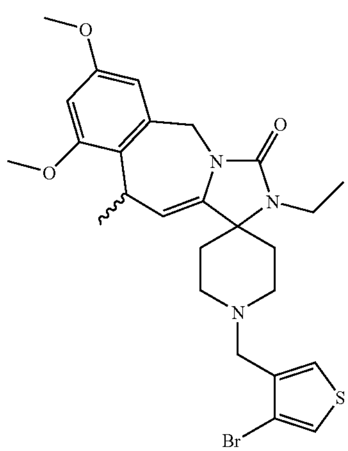 | 819558 | 0.74 |

TABLE 2-continued

| IC₅₀ Values of Exemplary Compounds | | | |
|---|---|---|---|
| Example # | Structure | ER-Number | IC₅₀ (μm) |
| 90 | | 819724 | 0.104 |
| 91 | | 819735 | 0.140 |
| 92 | | 819749 | 0.044 |

TABLE 2-continued
IC$_{50}$ Values of Exemplary Compounds
| Example # | Structure | ER-Number | IC$_{50}$ (μm) |
|---|---|---|---|
| 93 | 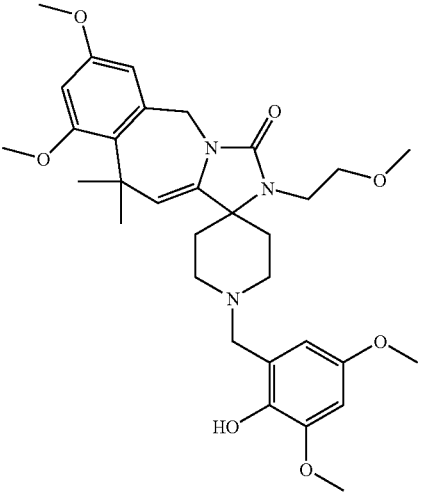 | 819750 | 0.041 |
| 94 | 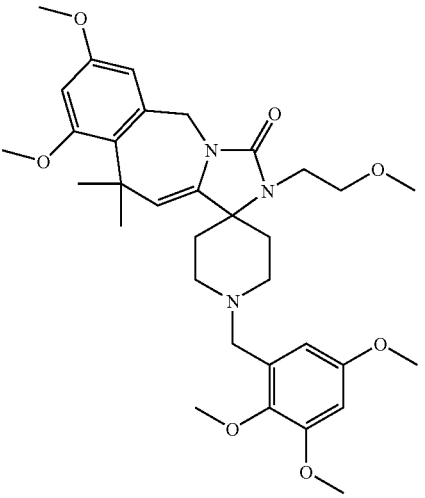 | 819752 | 0.071 |
| 95 | 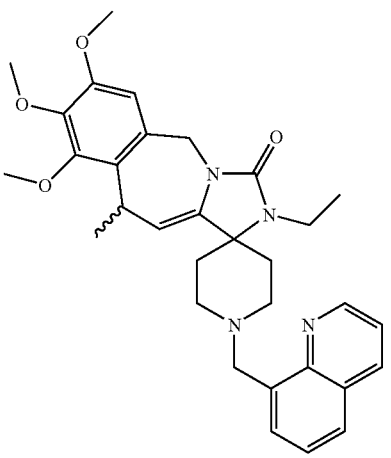 | 819755 | 0.053 |

TABLE 2-continued
| IC$_{50}$ Values of Exemplary Compounds | | | |
|---|---|---|---|
| Example # | Structure | ER-Number | IC$_{50}$ (μm) |
| 96 | 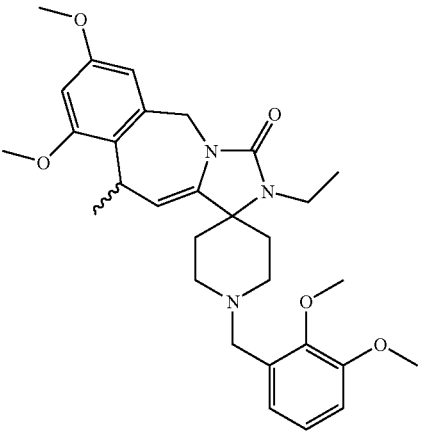 | 819767 | 0.148 |
| 97 | 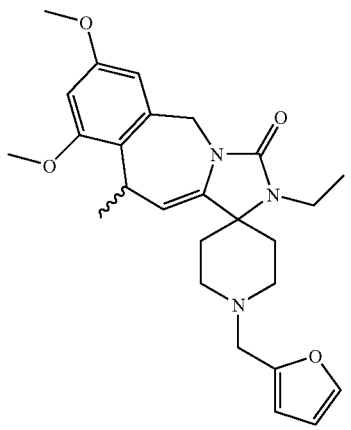 | 819768 | 0.183 |
| 98 | 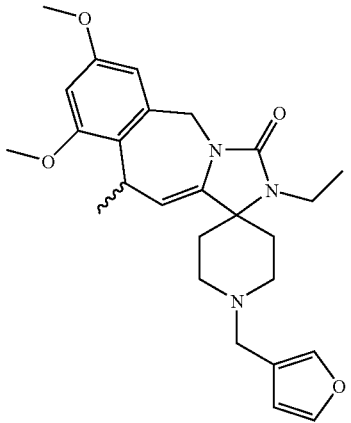 | 819769 | 0.190 |

TABLE 2-continued
IC$_{50}$ Values of Exemplary Compounds
| Example # | Structure | ER-Number | IC$_{50}$ (µm) |
|---|---|---|---|
| 99 | 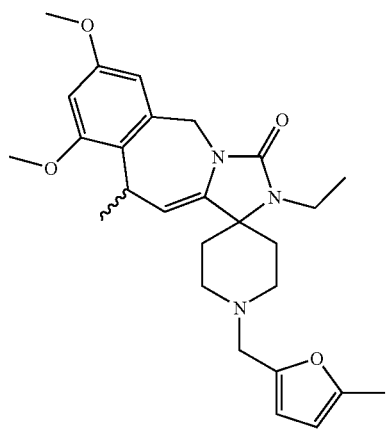 | 819770 | 0.267 |
| 100 | 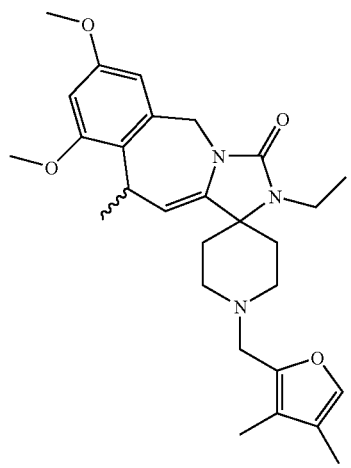 | 819771 | 0.205 |
| 101 | 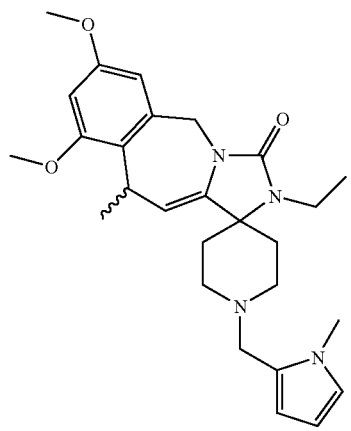 | 819772 | 0.103 |

TABLE 2-continued

| IC$_{50}$ Values of Exemplary Compounds | | | |
|---|---|---|---|
| Example # | Structure | ER-Number | IC$_{50}$ (μm) |
| 102 | | 819582 | 0.01 |
| 103 | | 819777 | 0.11 |
| 104 | | 819991 | 0.12 |

TABLE 2-continued

IC$_{50}$ Values of Exemplary Compounds

| Example # | Structure | ER-Number | IC$_{50}$ (μm) |
|---|---|---|---|
| 105 | 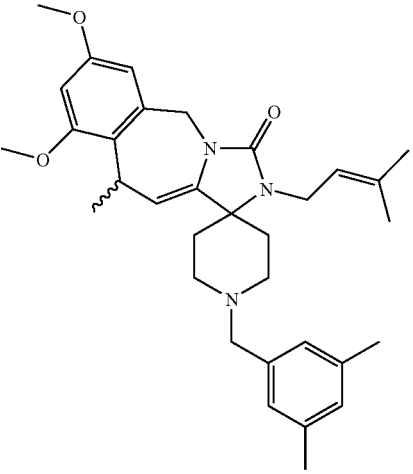 | 819995 | 0.33 |

PROPHETIC EXAMPLE 106

In vivo Biological Activity

Suppression of arthritis development in CIA. DBA1/J mice are immunized with bCII/CFA at day 0 then boosted at day 21 with bCII/IFA. Arthritis development is monitored over the course of study. The arthritis score is as follows: 0=normal paw, score of 1=1-2 digit inflamed paws; score of 2=3 digits or 1-2 digit+wrist or ankle inflamed, score of 3=hand+more than 2 digits inflamed; and score of 4=multiple digits (3-4)+ important wrist or ankle inflammation.

(A) Partial therapeutic evaluation of active compound: An active compound as described above is given by oral dosing once daily at the desired dosage from day 20 after induction of antibodies to collagen II but before disease development. (B) Full therapeutic evaluation of active compound: An active compound as described above is given after disease develops (from day 7 after the second immunization). (C) X-ray analysis of mouse paws from full therapeutic CIA study. X-ray score is the index of measurement of combination of osteopenia, bone erosion and new bone formation. (D) Representative X-ray radiographs.

PROPHETIC EXAMPLE 107

In vivo Biological Activity

Suppression of arthritis development in CAIA. BALB/c mice are injected i.v. with 1 mg of anti-type II collagen antibody at day 0, and 3 days later 25 μg of LPS is injected i.p. An active compound and methotrexate (MTX) is then given once daily PO from day 0 to day 7. Arthritis score and body weight is monitored over the course of study.

Other embodiments. While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A method of treating an autoimmune disease in a subject in need thereof, comprising administering to said subject a compound in a treatment effective amount;
    wherein said autoimmune disease is selected from the group consisting of systemic lupus erythematosus, type 1 diabetes mellitus, psoriasis, and atherosclerosis;
    wherein said compound is a compound of formula I:

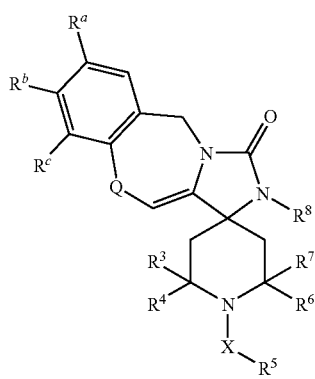

I wherein:
    Q is —C(R$^1$)(R$^2$)— or CH=CH— (cis or trans);
    R$^1$ and R$^2$ are independently selected from H, C$_{1-3}$ alkyl, C$_{2-4}$ alkenyl, or taken together are C$_{1-6}$ alkylidene or C$_{2-6}$ alkenylenidene;
    each of R$^3$, R$^4$, R$^6$, and R$^7$ is independently selected from hydrogen and methyl;
    X is methylene, ethylene, or propenylene;
    R$^5$ is phenyl, quinolinyl, isoquinolinyl, indolyl, furyl, thienyl, pyrazolyl, quinoxalinyl, naphthyl, or pyrrolyl, and substituted with between 0 and 5 substituents independently selected from C$_{1-3}$ alkyl, C$_{1-3}$ alkoxy, hydroxyl, C$_{1-3}$ alkylthio, cyclopropyl, cyclopropylmethyl, and halo;

R⁸ is H, methyl, ethyl, propenyl, (C$_{1-3}$ alkoxy)C$_{1-3}$ alkyl, (C$_{1-3}$ alkylthio)C$_{1-3}$ alkyl, C$_{1-3}$ hydroxyalkyl, phenyl, benzyl, furyl, pyrrolyl, imidazolyl, pyrazolyl, isothiazolyl, isooxazolyl, pyridyl, and thienyl;

wherein R⁸ is substituted with between 0 and 3 substituents independently selected from methyl, ethyl, halo, C$_{1-3}$ alkoxy, C$_{1-3}$ alkylthio, (C$_{1-3}$ alkoxy)C$_{1-3}$ alkyl, (C$_{1-3}$ alkylthio)C$_{1-3}$ alkyl, C$_{1-3}$ hydroxyalkyl, (C$_{1-3}$ mercaptoalkyl)phenyl, benzyl, furyl, imidazolyl, pyrazolyl, pyrrolyl, isothiazolyl, isooxazolyl, pyridyl, thienyl, pyranyl, dihydropyranyl, tetrahydropyranyl, and cyclopropyl; and each of R$^a$, R$^b$, and R$^c$ is independently selected from hydrogen, hydroxyl, methoxy, benzyloxy, fluoro, chloro, amino, methylamino, dimethylamino, and phenoxy;

or one pair selected from R$^a$ and R$^b$, and R$^b$ and R$^c$, taken together, is —O—(CH$_2$)—O— or —O—CH$_2$—CH$_2$—O—;

or a pharmaceutically acceptable salt, a C$_{1-6}$ alkyl ester or amide, or a C$_{2-6}$ alkenyl ester or amide thereof.

2. The method of claim 1, wherein:

Q is —C(R$^1$)(R$^2$)— or —CH═CH— (cis or trans);

R$^1$ and R$^2$ are independently selected from H, methyl, ethyl or propyl, or taken together are CH$_2$═, allylidene, propylidene, propenylidene, or ethylidene;

each of R$^3$, R$^4$, R$^6$, and R$^7$ is hydrogen;

X is methylene, ethylene, or propylene;

R$^5$ is phenyl, quinolinyl, isoquinolinyl, indolyl, furyl, thienyl, pyrazolyl, quinoxalinyl, naphthyl, or pyrrolyl, and substituted with between 0 and 3 substituents independently selected from methyl, methoxy, ethyl, hydroxyl, bromo, fluoro, and chloro;

R$^8$ is H, methyl, ethyl, propenyl, methoxyethyl, hydroxyethyl, or benzyl, wherein R$^8$ is substituted with between 0 and 3 substituents independently selected from methyl, ethyl, halo, C$_{1-3}$ alkoxy, 1, C$_{1-3}$ hydroxyalkyl, benzyl, furyl, imidazolyl, pyrazolyl, pyrrolyl, isothiazolyl, isooxazolyl, pyridyl, thienyl, pyranyl, dihydropyranyl, tetrahydropyranyl, and cyclopropyl;

or R$^a$ and R$^b$ taken together is —O—(CH$_2$)—O—;

each of R$^a$, R$^b$, and R$^c$ is independently selected from hydrogen, hydroxyl, methoxy, benzyloxy, fluoro, and chloro;

or a pharmaceutically acceptable salt thereof.

3. The method of claim 2, wherein:

R$^1$ and R$^2$ are independently selected from H and methyl, or taken together are CH$_2$═;

X is methylene, ethylene, or propylene;

R$^5$ is phenyl, quinolinyl, isoquinolinyl, indolyl, quinoxalinyl, naphthyl, or pyrrolyl, and substituted with between 0 and 3 substituents independently selected from, fluoro, methyl, methoxy, hydroxyl, and bromo;

R$^8$ is H, methyl, ethyl, hydroxyethyl, or benzyl; wherein benzyl is optionally substituted with pyrrolyl or pyrazolyl; and each of R$^a$, R$^b$, and R$^c$ is independently selected from hydrogen, methoxy, and fluoro;

or a pharmaceutically acceptable salt thereof.

4. The method of claim 2, wherein:

R$^1$ and R$^2$ are independently selected from H, methyl, ethyl, or taken together are propylidene, allylidene, or CH$_2$═;

X is methylene or ethylene;

R$^5$ is phenyl, quinolinyl, isoquinolinyl, indolyl, furyl, thienyl, pyrazolyl, quinoxalinyl, naphthyl, or pyrrolyl, and substituted with between 0 and 3 substituents independently selected from methyl, methoxy, fluoro, and bromo; and R$^8$ is H, methyl, ethyl, hydroxyethyl, or benzyl; wherein benzyl is optionally substituted with pyrrolyl or pyrazolyl;

or a pharmaceutically acceptable salt thereof.

5. The method of claim 1, wherein said compound is a compound of the formula:

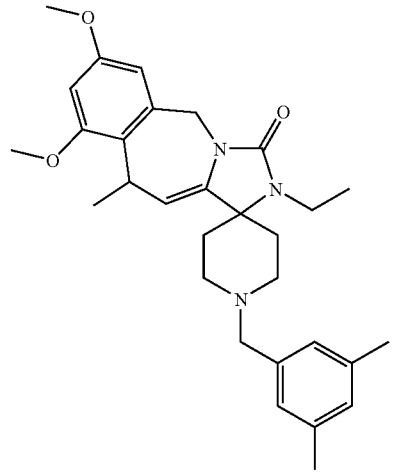

or a pharmaceutically acceptable salt thereof.

6. The method of claim 1, wherein said compound is a compound of the formula:

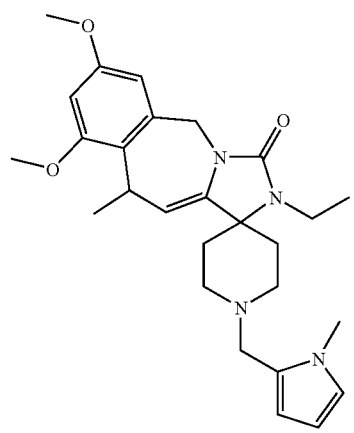

or a pharmaceutically acceptable salt thereof.

7. The method of claim 1, wherein said autoimmune disease is systemic lupus erythematosus.

8. The method of claim 1, wherein said autoimmune disease is type 1 diabetes mellitus.

9. The method of claim 1, wherein said autoimmune disease is psoriasis.

10. The method of claim 1, wherein said autoimmune disease is atherosclerosis.

* * * * *

UNITED STATES PATENT AND TRADEMARK OFFICE
CERTIFICATE OF CORRECTION

PATENT NO.       : 7,985,746 B2                                    Page 1 of 1
APPLICATION NO.  : 12/299864
DATED            : July 26, 2011
INVENTOR(S)      : Fang et al.

It is certified that error appears in the above-identified patent and that said Letters Patent is hereby corrected as shown below:

In the Claims:
Column 128, Claim 1, Line 55: Please correct "CH=CH–" to read -- –CH=CH– --

Signed and Sealed this
Twenty-second Day of November, 2011

David J. Kappos
*Director of the United States Patent and Trademark Office*